(12) United States Patent
Pappas et al.

(10) Patent No.: US 12,239,681 B2
(45) Date of Patent: Mar. 4, 2025

(54) FORMULATIONS AND METHODS FOR SKIN CARE

(71) Applicant: AMILYFE, LLC, Norwood, MA (US)

(72) Inventors: Apostolos Pappas, Norwood, MA (US); Olga Ilnytska, Norwood, MA (US)

(73) Assignee: AMILYFE, LLC, Norwood, MA (US)

( * ) Notice: Subject to any disclaimer, the term of this patent is extended or adjusted under 35 U.S.C. 154(b) by 0 days.

(21) Appl. No.: 18/764,014

(22) Filed: Jul. 3, 2024

(65) Prior Publication Data

US 2024/0350571 A1    Oct. 24, 2024

Related U.S. Application Data

(63) Continuation of application No. PCT/US2022/082663, filed on Dec. 30, 2022.

(60) Provisional application No. 63/296,033, filed on Jan. 3, 2022.

(51) Int. Cl.

| | | |
|---|---|---|
| A61K 36/00 | (2006.01) | |
| A61K 8/44 | (2006.01) | |
| A61K 8/49 | (2006.01) | |
| A61K 8/67 | (2006.01) | |
| A61K 8/9789 | (2017.01) | |
| A61K 9/00 | (2006.01) | |
| A61K 31/07 | (2006.01) | |
| A61K 31/11 | (2006.01) | |
| A61K 31/198 | (2006.01) | |
| A61K 31/203 | (2006.01) | |
| A61K 31/232 | (2006.01) | |
| A61K 31/405 | (2006.01) | |
| A61K 36/32 | (2006.01) | |
| A61K 36/324 | (2006.01) | |
| A61K 45/06 | (2006.01) | |
| A61K 47/24 | (2006.01) | |
| A61K 47/38 | (2006.01) | |
| A61Q 19/00 | (2006.01) | |

(52) U.S. Cl.
CPC .............. *A61K 36/324* (2013.01); *A61K 8/44* (2013.01); *A61K 8/442* (2013.01); *A61K 8/492* (2013.01); *A61K 8/671* (2013.01); *A61K 8/9789* (2017.08); *A61K 9/00* (2013.01); *A61K 31/07* (2013.01); *A61K 31/11* (2013.01); *A61K 31/198* (2013.01); *A61K 31/203* (2013.01); *A61K 31/232* (2013.01); *A61K 31/405* (2013.01); *A61K 36/32* (2013.01); *A61K 45/06* (2013.01); *A61K 47/24* (2013.01); *A61K 47/38* (2013.01); *A61Q 19/00* (2013.01); *A61K 2800/10* (2013.01)

(58) Field of Classification Search
CPC ................................................... A61K 36/324
See application file for complete search history.

(56) References Cited

U.S. PATENT DOCUMENTS

| | | |
|---|---|---|
| 5,859,208 A | 1/1999 | Fiddes et al. |
| 2007/0092461 A1 | 4/2007 | Gupta |
| 2008/0050346 A1 | 2/2008 | Jimenez et al. |
| 2010/0247563 A1 | 9/2010 | Hines et al. |
| 2011/0183040 A1 | 7/2011 | Ermolin et al. |
| 2012/0225029 A1 | 9/2012 | Al-Qahtani |
| 2015/0299311 A1 | 10/2015 | Reversade |
| 2021/0283081 A1 | 9/2021 | Vidyasagar et al. |

*Primary Examiner* — Qiuwen Mi
(74) *Attorney, Agent, or Firm* — Greenberg Traurig, LLP

(57) ABSTRACT

Cosmetic and pharmaceutical formulations comprising specific amino acid combinations are described herein. Such formulations strengthen and enhance skin epithelial cell barrier function, thereby reducing moisture loss from the skin and restoring skin's structural integrity, epithelial differentiation, intercellular adhesion, and intracellular signaling and/or promoting maintenance of these features. Additional formulations described here comprise a therapeutically effective amount of free amino acids and a therapeutically effective amount of a plant extract for skin barrier repair. Methods for administering these formulations for cosmetic and/or therapeutic purposes and uses thereof for same are also described herein, including the use thereof in the preparation of medicaments.

13 Claims, 17 Drawing Sheets

| Most Effective cAA [4mM] Treatment | Least Effective cAA [*mM] Treatment | Control: DMEM |
|---|---|---|
| Combo #1<br>4 cAA | Gln, Gly, Ala, Ser | Combo #3<br>3 cAA | Cys$^1$, His$^{0.5}$, Tyr$^1$ |
| Combo #2<br>6 cAA | Gln, Gly, Ala, Ser, Ile, Val | Combo #5<br>4 cAA | Cys$^1$, His$^{0.5}$, Leu$^4$, Asp$^2$ |
| Combo #4<br>5 cAA | Gln, Gly, Ala, Ser, Val | | |
| Combo #6<br>7 cAA v1 | Gln, Gly, Ala, Ser, Ile, Val, Arg | | |
| Combo #7<br>7 cAA v2 | Gln, Gly, Ala, Ser, Ile, Val, Thr | | |

FIG. 2

Gene Expression Summary

| Genes UP w Combo#1 4AA | Fold increase (x Un-Treated) | Genes up Combo#2 6AA (8/10) | Fold increase (x Un-Treated) |
|---|---|---|---|
| *FLG | 5.0 | *FLG | 6.9 |
| *+EGF | 4.1 | +FGF2 | 6.0 |
| *PPARD | 3.5 | *+EGF | 5.7 |
| +PDGF | 2.7 | +MKI67 | 4.7 |
| +FGF2 | 2.1 | *PPARD | 3.8 |
| +MKI67 | 1.8 | *CPT2 | 2.6 |
|  |  | +PDGF | 2.6 |
|  |  | *TGM4 | 2.3 |
| Score | 15 | | 22.5 |

Scoring system developed:
of points given to relative expression

| Significantly higher | 3 | ↑ ≥ 2.5 fold |
|---|---|---|
| Higher | 2 | ↑ 2-2.5 fold |
| High | 1 | ↑ 1.5-2 fold |

FIG. 3

Gene Expression Summary

| Gene | Combo#1 4AA | Combo#2 6AA | Combo#3 3AA |
|---|---|---|---|
| *+EGF | 4.1 | 5.2 | - |
| *FLG | - | - | - |
| +FGF2 | 1.6 | 6.6 | 2.7 |
| *PPARD | 1.7 | 1.6 | - |
| +PDGF | 2.1 | 1.7 | 1.8 |
| +MKI67 | - | - | - |
| *CPT2 | - | 1.5 | - |
| *TGM4 | - | 1.8 | - |
| Score | 7 | 10 | 4 |

Scoring system developed: # of points given to relative expression

| | | |
|---|---|---|
| Significantly higher | 3 | ↑ > 2.5 fold |
| Higher | 2 | ↑ 2-2.5 fold |
| High | 1 | ↑ 1.5-2 fold |

FIG. 4

| | CTR | BSXL 0.1% | BSXL 0.25% | BSXL 0.5% | 4GAA 1mM | 4GAA 4mM | 4GAA 1mM + BSXL 0.25% | 4GAA 4mM + BSXL 0.5% |
|---|---|---|---|---|---|---|---|---|
| | 1.0 | 1.1 | 2.5 | 3.1 | 4.1 | 5.6 | 6.2 | 10.6 |
| | 1.0 | 1.4 | 1.6 | 4.0 | 4.8 | 6.5 | 7.6 | 12.8 |
| | 1.0 | 1.1 | 2.2 | 3.0 | 4.8 | 5.5 | 10.1 | 12.4 |
| Average | 1.0 | 1.2 | 2.1 | 3.4 | 4.6 | 5.9 | 8.0 | 11.9 |
| p-value (t test) | | 0.067 | 0.016 | 0.002 | 0.000 | 0.000 | 0.003 | 0.000 |

| | CTR untr | 4GAA 1mM | BSXL 0.25% | 4GAA 1mM+ BSXL 0.25% | 4GAA 4mM | BSXL 1% | 4GAA 4mM+ BSXL 1% |
|---|---|---|---|---|---|---|---|
| | 0.78 | 2.73 | 2.25 | 24.38 | 4.81 | 11.05 | 23.54 |
| | 1.16 | 5.76 | 1.48 | 7.71 | 6.79 | 9.20 | 43.34 |
| | 1.06 | 1.05 | | 2.41 | 4.04 | 13.28 | 32.04 |
| Average | 1.00 | 3.18 | 1.86 | 11.50 | 5.22 | 11.18 | 32.97 |
| p-value | | 0.190 | 0.075 | 0.188 | 0.007 | 0.001 | 0.005 |
| | n=3 | n=3 | n=2 | n=3 | n=3 | n=3 | n=3 |

| | CTR | 4GAA | 3BAA | BSXL 0.5% | PA 100μM | 4GAA+ BSXL 0.5% | 3BAA + BSXL 0.5% | 4GAA + PA 100μM | 3BAA + PA 100μM | 0h complete |
|---|---|---|---|---|---|---|---|---|---|---|
| | 1.0 | 3.0 | 0.8 | 6.1 | 0.8 | 19.1 | 2.2 | 2.4 | 0.6 | 0.5 |
| | 1.1 | 3.5 | 0.6 | 2.3 | 1.2 | 21.8 | 1.7 | 3.5 | 0.6 | 1.0 |
| | 0.9 | 2.4 | 0.5 | 4.6 | 1.0 | 27.5 | 1.7 | 2.5 | 0.7 | 0.7 |
| Average | 1.0 | 3.0 | 0.6 | 4.3 | 1.0 | 22.8 | 1.9 | 2.8 | 0.6 | 0.7 |
| p-value | 0.004 | 0.018 | 0.040 | 0.04 | | 0.001 | 0.006 | 0.008 | 0.008 | |

| EGF | CTR | 4GAA 4 mM | 3BAA | BSXL 0.5% | PA 200µM | 4GAA +BSXL 0.5% | 3BAA+ BSXL 0.5% | 4GAA+PA 200µM | 3BAA+PA 200µM |
|---|---|---|---|---|---|---|---|---|---|
| | 1.1 | 3.6 | 0.7 | 5.9 | 1.5 | 10.9 | 1.7 | 1.3 | 0.7 |
| | 0.9 | 4.1 | 0.6 | 5.2 | 0.9 | 12.7 | 2.4 | 1.3 | 0.7 |
| | 1 | 2.5 | 0.7 | 3.5 | 0.9 | 10.1 | 4.3 | 2.1 | 0.8 |
| Average | 1.00 | 3.40 | 0.67 | 4.87 | 1.10 | 11.23 | 2.80 | 1.57 | 0.73 |
| p-value (t test) | | 0.007 | 0.007 | 0.006 | | 0.000 | 0.082 | 0.106 | 0.016 |

|  | CTR | BSXL 0.25% | 4GAA 1mM | 4GAA 1mM+ BSXL 0.25% | BA 10µM | 4GAA 1mM + BA 10µM | BA 2µM | BA 50µM | 4GAA 1mM + BA 10µM | 4GAA 1mM+ BA 50µM | 4GAA 4mM+ BSXL 0.25% | 4GAA 4mM |
|---|---|---|---|---|---|---|---|---|---|---|---|---|
|  | 0.7 | 5.0 | 4.0 | 11.1 | 1.1 | 2.8 | 0.8 | 1.1 | 3.1 | 1.8 | 15.0 | 3.4 |
|  | 1.2 | 3.8 | 2.3 | 5.7 | 0.9 | 2.5 | 1.1 | 0.5 | 3.0 | 3.3 | 12.0 | 3.0 |
|  | 1.1 | 7.2 | 2.5 | 6.8 | 1.1 | 2.8 |  |  |  |  |  |  |
| Average | 1.0 | 5.3 | 2.9 | 7.9 | 1.0 | 2.7 | 0.9 | 0.8 | 3.1 | 2.5 | 13.5 | 3.2 |
| p-value, t test |  | 0.013 | 0.026 | 0.014 | 0.819 | 0.001 | 0.712 | 0.524 | 0.001 | 0.274 | 0.002 | 0.009 |

| | CTR | 4GAA 4mM | 4OAA 4mM | BSXL 0.5% | BSXL 0.5% + 4GAA4mM | BSXL.5%+ 4OAA 4mM | EGF 1ng/ml | EGF 10ng/ml |
|---|---|---|---|---|---|---|---|---|
| | 0.9 | 2.3 | 1.2 | 1.3 | 3.1 | 1.3 | 0.9 | 1.5 |
| | 0.9 | 2.1 | 0.7 | 1.3 | 3.5 | 3.3 | 0.9 | 0.8 |
| | 1.2 | 2.1 | 1.2 | 1.9 | 4.1 | 3.2 | 1.6 | 2.3 |
| Average | 1.0 | 2.2 | 1.1 | 1.5 | 3.6 | 2.6 | 1.1 | 1.6 |
| p-value (t test) | | 0.000 | 0.780 | 0.096 | 0.001 | 0.066 | 0.633 | 0.290 |

| Donor | CTR | 4GAA 4mM | BSXL 0.5% | BSXL0.5%+ 4GAA 4mM |
|---|---|---|---|---|
| A | 1.0 | 2.16 | 1.50 | 3.57 |
| G | 1.0 | 4.04 | 3.06 | 13.99 |
| T | 1.0 | 2.969 | 3.05 | 9.80 |
| Average | 1.0 | 3.06 | 2.54 | 9.12 |
| p-value (two tail Student's t-test) | | 0.0195 | 0.040 | 0.055 |

FIG. 14A

| | Donor A | | | Donor G | | | | | | | | |
|---|---|---|---|---|---|---|---|---|---|---|---|---|
| CTR | 0.9 | 0.9 | 1.2 | 1 | 1 | 1 | 0.6 | 1.1 | 1.3 | 1 | 1.1 | 0.9 |
| 4GAA 4mM | 2.3 | 2.1 | 2.1 | 5.6 | 6.5 | 5.5 | 2.4 | 2.7 | 4.6 | 3 | 3.5 | 2.4 |
| BSXL 0.5% | 1.3 | 1.3 | 1.9 | 3.1 | 4 | 3 | 1.7 | 1.8 | 1 | 6.1 | 2.3 | 4.6 |
| BSXL0.5%+ 4GAA4mM | 3.1 | 3.5 | 4.1 | 10.6 | 12.8 | 12.4 | 7.2 | 6.9 | 7.7 | 19.1 | 21.8 | 27.5 |

| | Donor T | | | | | | Average |
|---|---|---|---|---|---|---|---|
| CTR | 0.9 | 0.9 | 1.2 | 1.1 | 0.9 | 1.0 | 1 |
| 4GAA 4mM | 2.3 | 2.1 | 2.1 | 3.6 | 4.1 | 2.5 | 3.4 |
| BSXL 0.5% | 1.3 | 1.3 | 1.9 | 5.9 | 5.2 | 3.5 | 2.8 |
| BSXL0.5%+ 4GAA4mM | 3.1 | 3.5 | 4.1 | 10.9 | 12.7 | 10.1 | 10.9 |

FIG. 14B

FORMULATIONS AND METHODS FOR SKIN CARE

CROSS-REFERENCE TO RELATED APPLICATIONS

The present application is a U.S. Application filed under 35 U.S.C. § 111 (a), which under 35 U.S.C. § 365 (c), claims the benefit of International Application No. PCT/US2022/082663, filed Dec. 30, 2022, which claims the priority benefit of U.S. Provisional Patent Application No. 63/296,033 entitled "FORMULATIONS AND METHODS FOR SKIN CARE," filed on Jan. 3, 2022, the disclosure of each of which is incorporated herein by reference in its entirety.

FIELD OF THE DISCLOSURE

The present disclosure is directed to formulations and their methods of use in improving skin barrier repair.

BACKGROUND

Skin diseases and conditions can cause significant physical discomfort and emotional distress for patients afflicted with such diseases and conditions. Common skin diseases and conditions include atopic dermatitis, psoriasis, and ichthyosis. Xerosis cutis (dry skin) is a very common dermatological disorder that afflicts a significant subset of the population. Skin diseases, conditions, and disorders that afflict patients frequently vary with age and are impacted by lifestyle and geographical area. Despite the high prevalence of skin diseases, conditions, and disorders in the population and the adverse effects of same on people's quality-of-life and the economic burden associated therewith, there are few effective treatments available. Effective formulations for addressing cosmetic skin care objectives and treatments for diseases, conditions, and disorders of the skin represent unmet needs.

SUMMARY

Cosmetic and pharmaceutical formulations are described herein. Such formulations strengthen and enhance skin epithelial cell barrier function, thereby reducing moisture loss from the skin and restoring skin's structural integrity, intercellular adhesion, and biochemistry and/or promoting maintenance of these features. Described herein are formulations comprising, consisting essentially of, or consisting of a therapeutically effective amount of free amino acids of alanine, glutamine, glycine, and serine; and optionally, a therapeutically effective amount of at least one additional free amino acid of valine, isoleucine, arginine, threonine, or tryptophan, or any combination thereof. Also encompassed herein are methods for maintaining and/or improving barrier integrity of skin cells in a subject in need thereof or for improving a cosmetic skin condition of a human comprising administering to the subject a formulation described herein. Also encompassed is a use of the formulations described herein for maintaining and/or improving barrier integrity of skin cells in a subject in need thereof or for improving a cosmetic skin condition of a human comprising administering to the subject or human a formulation described herein. Formulations described herein may also be used in the preparation of a dermatological medicament for treating a cosmetic skin condition in a subject in need thereof. Such methods, uses, and dermatological medicaments are administered or used to improve the cosmetic skin condition. In some embodiments, the cosmetic skin condition is associated with aging of the skin. Cosmetic skin conditions may relate to at least one visual property, or at least one tactile property, or a combination of visual and tactile properties of the skin. Accordingly, improving the at least one visual property, or at least one tactile property, or a combination of visual and tactile properties of the skin reduces the length, depth, and/or other dimension of lines and/or wrinkles in the skin. Also encompassed herein are methods for treating and/or preventing a skin disease, condition, or disorder in a subject in need thereof comprising administering to the subject a formulation described herein. Also encompassed is a use of the formulations described herein for treating and/or preventing a skin disease, condition, or disorder in a subject in need thereof comprising administering to the subject a formulation described herein. Formulations described herein may also be used in the preparation of a medicament for treating and/or preventing a skin disease, condition, or disorder in a subject in need thereof.

Embodiment 1. A formulation for administration to skin comprising: as free amino acids, a therapeutically effective amount of a combination of alanine, glutamine, glycine, and serine, or salts thereof; and optionally, a therapeutically effective amount of at least one additional free amino acid of valine, isoleucine, arginine, threonine, or tryptophan, or salts thereof, or any combination thereof; wherein the therapeutically effective amount of the combination of glutamine, glycine, alanine, and serine, or salts thereof, and the therapeutically effective amount of the at least one additional free amino acid or salts thereof, improves barrier integrity of skin cells; and optionally, a dermatologically acceptable carrier; wherein the formulation improves barrier integrity of the skin cells, when tested by a method detecting expression of a barrier marker gene (e.g., CPT2, EGF, FGF2, FLG, MKI67, PDGF, PPARD, TGM4) and determining that the barrier marker gene is modulated by a 1.5-7 average fold change of amino acid treated as compared to amino acid untreated skin.

Embodiment 2. The formulation of embodiment 1, wherein the free amino acids comprise, consist essentially of, or consist of glutamine, glycine, alanine, serine, and valine, or salts thereof; and at least one additional amino acid of isoleucine, arginine, threonine, or tryptophan, or salts thereof, or any combination thereof.

Embodiment 3. The formulation according to embodiment 1 or embodiment 2, wherein the free amino acids comprise, consist essentially of, or consist of glutamine, glycine, alanine, serine, valine, and isoleucine, or salts thereof; and at least one additional amino acid of arginine, or threonine, or salts thereof, or any combination thereof.

Embodiment 4. The formulation according to embodiment 1 or embodiment 2, wherein the free amino acids comprise, consist essentially of, or consist of glutamine, glycine, alanine, serine, and valine, or salts thereof.

Embodiment 5. The formulation according to embodiment 1 or embodiment 2, wherein the free amino acids comprise, consist essentially of, or consist of glutamine, glycine, alanine, serine, valine, and isoleucine, or salts thereof.

Embodiment 6. The formulation according to any one of embodiments 1-3, wherein the free amino acids comprise, consist essentially of, or consist of glutamine, glycine, alanine, serine, valine, isoleucine, and arginine, or salts thereof.

Embodiment 7. The formulation according to any one of embodiments 1-3, wherein the free amino acids comprise, consist essentially of, or consist of glutamine, glycine, alanine, serine, valine, isoleucine, and threonine, or salts thereof.

Embodiment 8. The formulation of embodiment 1, wherein the free amino acids comprise, consist essentially of, or consist of glutamine, glycine, alanine, and serine, or salts thereof; and at least one additional amino acid of isoleucine, arginine, threonine, or tryptophan, or salts thereof, or any combination thereof.

Embodiment 9. The formulation according to embodiment 8, wherein the free amino acids comprise, consist essentially of, or consist of glutamine, glycine, alanine, serine, and isoleucine, or salts thereof.

Embodiment 10. The formulation according to embodiment 8, wherein the free amino acids comprise, consist essentially of, or consist of glutamine, glycine, alanine, serine, and arginine, or salts thereof.

Embodiment 11. The formulation according to embodiment 8, wherein the free amino acids comprise, consist essentially of, or consist of glutamine, glycine, alanine, serine, and threonine, or salts thereof.

Embodiment 15. The formulation according to embodiment 8, wherein the free amino acids comprise, consist essentially of, or consist of glutamine, glycine, alanine, serine, and tryptophan, or salts thereof.

Embodiment 16. The formulation according to embodiment 8, wherein the free amino acids comprise, consist essentially of, or consist of glutamine, glycine, alanine, serine, and isoleucine, or salts thereof; and at least one additional amino acid of arginine, or threonine, or tryptophan, or salts thereof, or any combination thereof.

Embodiment 17. The formulation according to embodiment 16, wherein the free amino acids comprise, consist essentially of, or consist of glutamine, glycine, alanine, serine, isoleucine, and arginine, or salts thereof.

Embodiment 18. The formulation according to embodiment 16, wherein the free amino acids comprise, consist essentially of, or consist of glutamine, glycine, alanine, serine, isoleucine, and threonine, or salts thereof.

Embodiment 19. The formulation according to embodiment 16, wherein the free amino acids comprise, consist essentially of, or consist of glutamine, glycine, alanine, serine, isoleucine, and tryptophan, or salts thereof.

Embodiment 20. The formulation according to embodiment 16, wherein the free amino acids comprise, consist essentially of, or consist of glutamine, glycine, alanine, serine, isoleucine, arginine, and threonine, or salts thereof.

Embodiment 21. The formulation according to embodiment 16, wherein the free amino acids comprise, consist essentially of, or consist of glutamine, glycine, alanine, serine, isoleucine, arginine, and tryptophan, or salts thereof.

Embodiment 22. The formulation according to embodiment 16, wherein the free amino acids comprise, consist essentially of, or consist of glutamine, glycine, alanine, serine, isoleucine, threonine, and tryptophan, or salts thereof.

Embodiment 23. The formulation according to embodiment 16, wherein the free amino acids comprise, consist essentially of, or consist of glutamine, glycine, alanine, serine, isoleucine, arginine, threonine, and tryptophan, or salts thereof.

Embodiment 24. The formulation according to embodiment 8, wherein the free amino acids comprise, consist essentially of, or consist of glutamine, glycine, alanine, serine, and arginine, or salts thereof; and at least one additional amino acid of isoleucine, threonine, or tryptophan, or salts thereof, or any combination thereof.

Embodiment 25. The formulation according to embodiment 8, wherein the free amino acids comprise, consist essentially of, or consist of glutamine, glycine, alanine, serine, and threonine, or salts thereof; and at least one additional amino acid of isoleucine, arginine, or tryptophan, or salts thereof, or any combination thereof.

Embodiment 26. The formulation according to embodiment 8, wherein the free amino acids comprise, consist essentially of, or consist of glutamine, glycine, alanine, serine, and tryptophan, or salts thereof; and at least one additional amino acid of isoleucine, arginine, or threonine, or salts thereof, or any combination thereof.

Embodiment 27. The formulation according to any one of embodiments 1-26, wherein each of the free amino acids, or salts thereof, is present at a concentration ranging from 0.05 mM to 20 mM.

Embodiment 28. The formulation according to any one of embodiments 1-27, wherein each of the free amino acids, or salts thereof, is present at a concentration ranging from 0.05 mM to 10 mM.

Embodiment 29. The formulation according to any one of embodiments 1-28, wherein each of the free amino acids, or salts thereof, is present at a concentration ranging from 0.05 mM to 5 mM.

Embodiment 30. The formulation according to any one of embodiments 1-26, wherein each of the free amino acids, or salts thereof, is present at a concentration of ranging from 0.1 mM to 10 mM.

Embodiment 31. The formulation according to any one of embodiments 1-26, wherein each of the free amino acids, or salts thereof, is present at a concentration of ranging from 0.1 mM to 5 mM.

Embodiment 32. The formulation according to any one of embodiments 1-11, wherein each of the free amino acids, or salts thereof, is present at a concentration of ranging from 0.1 mM to equal to or less than 4 mM.

Embodiment 33. The formulation according to any one of embodiments 1-26, wherein each of the free amino acids, or salts thereof, is present at a concentration ranging from equal to or greater than 0.5 mM to equal to or less than 4 mM.

Embodiment 34. The formulation according to any one of embodiments 1-33, wherein, if present, free amino acids of cysteine, or salts thereof, are present at a concentration of equal to or less than 1 mM; if present, free amino acids of histidine, or salts thereof, are present at a concentration of equal to or less than 0.5 mM; if present, free amino acids of tyrosine, or salts thereof, are present at a concentration of equal to or less than 1 mM; if present, free amino acids of leucine, or salts thereof, are present at a concentration of equal to or less than 4 mM; or if present, free amino acids of aspartic acid, or salts thereof, are present at a concentration of equal to or less than 2 mM; or any combination thereof.

Embodiment 35. The formulation according to any one of embodiments 1-34, wherein the formulation does not comprise free amino acids of cysteine, histidine, tyrosine, leucine, aspartic acid, taurine, taurate, or glutamate, or salts thereof, or any combination thereof.

Embodiment 36. The formulation according to any one of embodiments 1-35, wherein the formulation is administered to the skin or administrable via transdermal, subcutaneous, or topical administration.

Embodiment 37. A method for maintaining and/or improving barrier integrity of skin cells in a subject in need thereof, the method comprising administering a formulation of any one of embodiments 1-36 to the skin of the subject.

Embodiment 38. The method according to embodiment 37, wherein the formulation is administered to improve a cosmetic skin condition.

Embodiment 39. The method according to embodiment 38, wherein the cosmetic skin condition is associated with aging of the skin.

Embodiment 40. The method according to any one of embodiments 37-39, wherein the formulation is administered to improve at least one visual property, or at least one tactile property, or a combination of visual and tactile properties of the skin.

Embodiment 41. The method according to embodiment 40, wherein improving the at least one visual property, or at least one tactile property, or a combination of visual and tactile properties of the skin reduces the length, depth, and/or other dimension of lines and/or wrinkles in the skin.

Embodiment 42. The method according to embodiment 37, wherein the subject in need thereof is afflicted with a skin condition.

Embodiment 43. The method according to embodiment 42, wherein the skin condition comprises atopic dermatitis, dermatitis, psoriasis, pruritus, eczema, a wound, or a burn.

Embodiment 44. The method according to any one of embodiments 37-43, wherein the subject is a human.

Embodiment 45. A method for improving a cosmetic skin condition of a human, the method comprising administering the formulation according to any one of embodiments 1-36 to the human's skin in an amount effective to improve at least one visual property, or at least one tactile property, or a combination of visual and tactile properties of the skin.

Embodiment 46. The method according to embodiment 45, wherein the cosmetic skin condition is associated with aging of the skin.

Embodiment 47. The method according to embodiment 45 or embodiment 46, wherein improving the at least one visual property, or at least one tactile property, or a combination of visual and tactile properties of the skin reduces the length, depth, and/or other dimension of lines and/or wrinkles in the skin Embodiment 48. Use of a formulation according to any one of embodiments 1-36 for the treatment of a cosmetic skin condition.

Embodiment 49. The use according to embodiment 48, wherein the cosmetic skin condition is associated with aging of the skin.

Embodiment 50. The use according to embodiment 48 or embodiment 49, wherein the formulation is administered to improve at least one visual property, or at least one tactile property, or a combination of visual and tactile properties of the skin.

Embodiment 51. The according to embodiment 50, wherein improving the at least one visual property, or at least one tactile property, or a combination of visual and tactile properties of the skin reduces the length, depth, and/or other dimension of lines and/or wrinkles in the skin.

Embodiment 52. Use of a formulation according to any one of embodiments 1-36 for the treatment of a skin condition.

Embodiment 53. The use according to embodiment 52, wherein the skin condition comprises atopic dermatitis, dermatitis, psoriasis, pruritus, eczema, a wound, or a burn.

Embodiment 58. Use of a formulation according to any one of embodiments 1-36 in the preparation of a dermatological medicament for treating a cosmetic skin condition in a subject in need thereof.

Embodiment 59. The dermatological medicament according to embodiment 58, wherein the cosmetic skin condition is associated with aging of the skin.

Embodiment 60. The dermatological medicament according to embodiment 58 or embodiment 59, wherein the dermatological medicament is administrable to improve at least one visual property, or at least one tactile property, or a combination of visual and tactile properties of the skin.

Embodiment 61. The dermatological medicament according to embodiment 60, wherein improving the at least one visual property, or at least one tactile property, or a combination of visual and tactile properties of the skin reduces the length, depth, and/or other dimension of lines and/or wrinkles in the skin.

Embodiment 62. Use of a formulation according to any one of embodiments 1-36 in the preparation of a pharmaceutical medicament for treating a skin condition in a subject in need thereof.

Embodiment 63. The pharmaceutical medicament according to embodiment 62, wherein the skin condition comprises atopic dermatitis, dermatitis, psoriasis, pruritus, eczema, a wound, or a burn.

In some embodiments, a topical formulation, comprises (or consists essentially of or consists of): as free amino acids or salts thereof, a therapeutically effective amount of a combination comprising (or consisting essentially of, or consisting of): at least one of: alanine, glutamine, glycine, and serine; a therapeutically effective amount of a plant extract, wherein the plant extract comprises (or consists essentially of or consists of): a *Boswellia* extract (e.g., *Boswellia serrata*; Burseraceae family; olibanum; frankincense); and optionally, a dermatologically acceptable carrier and/or additive.

Additional embodiments provide a topical formulation, comprising (or consisting essentially of or consisting of): as free amino acids, a therapeutically effective amount of a combination comprising (or consisting essentially of or consisting of): alanine, glutamine, glycine, and serine, or salts thereof; a therapeutically effective amount of a plant extract combination (e.g., *Boswellia serrata* resin extract, cellulose (microcrystalline), lecithin, silica), comprising (or consisting essentially of, or consisting of): *Boswellia* extract (e.g., *Boswellia serrata*; Burseraceae family; olibanum; frankincense); a texturing and/or a bulking agent (e.g., cellulose (microcrystalline)); a phospholipid (e.g., lecithin or phosphatidylcholine, ceramide); and an anti-caking agent (e.g., silica, adsorbs water in hygroscopic applications); and optionally, a dermatologically acceptable carrier and/or additive.

In further embodiments, a formulation for administration to skin comprises (or consists essentially of or consists of): a therapeutically effective amount of a combination of free amino acids comprising (or consisting essentially of or consisting of): alanine, glutamine, glycine, and serine, or salts thereof; a therapeutically effective amount of a plant extract combination comprising (consisting essentially of or consisting of) (e.g., *Boswellia serrata* resin extract, cellulose (microcrystalline), lecithin, silica): *Boswellia* extract (e.g., *Boswellia serrata*; Burseraceae family; olibanum; frankincense); a texturing and/or a bulking agent (e.g., cellulose (microcrystalline); a phospholipid (e.g., lecithin); and an anti-caking agent (e.g., silica, adsorbs water in hygroscopic applications); and optionally, a dermatologically acceptable carrier, wherein the therapeutically effective amount of the combination of free amino acids and the therapeutically effective amount of the plant extract combination improves skin barrier repair (e.g., skin barrier correction, skin barrier strengthening, skin barrier preservation, wound healing; growth, stimulation, proliferation, differentiation, and migration of epidermal cells, keratinocyte, endothelial cells, and fibroblasts; facilitates dermal regeneration) when tested by a method detecting expression of a barrier marker gene (e.g., EGF) and determining that the barrier marker gene is increased by a 1.5-40 average fold increase of amino acid treated as compared to amino acid untreated skin (see, e.g., FIGS. 8-14), wherein the formulation improves skin barrier repair (e.g., skin barrier correction, skin barrier strengthening, skin barrier preservation, wound healing; growth, stimulation, proliferation, differentiation, and migration of epidermal cells, keratinocyte, endothelial cells, and fibroblasts; facilitates dermal regeneration), wherein an improvement in skin barrier repair is indicated by an average fold increase of a skin barrier marker gene (e.g., EGR) expression of: 1.5 or greater (e.g., 1.7; 1.9; 2.1; 2.3; 2.5; 2.7; 2.9; 3.1; 3.3; 3.5; 3.7; 3.9; 4.1; 4.3; 4.5; 4.7; 4.9; 5.1; 5.3; 5.5; 5.7; 5.9; 6.1; 6.3; 6.5; 6.7; 6.9; 7.1; 7.3; 7.5; 7.7; 7.9; 8.1; 8.3; 8.5; 8.7; 8.9; 9.1; 9.3; 9.5; 9.7; 9.9; 10.1; 10.3; 10.5; 10.7; 10.9; 11.1; 11.3; 11.5; 11.7; 11.9; 12.1; 12.3; 12.5; 12.7; 12.9; 13.1; 13.3; 13.5; 13.7; 13.9; 14.1; 14.3; 14.5; 14.7; 14.9; 15.1; 15.3; 15.5; 15.7; 15.9; 16.1; 16.3; 16.5; 16.7; 16.9; 17.1; 17.3; 17.5; 17.7; 17.9; 18.1; 18.3; 18.5; 18.7; 18.9; 19.1; 19.3; 19.5; 19.7; 19.9; 20.1; 20.3; 20.5; 20.7; 20.9; 21.1; 21.3; 21.5; 21.7; 21.9; 22.1; 22.3; 22.5; 22.7; 22.9; 23.1; 23.3; 23.5; 23.7; 23.9; 23.1; 23.3; 23.5; 23.7; 23.9; 24.1; 24.3; 24.5; 24.7; 24.9; 25.1; 25.3; 25.5; 25.7; 25.9; 26.1; 26.3; 26.5; 26.7; 26.9; 27.1; 27.3; 27.5; 27.7; 27.9; 28.1; 28.3; 28.5; 28.7; 28.9; 29.1; 29.3; 29.5; 29.7; 29.9; 30.1; 30.3; 30.5; 30.7; 30.9; 31.1; 31.3; 31.5; 31.7; 31.9; 32.1; 32.3; 32.5; 32.7; 32.9; 33.1; 33.3; 33.5; 33.7; 33.9; 34.1; 34.3; 34.5; 34.7; 34.9; 35.1; 35.3; 35.5; 35.7; 35.9; 36.1; 36.3; 36.5; 36.7; 36.9; 37.1; 37.3; 37.5; 37.7; 37.9; 38.1; 38.3; 38.5; 38.7; 38.9; 39.1; 39.3; 39.5; 39.7; 39.9; 40.1; 40.3; 40.5; 40.7; 40.9; 41.1; 41.3; 41.5); 40 or less (e.g., 39.8; 39.6; 39.4; 39.2; 39; 38.8; 38.6; 38.4; 38.2; 38; 37.8; 37.6; 37.4; 37.2; 37; 36.8; 36.6; 36.4; 36.2; 36; 35.8; 35.6; 35.4; 35.2; 35; 34.8; 34.6; 34.4; 34.2; 34; 33.8; 33.6; 33.4; 33.2; 33; 32.8; 32.6; 32.4; 32.2; 32; 31.8; 31.6; 31.4; 31.2; 31; 30.8; 30.6; 30.4; 30.2; 30; 29.8; 29.6; 29.4; 29.2; 29; 28.8; 28.6; 28.4; 28.2; 28; 27.8; 27.6; 27.4; 27.2; 27; 26.8; 26.6; 26.4; 26.2; 26; 25.8; 25.6; 25.4; 25.2; 25; 24.8; 24.6; 24.4; 24.2; 24; 23.8; 23.6; 23.4; 23.2; 23; 22.8; 22.6; 22.4; 22.2; 22; 21.8; 21.6; 21.4; 21.2; 21; 20.8; 20.6; 20.4; 20.2; 20; 19.8; 19.6; 19.4; 19.2; 19; 18.8; 18.6; 18.4; 18.2; 18; 17.8; 17.6; 17.4; 17.2; 17.2; 17; 16.8; 16.6; 16.4; 16.2; 16; 15.8; 15.6; 15.4; 15.2; 15; 14.8; 14.6; 14.4; 14.2; 14; 13.8; 13.6; 13.4; 13.2; 13; 12.8; 12.6; 12.4; 12.2; 12; 11.8; 11.6; 11.4; 11.2; 11; 10.8; 10.6; 10.4; 10.2; 10; 9.8; 9.6; 9.4; 9.2; 9; 8.8; 8.6; 8.4; 8.2; 8; 7.8; 7.6; 7.4; 7.2; 7; 6.8; 6.6; 6.4; 6.2; 6; 5.8; 5.6; 5.4; 5.2; 5; 4.8; 4.6; 4.4; 4.2; 4; 3.8; 3.6; 3.4; 3.2; 3; 2.8; 2.6; 2.4; 2.2; 2; 1.8; 1.6; 1.4; 1.2; 1; 0.8; 0.6); or 1.5-40 (e.g., 1.6-39.9; 1.7-39.8; 1.8-39.7; 1.9-39.6; 2-39.5; 2.1-39.4; 2.2-39.3; 2.3-39.2; 2.4-39.1; 2.5-39; 2.6-38.9; 2.7-38.8; 2.8-38.7; 2.9-38.6; 3-38.5; 3.1-38.4; 3.2-38.3; 3.3-38.2; 3.4-38.1; 3.5-38; 3.6-37.9; 3.7-37.8; 3.8-37.7; 3.9-37.6; 4-37.5; 4.1-37.4; 4.2-37.3; 4.3-37.2; 4.4-37.1; 4.5-37; 4.6-36.9; 4.7-36.8; 4.8-36.7; 4.9-36.6; 5-36.5; 5.1-36.4; 5.2-36.3; 5.3-36.2; 5.4-36.1; 5.5-36; 5.6-35.9; 5.7-35.8; 5.8-35.7; 5.9-35.6; 6-35.5; 6.1-35.4; 6.2-35.3; 6.3-35.2; 6.4-35.1; 6.5-35; 6.6-34.9; 6.7-34.8; 6.8-34.7; 6.9-34.6; 7-34.5; 7.1-34.4; 7.2-34.3; 7.3-34.2; 7.4-34.1; 7.5-34; 7.6-33.9; 7.7-33.8; 7.8-33.7; 7.9-33.6; 8-33.5; 8.1-33.4; 8.2-33.3; 8.3-33.2; 8.4-33.1; 8.5-33; 8.6-32.9; 8.7-32.8; 8.8-32.7; 8.9-32.6; 9-32.5; 9.1-32.4; 9.2-32.3; 9.3-32.2; 9.4-32.1; 9.5-32; 9.6-31.9; 9.7-31.8; 9.8-31.7; 9.9-31.6; 10-31.5; 10.1-31.4; 10.2-31.3; 10.3-31.2; 10.4-31.1; 10.5-31; 10.6-30.9; 10.7-30.8; 10.8-30.7; 10.9-30.6; 11-30.5; 11.1-30.4; 11.2-30.3; 11.3-30.2; 11.4-30.1; 11.5-30; 11.6-29.9; 11.7-29.8; 11.8-29.7; 11.9-29.6; 12-29.5; 12.1-29.4; 12.2-29.3; 12.3-29.2; 12.4-29.1; 12.5-29; 12.6-28.9; 12.7-28.8; 12.8-28.7; 12.9-28.6; 13-28.5; 13.1-28.4; 13.2-28.3; 13.3-28.2; 13.4-28.1; 13.5-28; 13.6-27.9; 13.7-27.8; 13.8-27.7; 13.9-27.6; 14-27.5; 14.1-27.4; 14.2-27.3; 14.3-27.2; 14.4-27.1; 14.5-27; 14.6-26.9; 14.7-26.8; 14.8-26.7; 14.9-26.6; 15-26.5; 15.1-26.4; 15.2-26.3; 15.3-26.2; 15.4-26.1; 15.5-26; 15.6-25.9; 15.7-25.8; 15.8-25.7; 15.9-25.6; 16-25.5; 16.1-25.4; 16.2-25.3; 16.3-25.2; 16.4-25.1; 16.5-25; 16.6-24.9; 16.7-24.8; 16.8-24.7; 16.9-24.6; 17-24.5; 17.1-24.4; 17.2-24.3; 17.3-24.2; 17.4-24.1; 17.5-24; 17.6-23.9; 17.7-23.8; 17.8-23.7; 17.9-23.6; 18-23.5; 18.1-23.4; 18.2-23.3; 18.3-23.2; 18.4-23.1; 18.5-23; 18.6-22.9; 18.7-22.8; 18.8-22.7; 18.9-22.6; 19-22.5; 19.1-22.4; 19.2-22.3; 19.3-22.2; 19.4-22.1; 19.5-22; 19.6-21.9; 19.7-21.8; 19.8-21.7; 19.9-21.6; 20-21.5; 20.1-21.4; 20.2-21.3; 20.3-21.2; 20.4-21.1; 20.5-21; 20.6-20.9; 20.7-20.8).

Some embodiments provide a method of improving skin barrier repair of skin of a subject, comprises (or consists essentially of or consists of): administering a topical formulation (according to any one of the preceding formulations or embodiments 64-66), comprising (or consisting essentially of or consisting of): a therapeutically effective amount of a combination of free amino acids comprising (or consisting essentially of or consisting of) at least one of alanine, glutamine, glycine, and serine, or salts thereof; and a therapeutically effective amount of a plant extract combination comprising (consisting essentially of or consisting of) (e.g., *Boswellia serrata* resin extract, cellulose (microcrystalline), lecithin, silica): *Boswellia* extract (e.g., *Boswellia serrata*; Burseraceae family; olibanum; frankincense) alone or optionally in combination with at least one of: a texturing and/or a bulking agent (e.g., cellulose (microcrystalline)); a phospholipid (e.g., lecithin or phosphatidylcholine); and an anti-caking agent (e.g., silica, adsorbs water in hygroscopic applications); and optionally, a dermatologically acceptable carrier and/or additive, wherein when tested by a method detecting expression of a barrier marker gene (e.g., EGF) and determining that the barrier marker gene is increased by a 1.5-40 average fold change in amino acid treated skin as compared to amino acid untreated skin, thereby improving skin barrier repair.

In another further aspect of the method or use, the formulation is sterile.

In certain embodiments, the formulations described herein are in a form of a single unit dose. In one aspect, the formulations described herein have a pH of about 2.0 to about 8.5. According to one embodiment, the formulations described herein are formulated for transdermal, subcutaneous or topical administration.

In another further aspect of the method or use, the formulation is administered on a daily dosing schedule.

Also described herein are kits, wherein the kit comprises a formulation described herein and instructions for administering to a subject or contacting a biological sample with the formulation.

Definitions

All terms used herein are intended to have their ordinary meaning in the art unless otherwise provided. All concentrations are in terms of percentage by weight of the specified component relative to the entire weight of the topical composition, unless otherwise defined.

As used herein, "a" or "an" shall mean one or more. As used herein when used in conjunction with the word "comprising," the words "a" or "an" mean one or more than one. As used herein "another" means at least a second or more.

As used herein, all ranges of numeric values include the endpoints and all possible values disclosed between the disclosed values. The exact values of all half-integral numeric values are also contemplated as specifically disclosed and as limits for all subsets of the disclosed range. For example, a range of from 0.1% to 3% specifically discloses a percentage of 0.1%, 1%, 1.5%, 2.0%, 2.5%, and 3%. Additionally, a range of 0.1 to 3% includes subsets of the original range including from 0.5% to 2.5%, from 1% to 3%, from 0.1% to 2.5%, etc. It is understood that the sum of all weight % of individual components will not exceed 100%.

The terms "improving a cosmetic skin condition", "improving a skin condition", or "treating a skin condition" include treating a cosmetic skin condition or therapeutically treating a skin condition and may involve at least one of the following benefits: improving moisture retention, reducing skin epithelial cell barrier permeability, thickening of skin (increasing the depth of the skin epithelial layer), restoring skin elasticity, preventing loss of skin elasticity, reducing skin cell flaking, improving skin texture to be smoother, reducing physical manifestations of lines or wrinkles (as determined by, e.g., visual appearance or touch perception) and any combination thereof.

The skin comprises three distinct layers: the stratum corneum (the outermost layer), the epidermis, and the dermis.

The term "barrier integrity of skin cells", as used herein, refers to the ability of the epidermis and particularly the stratum corneum (SC) to function as a selective permeability barrier, which limits transcutaneous evaporative water loss and permits survival in desiccating external environments. The SC is a multilayered tissue composed of flattened, anucleate corneocytes, surrounded by multiple planar lamellae sheets, enriched in ceramides, cholesterol, and free fatty acids (FFA) that hold the entire matrix together. These components, together with tight junction proteins and antimicrobial peptides, contribute to the ability of the skin to act as a permeability barrier. Tight junction proteins contribute to the intercellular adhesive interface, which essentially serves as a seal between cells. Unregulated intercellular leakage from the outermost layer of the skin may, for example, result in loss of water from inner layers of the skin. Barrier integrity may be measured using a variety of assays, including: transepidermal water loss (TEWL) on the skin's surface (in situ); transepithelial/transendothelial electrical resistance (TEER) is also widely accepted as a quantitative technique to measure the integrity of tight junction dynamics in cell culture models of endothelial and epithelial monolayers; techniques that monitor diffusion of dyes (X-Gal or Lucifer Yellow, Toluidine Blue) through the upper epidermis are also used for skin explants and/or in situ skin; 2D or 3D keratinocyte cell cultures are used to assess epidermal differentiation processes that are directly related to the skin barrier permeability; upregulation of proteins that promote skin barrier function and/or downregulation of genes that impair skin barrier function; and immunohistochemistry, microscopical examination and/or other imaging techniques.

The term "improving", when used with respect to improving "barrier integrity of skin cells", refers to increasing the skin's permeability barrier, for example, by increasing the strength of adhesion between skin cells as reflected by an increased ability of the intercellular adhesive interface to prevent unregulated leakage between cells. Assays such as those described with respect to barrier integrity may be used to detect an increase in barrier integrity. The term "improving" may be used to describe an increase equal to or greater than 1%, 2%, 5%, 10%, 15%, 20%, 25%, 30%, 35%, 40%, 45%, 50%, 55%, 60%, 65%, 70%, 75%, 80%, 85%, 90%, 95%, 97%, 98%, 99%, or 100% relative to a starting point measurement prior to contact with an amino acid formulation described herein.

The term "maintaining", when used with respect to maintaining "barrier integrity of skin cells", refers to preserving the strength of the skin's permeability barrier, for example, by preserving the strength of adhesion between skin cells as reflected by the ability of the intercellular adhesive interface to prevent unregulated leakage between cells. With respect to maintaining "barrier integrity of skin cells", measurements can be made to determine baseline strength of intercellular adhesion in, e.g., healthy skin so as to establish a level of intercellular adhesion that is the desired objective to maintain. Samples of the healthy skin can then be exposed to stressors, such as, for example, airborne pollution (e.g., cigarette smoke, noxious fumes, airborne irritants) or physical stressors (e.g., abrasion, harsh detergents, or chemicals) in the presence or absence of a formulation described herein. Amino acid formulations described herein that at least in part prevent a reduction in intercellular adhesion even when challenged with a stressor would be characterized as having the ability to maintain barrier integrity to the degree determined. In such a context, the term "maintaining" may be used to describe preservation of baseline intercellular strength at 100% pre-stressor levels, or equal to or greater than 99%, 98%, 97%, 95%, 90%, 85%, 80%, 75%, 70%, 65%, 60%, 55%, 50%, 45%, 40%, 35%, 30%, 25%, 20%, 15%, 10%, 5%, 2%, or 1% pre-stressor levels due to the presence of an amino acid formulation described herein which counteracts the negative impact of such a stressor.

The term "topical application," as used herein, means to apply or spread the formulations described herein onto the surface of the epidermis tissue.

The term "dermatologically-acceptable," as used herein, means that the formulations or components thereof so described are suitable for use in contact with mammalian epidermal tissue without undue toxicity, incompatibility, instability, allergic response, and the like.

The term "therapeutically effective amount," as used herein, refers to an amount of a compound or formulation sufficient to induce a positive benefit, an improvement in the appearance and/or texture of the skin, where in some embodiments the positive benefit of an amino acid treated skin describes an increase equal to or greater than 1%, 2%, 5%, 10%, 15%, 20%, 25%, 30%, 35%, 40%, 45%, 50%, 55%, 60%, 65%, 70%, 75%, 80%, 85%, 90%, 95%, 97%, 98%, 99%, or 100% relative to a starting point measurement prior to contact with an amino acid formulation described herein; 1 fold or greater (e.g., 3, 5, 7, 9, 11, 13, 15, 17, 19, 21, 23, 25, 27, 29, 31, 33, 35, 37, 39, 41); 40 fold or less (e.g., 38, 36, 34, 32, 30, 28, 26, 24, 22, 20, 18, 16, 14, 12, 10, 8, 6, 4, 2, 0.8, 0.6); or 1-40 fold (e.g., 2-39; 3-38; 4-37; 5-36; 6-35; 7-34; 8-33; 9-32; 10-31; 11-30; 12-29; 13-28; 14-27; 15-26; 16-25; 17-24; 18-23; 19-22; 20-21) better than amino acid untreated skin. In accordance with the present disclosure, a therapeutically effective amount is an amount of a combination of free amino acids, either alone or in combination with other agents, that regulates and/or improves the skin physically and/or visually.

The term "amelioration" or any grammatical variation thereof (e.g., ameliorate, ameliorating, and amelioration etc.), as used herein, includes, but is not limited to, delaying the onset, or reducing the severity of a disease or condition. Amelioration, as used herein, does not require the complete absence of symptoms.

The terms "effective amount" or "significant amount" as used herein, refers to an amount that is capable of treating or ameliorating a disease, condition, or disorder, or is otherwise capable of producing an intended therapeutic effect.

The term "health functional food" refers to a food prepared or processed into tablet, capsule, powder, granule, liquid, pill, or any other form using raw materials or ingredients with useful functions for the human body.

The term "functional" means a useful effect for human health, such as structural or functional regulation of nutrients, the immune system, inflammation, fluid balance, physiological action, or the like.

The term "carrier" refers to a diluent, adjuvant, excipient, or vehicle with which the compound is administered. Examples of suitable pharmaceutical carriers are described in "Remington's Pharmaceutical Sciences" (23rd edition) by E. W. Martin, which is incorporated herein by reference.

The term "treatment" or any grammatical variation thereof (e.g., treat, treating, and treatment etc.), as used herein, includes but is not limited to, alleviating a symptom of a disease, condition, or disorder; and/or reducing, suppressing, inhibiting, lessening, or affecting the progression, severity, and/or scope of a disease, condition, or disorder.

The term "consisting essentially of," as used herein, limits the scope of the ingredients and steps to the specified materials or steps and those that do not materially affect the basic and novel characteristic(s) of the present invention, i.e., formulations and methods for promoting at least one of skin integrity, function, texture, or appearance, or any combination thereof.

The term "amino acid" encompasses all known amino acids comprising an amine ($-NH_2$) functional group, a carboxyl ($-COOH$) functional group, and/or a side chain ("R") group specific to each amino acid. "Amino acids" encompasses the 21 amino acids encoded by the human genome (i.e., proteinogenic amino acids), amino acids encoded or produced by bacteria or single-celled organisms, and naturally derived amino acids. For the purposes of this disclosure, the conjugate acid form of amino acids with basic side chains (arginine, lysine, and histidine) and the conjugate base form of amino acids with acidic side chains (aspartic acid and glutamic acid) are essentially the same, unless otherwise noted. "Amino acids" also encompass derivatives and analogs thereof that retain substantially the same activity in terms of improving barrier integrity of skin cells in, for example, a TEER or TEWL assay as described above. The derivatives and analogs may be, for example, enantiomers, and include both the D- and L-forms of the amino acids. The derivatives and analogs may be derivatives of "natural" or "non-natural" amino acids (e.g., f-amino acids, homo-amino acids, proline derivatives, pyruvic acid derivatives, 3-substituted alanine derivatives, glycine derivatives, ring-substituted cysteine derivatives, ring-substituted phenylalanine derivatives, linear core amino acids, and N-methyl amino acids), for example, selenocysteine, pyrrolysine, iodocysteine, norleucine, or norvaline. The derivatives and analogs may comprise a protecting group ($\alpha$-amino group, $\alpha$-carboxylic acid group, or suitable R group, wherein R contains a NH2, OH, SH, COOH or other reactive functionality). Other amino acid derivatives include, but are not limited to, those that are synthesized by, for example, acylation, methylation, glycosylation, and/or halogenation of the amino acid. These include, for example, f-methyl amino acids, C-methyl amino acids, and N-methyl amino acids. The amino acids described herein may be present as free amino acids. The term "free amino acid" refers to an amino acid that is not part of a peptide or polypeptide (e.g., is not connected to another amino acid through a peptide bond). A free amino acid is free in solution (as opposed to being linked to at least one other amino acid via, for example, a dipeptide bond), but may be associated with a salt or other component in solution.

As used herein, the term "salt" refers to any and all salts and encompasses pharmaceutically acceptable salts. For example, embodiments of the disclosure are directed to amino acids or salts thereof.

Exemplary salts for inclusion in a formulation described herein include sodium chloride, potassium chloride, calcium chloride, magnesium chloride, or tri-sodium citrate, sodium bicarbonate, sodium gluconate phosphate buffers using mono, di or tri-sodium phosphate or any combination thereof.

Exemplary diluents include calcium carbonate, sodium carbonate, calcium phosphate, dicalcium phosphate, calcium sulfate, calcium hydrogen phosphate, cellulose, microcrystalline cellulose, kaolin, sodium chloride, and mixtures thereof.

Pharmaceutically acceptable excipients used in the manufacture of pharmaceutical formulations described herein include inert diluents, dispersing and/or granulating agents, surface active agents and/or an emulsifier or a phospholipid, where in some embodiments, phospholipids are used as an emulsifier (e.g., lecithin or phosphatidylcholine), disintegrating agents, binding agents, preservatives, buffering agents, lubricating agents, and/or oils. Excipients such as cocoa butter and suppository waxes, coloring agents, coating agents, and perfuming agents may also be present in the composition.

Abbreviations used: Amino acids: Ala—alanine, Arg—arginine, Cys—cysteine, Gln—glutamine, Gly—glycine, His—histidine, Ile—isoleucine, Ser—serine, Thr—threonine, Tyr—tyrosine, Val—valine. Genes/products: CPT2—carnitine palmitoyltransferase 2; CASP8-caspase 8; EGF—epidermal growth factor; FGF—fibroblast growth factor; MK167—marker of proliferation Ki-67; PDGF-platelet-derived growth factor; PPARs—peroxisome proliferator-activated receptors; SMAD—an acronym from the fusion of *Caenorhabditis elegans* Sma genes and the *Drosophila* Mad, Mothers against decapentaplegic; TGFB1—transforming grown factor beta 1; TGM—transglutaminase, TNFRSF10D-TNF Receptor Superfamily Member 10d; Other: FAA—free amino acids, NMF—natural moisturizing factor, NHEK—normal human epidermal keratinocytes, pPCR—quantitative polymerase chain reaction; TJ—tight junctions, SC—stratum corneum.

BRIEF DESCRIPTION OF FIGURES

FIG. 2 presents a Table listing combinations of amino acids. Amino acids in combos #1, 2, 4, 6 and 7 were used at a concentration of 4 mM for each amino acid. Amino acids in combos #3 and #4 were used at the lower indicated concentrations (in mM) due to toxic effects detected at concentrations 4 mM.

FIG. 3 presents a Table showing a transcript analysis of skin barrier integrity marker genes in primary keratinocytes. Differentiation Genes are designated with *, whereas Proliferation Genes are designated with +. EGF contributes to both differentiation and proliferation. Scoring system developed: # of points given to relative expression. (Average relative expression >1.5 (50% Increase); Untreated=1).

FIG. 4 presents a Table showing a transcript analysis of skin barrier integrity marker genes in primary keratinocytes. Differentiation Genes are designated with *, whereas Proliferation Genes are designated with +. EGF contributes to both differentiation and proliferation. Scoring system developed: # of points given to relative expression. (Average relative expression >1.5 (50% Increase); Untreated=1) (n=5).

FIG. 7A shows EGF expression of 4GAA alone (4 mM); BSW 1% alone; the combination of 4GAA 4 mM and BSW 1% with Donor O cells. FIG. 7B illustrates EGF expression of 4GAA alone (1 mM); BSW 0.25% alone; the combination of 4GAA 1 mM and BSW 0.25% with Donor O cells. FIG. 7C shows EGF expression of 4GAA alone (4 mM); BSW 0.5% alone; the combination of 4GAA 4 mM and BSW 0.5% with Donor G cells. FIG. 7D presents EGF expression of 4GAA alone (1 mM); BSW 0.25% alone; the combination of 4GAA 1 mM and BSW 0.25% with Donor G keratinocyte cells. * p value=0.05; ** p value=0.01. "CTR" or "CTR untr" is untreated control. n=3

FIGS. 14A-14C show the average fold change of EGF mRNA comparing the 4 amino acid combination (Ala, Gln, Gly, Ser; 4GAA; 4 mM), and *Boswellia* plant extract combination (BSXL; 0.5 w/w %), alone or in combination with Donor A, Donor G, and Donor T keratinocytes. The data are shown in tabular form (FIG. 14A (Donor A (n=1), Donor G (n=3), and Donor T (n=2)); FIG. 14B (Donor A (n=3), Donor G (n=9), and Donor T (n=6)) and FIG. 14B data represented in graphical form (FIG. 14C). FIG. 14C shows CTR; 4GAA; BSXL; 4GAA+BSXL combination: Donor G (top 3), Donor T (center), Donor A (bottom 3). * p<0.05 versus untreated CTR control; #p<0.05 versus 4GAA and BSXL. Repeated measures analysis of variance (RMANOVA) with Tukey post-hoc was used for analysis.

FIG. 15A shows the TEWL change from baseline-Day 1 immediately after tape-stripping and Days 2, 3, and 5 (X-axis) are after two treatments per day of test materials. FIG. 15B demonstrates the relative TEWL increase after tape-stripping where all values are normalized to the baseline-Day 1 which represents TEWL immediately after tape-stripping. Active (left column); Placebo (right column). Mean+/−95% Confidence Interval (CI).

DETAILED DESCRIPTION

Figure 1:
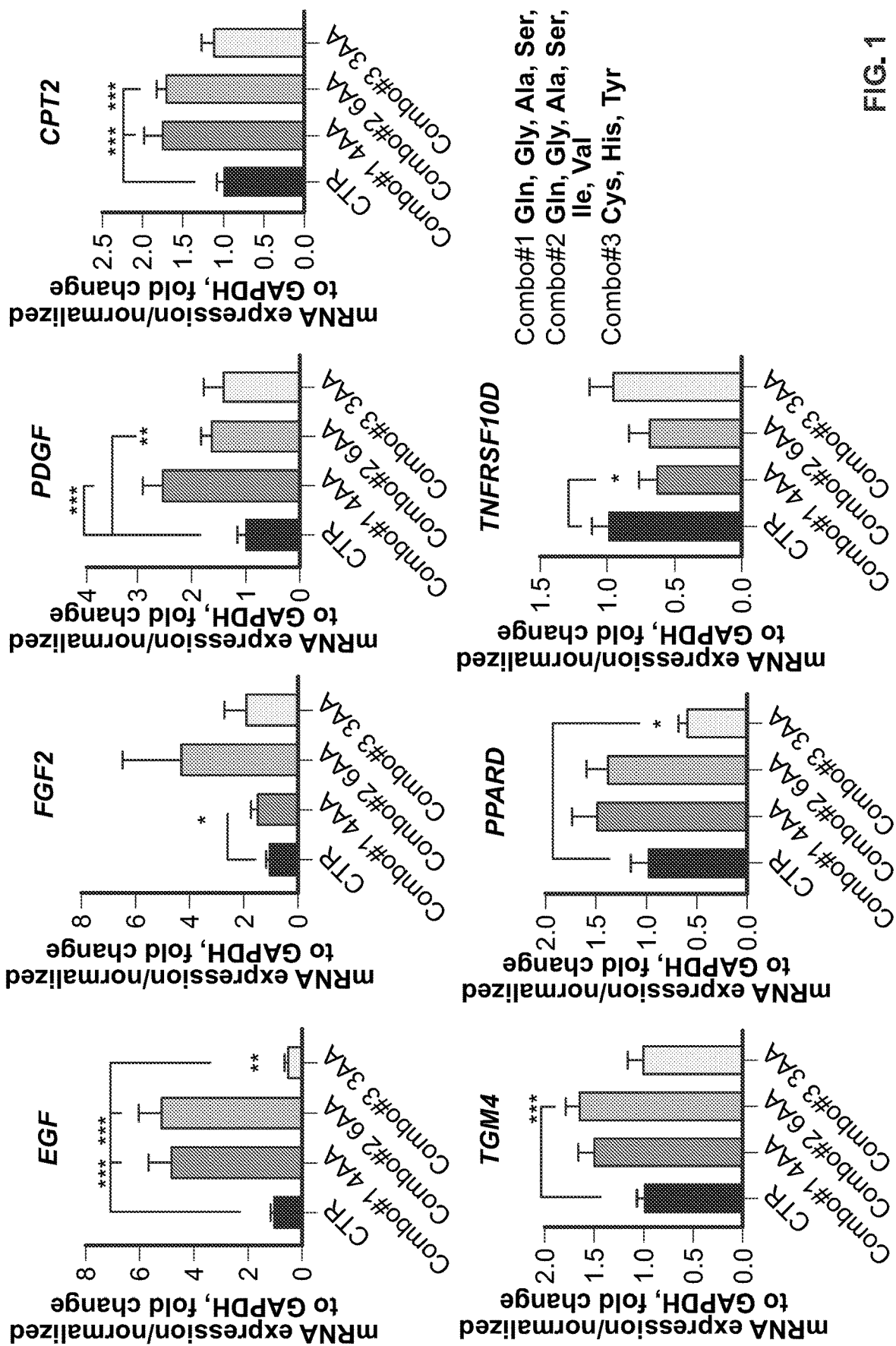
FIG. 1 shows the effect of treatment of amino acid combinations on mRNA expression of barrier marker genes in differentiated normal human epidermal keratinocytes (NHEK) cells of 5 donors. Treatment time—4 h. All graphed data show mean±SE. *: $p<0.05$, :$p<0.01$, *:$p<0.001$ compared to untreated cells (CTR) in two-tailed t-test. Data from two independent experiments. Exemplary barrier marker genes examined as follows: Epidermal growth factor (EGF); fibroblast growth factor 2 (FGF2); platelet derived growth factor (PDGF); Carnitine Palmitoyltransferase 2 (CPT2); Transglutaminase 4 (TGM4); Peroxisome Proliferator Activated Receptor Delta (PPARD); TNF Receptor Superfamily Member 10d (TNFRSF10D).
Figure 5:
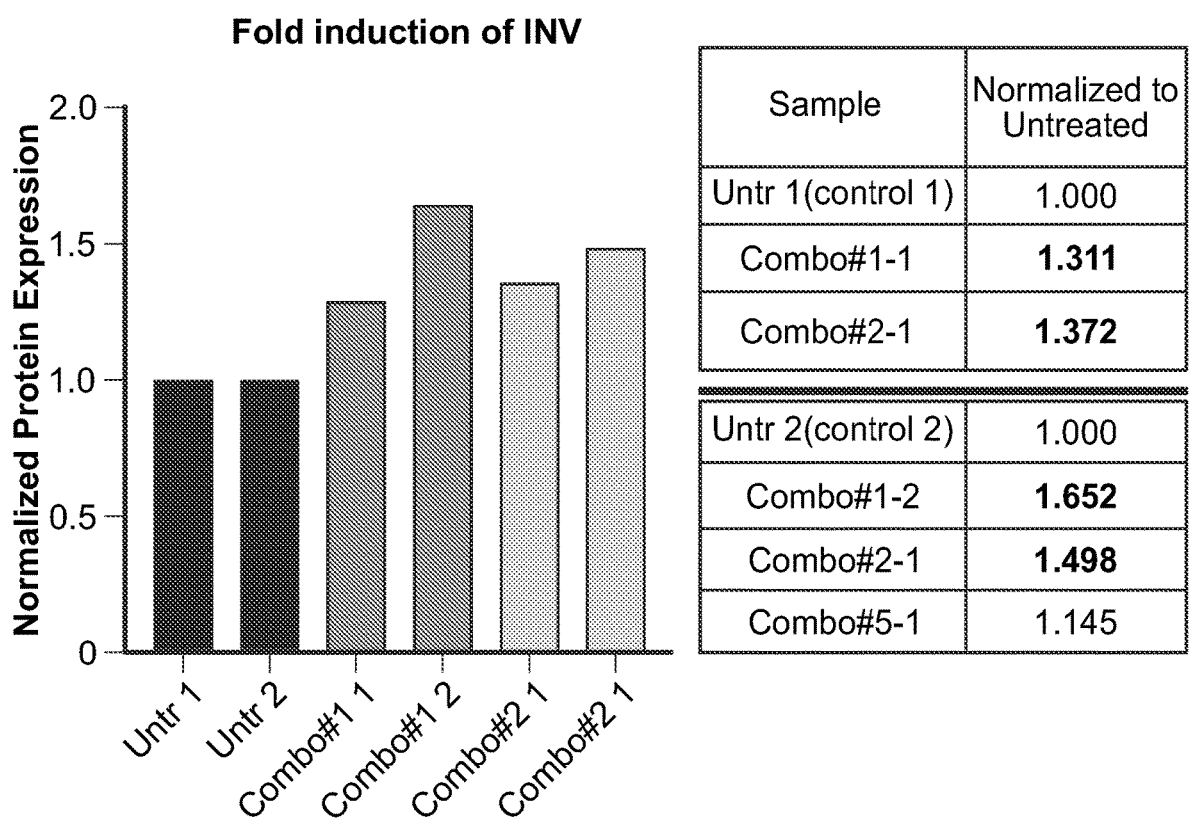
FIG. 5 shows quantification of Western Blot analysis of involucrin (INV) expression at 24 h of treatment. Combo #1: Gln, Gly, Ala, Ser; Combo #2: Gln, Gly, Ala, Ser, Ile, Val; Combo #5: Cys, His, Leu, Asp. Quantitative analysis of involucrin expression determined based on results from two donor samples.
Figure 6:
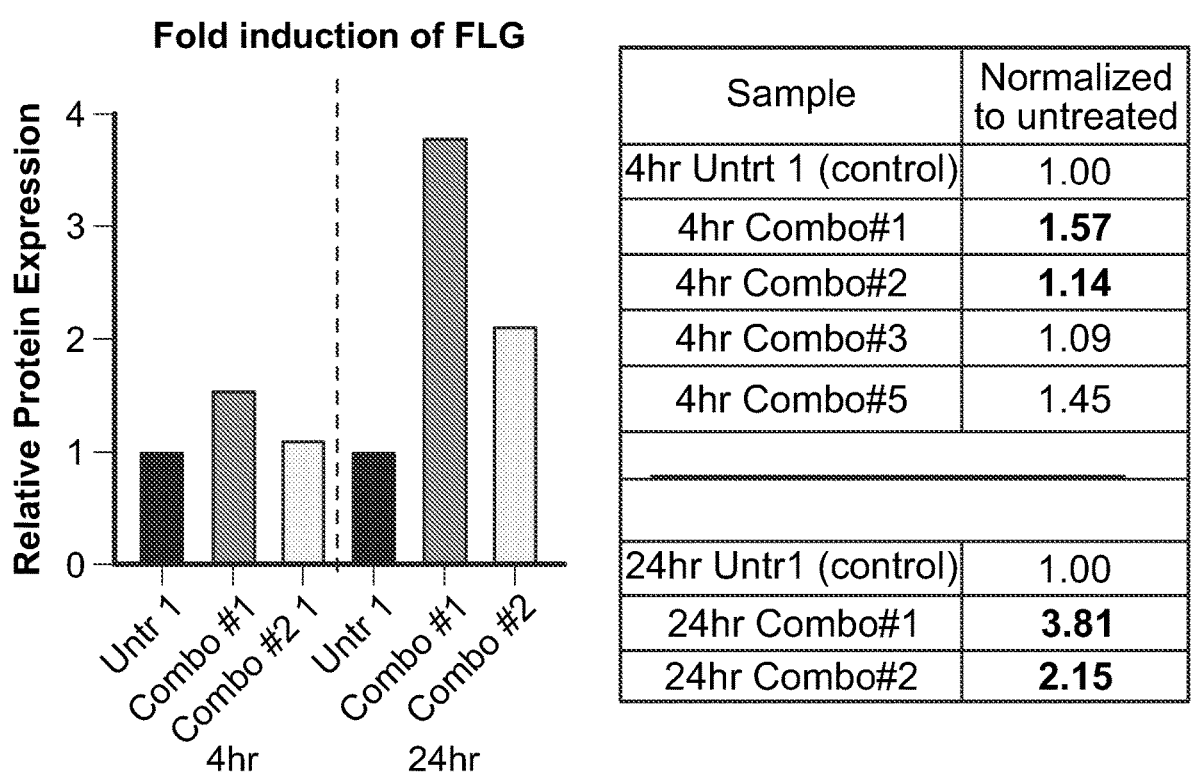
FIG. 6 shows quantification of Western Blot analysis of filaggrin (FLG) expression at 4 and 24 h of treatment. Combo #1: Gln, Gly, Ala, Ser; Combo #2: Gln, Gly, Ala, Ser, Ile, Val; Combo #3: Cys, His, Tyr; Combo #5: Cys, His, Leu, Asp.

Detailed embodiments of the present disclosure are disclosed herein; however, it is to be understood that the disclosed embodiments are merely illustrative of the disclosure that may be embodied in various forms. In addition, each of the examples given in connection with the various embodiments of the disclosure is intended to be illustrative, and not restrictive.

The skin acts as a physical barrier that separates an organism from its surrounding environment, but also serves as an interactive interface with that environment. The skin comprises three distinct layers: the stratum corneum, the epidermis, and the dermis. The stratum corneum (the outermost layer) comprises keratinized cells and provides a physical barrier with the external environment. Environmental stressors vary based, for example, on climate and/or lifestyle and may include xenobiotics, UV radiation, pollution (e.g., cigarette smoke or engine exhaust), and pathogens. In addition to acting as a shield that protects the lower layers of the skin from such environmental insults, the stratum corneum also reduces water loss from the skin. Skin keratinocytes are connected via tight junction (TJ) proteins, such as zona occludins (ZOs). TJ proteins play a significant role in barrier function, as well as contributing to keratinocyte proliferation and differentiation. Barrier function integrity serves as a major feature of the skin that prevents excessive water loss from the skin, thereby maintaining healthy skin.

Skin barrier dysregulation is implicated in a variety of common skin diseases like atopic dermatitis, psoriasis, and ichthyosis. Skin barrier dysregulation also contributes to xerosis cutis (dry skin), a common dermatological disorder, which is exacerbated by low humidity, repeated washing, and exposure to harsh chemicals. Such external stressors promote water loss from the skin. Dry skin may lead to or be accompanied by itching and/or skin irritation. Dry skin may be considered a symptom of decreasing barrier function of the skin. Dry skin is also a common feature of aging skin.

Optimal management of many skin diseases, conditions, or disorders includes appropriate skin care. Incorporation of a well-designed moisturizer/barrier repair formulation can help reduce disease-associated signs and symptoms, thereby ameliorating the disease. Effective moisturizer/barrier repair formulations for treating dry skin that enhance skin regeneration and strengthen skin barrier function are described herein. The formulations comprise specific amino acid combinations that confer cosmetic and/or therapeutic benefit in the context of treating a variety of cosmetic skin conditions and skin diseases, conditions, and disorders (for example, xerotic skin).

Described herein are formulations of specific combinations of amino acids for maintaining healthy skin, treating cosmetic skin conditions, and treating skin conditions, disorders, and diseases. In one aspect, described herein are formulations and methods for improving barrier integrity of the skin, promoting cellular proliferation, and/or development. As used herein, reference to "development" can include, for example, migration, maturation, and/or differentiation of skin cells. The disclosure also provides formulations and methods for treating and/or preventing a cosmetic skin condition or a skin condition associated with a disease or disorder of the skin. Such skin conditions include, without limitation, atopic dermatitis, psoriasis, conditions related to aging of the skin, pruritis, eczema, and/or a cosmetic condition. The disclosure also provides formulations and methods for treating a wound or burn.

Atopic Dermatitis (AD), for example, is the most common chronic inflammatory skin disease in people, affecting up to 15 million Americans (17% of children and 6% adults). Despite its high prevalence, effects on quality-of-life, and economic burden, there are still few effective treatments for AD and most have focused generally on inhibiting inflammation. AD is thought to develop in part as consequence of an acquired or genetic defect of the skin's barrier. The epidermis from AD subjects exhibit altered tight junctions (TJ), which was associated with reduced expression of selected TJ components (e.g., claudin). TJs seal the intercellular spaces between epithelial cells and the 'tightness' of this structure is dynamically regulated by endogenous or environmental factors. The regulation of the TJ seal is important for a variety of reasons, including appropriate trafficking patterns of ions, proteins, hydration, and even the penetration of immune cells.

The integrity of the tight junction dynamics between endothelial cells and epithelial cells, which regulates diffusion and maintains homeostasis of organs protected by physiological barriers, may be measured in-vitro using transepithelial/transendothelial electrical resistance (TEER). TEER can be used to identify agents that improve physiological barriers, and that therefore may have a positive impact on conditions associated with elevated levels of permeability of physiological barriers relative to a normal, healthy state. Conditions associated with elevated levels of permeability of physiological barriers include, e.g., atopic dermatitis and xerosis cutis. Results presented herein reveal that specific amino acid combinations improve/enhance barrier integrity of skin cells. Improvements in skin cell barrier integrity are thought to be mediated, at least in part, by tight junction dynamics and reflect reduced permeability of tight junctions. See, for example, FIGS. 1-6.

The subject may be a patient in which improving barrier integrity of the skin is needed. The patient may have this need due to, for example, exposure to chemical or physical irritants, age related predispositions, genetic predispositions, or skin inflammation. In one embodiment, the patient is asymptomatic. The subject can be any animal, including, for example, a human. In addition to humans, the animal may be, for example, mammals, such as rabbits, cattle, horses, sheep, pigs, goats, dogs, and cats.

As indicated above, skin barrier malfunction is implicated in common skin diseases like atopic dermatitis, psoriasis, and ichthyosis and a very common dermatological disorder, xerosis cutis (dry skin). Dry skin is a condition experienced by most people at some point in their lives. Seasonal xerosis is common during the cold, dry winter months, and the frequency of xerosis increases with age. Optimal management of many skin diseases includes appropriate skin care. Incorporation of a well-designed moisturizer/barrier repair formulation into a skin care regimen could contribute to improvement or mitigation of condition- or disease-associated symptoms.

An effective moisturizer/barrier repair formulation for dry xerotic skin that enhances skin's own ability to regenerate, restore and strengthen its own barrier function is desired, wherein the formulation uses an amino acid-based technology. These formulations offer new treatment options for dry scaly skin that benefit a large number of people suffering from same and at risk for developing more serious conditions that arise from unattended dry skin.

Physiologically, amino acids and their derivatives are important elements of the skin, as they are components of the Natural Moisturizing Factor (NMF) in the outermost layer of the skin, the stratum corneum (SC). Free amino acids (FAA) are produced by the hydrolysis of the keratinocyte protein filaggrin, corneodesmosomes, and SC keratins during normal physiological processes of epidermal maturation and terminal differentiation. NMF contributes to maintenance of adequate skin hydration. Some amino acids can effectively bind water and may, therefore, play a role in the regulation of skin hydration. Thus, specific amino acid supplementation to the skin is proposed herein to ensure proper levels of NMF and protein synthesis or production of certain significant amino acid metabolites [pyrrolidone carboxylic acid (PCA) and trans-urocanic acid (t-UCA)] that condition, nourish, and/or replenish the proteins in normal and xerotic skin, as well other skin conditions where the epidermal barrier is impaired.

Without being bound by theory, by delivering specific amino acid combinations to the skin, the skin's innate ability to form a proper barrier might be "fertilized". The problem of how to maintain/restore skin barrier function is solved by developing amino acid formulations that target specific cellular pathways involved in skin barrier function and repair, thereby transforming amino acids from simple building blocks into small molecules capable of triggering signaling pathways that promote skin barrier function.

Results presented herein demonstrate that supplementation with particular amino acid combinations can modulate transcription of key regulators of differentiation and proliferation, such as, e.g., EGF and PDGF genes, in normal primary human keratinocytes. Specific combinations of amino acids that exhibit this functional ability was determined by analyzing their action on skin barrier markers. Notably, specific combinations of certain amino acids exhibit a beneficial effect on skin barrier function (such as Ser, Ala, Gly and Gln), while combinations of other amino acids (such as Cys, His and Tyr) have no effect or even negative effects on skin barrier function. Additional screening assays to identify the most effective combination/s of amino acids for improving barrier integrity of the skin/skin barrier function are performed, tested, and validated in preclinical studies using different skin models and different modes of administration (e.g., systemic and/or topical).

Specific aims include defining efficacious formulations of amino acids that promote skin barrier function (see FIGS. 1-6) and further evaluating and developing such amino acid formulations using 2D monolayer cultures (human differentiated keratinocytes) and 3D models (human epidermal skin equivalents). The effect of media supplementation with several amino acid combinations (e.g., the four core amino acid combination of Ser, Ala, Gly and Gln described above with and without Ile, Trp and/or Arg) on mRNA and protein levels of a panel of skin barrier markers that was identified based on reiterative analyses are determined. See, e.g., EXAMPLE 1.

Briefly, genes and proteins related to epidermal differentiation, proliferation and lipid regulation in skin were iteratively evaluated and weighted with respect to their structural/functional impact on skin barrier integrity. Determination of the panel of markers utilized herein that reflect barrier integrity of the skin was determined by a series of multivariate, iterative analyses. The complexity of the task is underscored by the voluminous array of potential genes that have been implicated in, e.g., barrier function, proliferation, differentiation, and inflammation, each of which biological processes could contribute to some degree in barrier integrity of the skin. Indeed, hundreds of genes have been implicated in these processes. The starting point for determining a suitable panel of markers that reflect barrier integrity of the skin, therefore, offers an indeterminant number of different potential skin barrier marker panels. Choosing a panel from this myriad of options required experimentation using multiple sample sources to avoid sample bias, reiterative analyses studying different endpoints, weighted significance of different genes in the skin barrier marker panel, and careful analysis of all the variables in these analytic approaches. The panel of skin barrier markers chosen to reflect barrier integrity of the skin is the result of the above analytical approach and thus, was determined following a mathematical, biological approach involving experimental results, statistical analyses thereof, and algorithmic analyses of all inputs collected.

Once the skin barrier marker panel was identified, a scoring system by which to evaluate different amino acid combinations under consideration was developed. The scoring system was developed to address the numerous variables arising from the experimental results. Such variables included, for example, degree of transcriptional upregulation, the number of different genes up- or down-regulated in response to an amino acid combination examined, and variation in readout observed among different sample sources. See, e.g., FIGS. 3 and 4.

Specific aims also include evaluating the effect of topical administration of the most promising amino acid formulations on epithelial barrier markers in in vitro and ex vivo models of normal and compromised skin. Briefly, amino acid formulations identified based on their superior ability to improve barrier function are used for topical treatment of normal and compromised epidermal skin equivalents and normal skin histocultures (skin explants). To generate an inflammatory skin phenotype, immature epidermal skin equivalents are pretreated with T-helper cell (Th-2)-derived cytokines in combination with TNFα and skin explants are delipidated with a tape-strip approach. The effect of treatment on the barrier function and integrity of tight junction (TJ) dynamics are investigated through a combination of gene expression, biochemical, morphological, and functional analyses (e.g., transepithelial/transendothelial electrical resistance (TEER) technique). See, e.g., EXAMPLES 4 and 5.

The identification of effective amino acid formulations and use thereof in barrier repair formulations/moisturizers, therefore, provides a solution to the problem of how to maintain and restore healthy skin as people age and under conditions of duress and/or disease. Formulations identified herein, therefore, satisfy a long-sought need for scientifically validated barrier repair formulations/moisturizers that address the underlying biological causes of skin conditions (e.g., xerosis cutis), rather than just the symptoms thereof. Proof-of-concept studies are conducted on human subjects using the most promising amino acid-based cosmetic formulations.

Formulations and Methods for Treating a Cosmetic Skin Condition or Other Skin Conditions Dry, sensitive, xerotic skin [xerosis cutis (also referred to as xeroderma, dry skin, asteatosis)] is the most common dermatological disorder impacting approximately 50% of the world's population. The severity of this disorder increases with age. It affects patients' quality of life and, due to the impaired skin barrier, is a risk factor for the development of atopic or allergic dermatitis and other skin diseases.

Dry skin is associated with the development of cutaneous fissures and pressure-related ulcers that could be avoided through adequate skin care. Many skin care products used for the management of dry skin mimic the various components of the skin barrier. They are designed to incorporate lipophilic (lipid-replenishing, film-forming) and hydrophilic (remoisturizing) ingredients into the skin. Such products can improve the hydration of the SC, thereby dampening inflammation, but they do not address the underlying biochemical abnormalities in dry skin. Moreover, many skin care products sold on the market provide no scientifically proven benefits.

A need, therefore, exists for effective topical skin care for xerosis cutis that not only mimics the skin barrier components but enhances the skin's own ability to maintain and/or repair the strength of its barrier. A protective barrier so formed restores, at least in part, the structural and functional properties of healthy skin. Topical skin care products that enhance the skin's ability to maintain and/or repair barrier integrity, therefore, address the underlying causes of xerosis cutis, rather than just its symptoms. Formulations directed to addressing this objective were developed.

Xerotic aged skin, for example, has decreased levels of profilaggrin and filaggrin—major sources of free amino acids (FAA) in SC—so decreased levels of these proteins lead, in turn, to a decreased pool of available FAA. Results presented herein show that specific amino acid combinations described herein supplement the age-depleted FAA pool with targeted specificity. Results presented herein further demonstrate that specific combinations of amino acids synergize to confer benefit to structural/functional properties of skin barrier integrity and surprisingly, that certain amino acids can even be detrimental to skin barrier integrity.

Data presented herein also demonstrate that treatment with specific amino acid combinations upregulates a panel of skin barrier marker genes in normal human keratinocytes (e.g., EGF, PDGF, CPT2, TGM4) that play important roles in skin development and homeostasis.

The mechanism(s) whereby amino acids strengthen barrier integrity of the skin, with focused attention on their effect on TJs, and/or improve skin barrier repair, are described here. To the best of their knowledge, these mechanisms have not been previously investigated in the skin with scientific rigor.

As emphasized above, amino acids do not have equal beneficial effects on skin barrier integrity. Indeed, some amino acids, alone or in combination, are contraindicated with respect to skin barrier integrity. Therefore, a targeted approach is needed to identify the most effective amino acids for promoting skin barrier health. A new scientifically proven amino acid-based technology targeting compromised epithelial skin is proposed herein to provide a better solution for people who suffer from dry and sensitive skin.

Accordingly, in certain embodiments, the present disclosure provides methods for treating and/or preventing a skin condition in a subject in need thereof, the method comprising administering to the subject a formulation described herein. In certain aspects, the skin condition is dry skin, atopic dermatitis, dermatitis, psoriasis, aging of skin, a condition related to the aging of skin (e.g., wrinkles, loss of suppleness, increase is roughness), pruritus, or eczema. In further aspects, the skin condition is a cosmetic skin condition.

In certain aspects, the formulation for treating and/or preventing a cosmetic skin condition or treating and/or preventing a skin condition comprises: as free amino acids, a therapeutically effective amount of a combination of glutamine, glycine, alanine, and serine; and optionally, a therapeutically effective amount of at least one additional free amino acid of valine, isoleucine, arginine, threonine, or tryptophan, or any combination thereof; wherein the therapeutically effective amount of the combination of glutamine, glycine, alanine, and serine and the therapeutically effective amount of the at least one additional free amino acid improves barrier integrity of skin cells; and optionally, a dermatologically acceptable carrier; wherein the formulation improves barrier integrity of the skin. In a particular embodiment, the free amino acids comprise, consist essentially of, or consist of glutamine, glycine, alanine, serine, and valine; and at least one additional amino acid of isoleucine, arginine, threonine, or tryptophan, or any combination thereof. In a more particular embodiment, the free amino acids comprise, consist essentially of, or consist of glutamine, glycine, alanine, serine, valine, and isoleucine; and at least one additional amino acid of arginine, or threonine, or any combination thereof. In more particular embodiments, the free amino acids comprise, consist essentially of, or consist of glutamine, glycine, alanine, serine, and valine; the free amino acids comprise, consist essentially of, or consist of glutamine, glycine, alanine, serine, valine, and isoleucine; the free amino acids comprise, consist essentially of, or consist of glutamine, glycine, alanine, serine, valine, isoleucine, and arginine; the free amino acids comprise, consist essentially of, or consist of glutamine, glycine, alanine, serine, valine, isoleucine, and threonine; the free amino acids comprise, consist essentially of, or consist of glutamine, glycine, alanine, and serine; and at least one additional amino acid of isoleucine, arginine, threonine, or tryptophan, or any combination thereof; the free amino acids comprise, consist essentially of, or consist of glutamine, glycine, alanine, serine, and isoleucine; the free amino acids comprise, consist essentially of, or consist of glutamine, glycine, alanine, serine, and arginine; the free amino acids comprise, consist essentially of, or consist of glutamine, glycine, alanine, serine, and threonine; the free amino acids comprise, consist essentially of, or consist of glutamine, glycine, alanine, serine, and tryptophan; the free amino acids comprise, consist essentially of, or consist of glutamine, glycine, alanine, serine, and isoleucine; and at least one additional amino acid of arginine, or threonine, or tryptophan, or any combination thereof; the free amino acids comprise, consist essentially of, or consist of glutamine, glycine, alanine, serine, isoleucine, and arginine; the free amino acids comprise, consist essentially of, or consist of glutamine, glycine, alanine, serine, isoleucine, and threonine; the free amino acids comprise, consist essentially of, or consist of glutamine, glycine, alanine, serine, isoleucine, and tryptophan; the free amino acids comprise, consist essentially of, or consist of glutamine, glycine, alanine, serine, isoleucine, arginine, and threonine; the free amino acids comprise, consist essentially of, or consist of glutamine, glycine, alanine, serine, isoleucine, arginine, and tryptophan; the free amino acids comprise, consist essentially of, or consist of glutamine, glycine, alanine, serine, isoleucine, threonine, and tryptophan; the free amino acids comprise, consist essentially of, or consist of glutamine, glycine, alanine, serine, isoleucine, arginine, threonine, and tryptophan; the free amino acids comprise, consist essentially of, or consist of glutamine, glycine, alanine, serine, and arginine; and at least one additional amino acid of isoleucine, threonine, or tryptophan, or any combination thereof; the free amino acids comprise, consist essentially of, or consist of glutamine, glycine, alanine, serine, and threonine; and at least one additional amino acid of isoleucine, arginine, or tryptophan, or any combination thereof; or the free amino acids comprise, consist essentially of, or consist of glutamine, glycine, alanine, serine, and tryptophan; and at least one additional amino acid of isoleucine, arginine, or threonine, or any combination thereof.

In one embodiment, the formulation optionally comprises, for example, pharmaceutically acceptable carriers, adjuvants, other active agents, and additives (e.g., sugars, electrolytes, vitamins, minerals, etc.).

In some embodiments of formulations described herein, wherein, if present, free amino acids of cysteine are present at a concentration of equal to or less than 1 mM; if present, free amino acids of histidine are present at a concentration of equal to or less than 0.5 mM; if present, free amino acids of tyrosine are present at a concentration of equal to or less than 1 mM; if present, free amino acids of leucine are present at a concentration of equal to or less than 4 mM; or if present, free amino acids of aspartic acid are present at a concentration of equal to or less than 2 mM; or any combination thereof. In some embodiments of the formulation, the formulation does not comprise free amino acids of cysteine, histidine, tyrosine, leucine, aspartic acid, taurate, taurine, or glutamate, or any combination thereof.

In some embodiments of formulations described herein, wherein, if present, free amino acids of alanine are present at a concentration of equal to or less than 4% (e.g., 3.8, 3.6, 3.4, 3.2, 2.8, 2.6, 2.4, 2.2, 2, 1.8, 1.6, 1.4, 1.2, 0.8, 0.6, 0.4, 0.2, 0.18, 0.16, 0.14, 0.12, 0.08, 0.06, 0.058, 0.056, 0.054, 0.052, 0.05, 0.048, 0.046, 0.044, 0.042, 0.04, 0.038, 0.036, 0.034, 0.032, 0.03, 0.02, 0.018, 0.016, 0.014, 0.012); 0.01% or greater (e.g., 0.011, 0.013, 0.015, 0.017, 0.019, 0.021, 0.023, 0.025, 0.027, 0.029, 0.03, 0.031, 0.033, 0.035, 0.037, 0.039, 0.041, 0.043, 0.045, 0.047, 0.049, 0.05, 0.051, 0.053, 0.055, 0.057, 0.059, 0.07, 0.09, 0.1, 0.11, 0.13, 0.15, 0.17, 0.19, 0.3, 0.5, 0.7, 0.9, 1, 1.1, 1.3, 1.5, 1.7, 1.9, 2.1, 2.3, 2.5, 2.7, 2.9, 3, 3.1, 3.3, 3.5, 2.7, 2.9, 3, 3.1, 3.3, 3.5, 3.7, 3.9, 4.1, 4.3, 4.5, 4.7, 4.9, 5); if present, free amino acids of glutamine are present at a concentration of equal to or less than 4% (e.g., 3.8, 3.6, 3.4, 3.2, 2.8, 2.6, 2.4, 2.2, 2, 1.8, 1.6, 1.4, 1.2, 0.8, 0.6, 0.4, 0.2, 0.18, 0.16, 0.14, 0.12, 0.08, 0.06, 0.058, 0.056, 0.054, 0.052, 0.05, 0.048, 0.046, 0.044, 0.042, 0.04, 0.038, 0.036, 0.034, 0.032, 0.03, 0.02, 0.018, 0.016, 0.014, 0.012); 0.01% or greater (e.g., 0.011, 0.013, 0.015, 0.017, 0.019, 0.021, 0.023, 0.025, 0.027, 0.029, 0.03, 0.031, 0.033, 0.035, 0.037, 0.039, 0.041, 0.043, 0.045, 0.047, 0.049, 0.05, 0.051, 0.053, 0.055, 0.057, 0.059, 0.07, 0.09, 0.1, 0.11, 0.13, 0.15, 0.17, 0.19, 0.3, 0.5, 0.7, 0.9, 1, 1.1, 1.3, 1.5, 1.7, 1.9, 2.1, 2.3, 2.5, 2.7, 2.9, 3, 3.1, 3.3, 3.5, 3.7, 3.9, 4.1, 4.3, 4.5, 4.7, 4.9, 5); if present, free amino acids of glycine are present at a concentration of equal to or less than 4% (e.g., 3.8, 3.6, 3.4, 3.2, 2.8, 2.6, 2.4, 2.2, 2, 1.8, 1.6, 1.4, 1.2, 0.8, 0.6, 0.4, 0.2, 0.18, 0.16, 0.14, 0.12, 0.08, 0.06, 0.058, 0.056, 0.054, 0.052, 0.05, 0.048, 0.046, 0.044, 0.042, 0.04, 0.038, 0.036, 0.034, 0.032, 0.03, 0.02, 0.018, 0.016, 0.014, 0.012); 0.01% or greater (e.g., 0.011, 0.013, 0.015, 0.017, 0.019, 0.021, 0.023, 0.025, 0.027, 0.029, 0.03, 0.031, 0.033, 0.035, 0.037, 0.039, 0.041, 0.043, 0.045, 0.047, 0.049, 0.05, 0.051, 0.053, 0.055, 0.057, 0.059, 0.07, 0.09, 0.1, 0.11, 0.13, 0.15, 0.17, 0.19, 0.3, 0.5, 0.7, 0.9, 1, 1.1, 1.3, 1.5, 1.7, 1.9, 2.1, 2.3, 2.5, 2.7, 2.9, 3, 3.1, 3.3, 3.5, 3.7, 3.9, 4.1, 4.3, 4.5, 4.7, 4.9, 5); if present, free amino acids of serine are present at a concentration of equal to or less than 4% (e.g., 3.8, 3.6, 3.4, 3.2, 2.8, 2.6, 2.4, 2.2, 2, 1.8, 1.6, 1.4, 1.2, 0.8, 0.6, 0.4, 0.2, 0.18, 0.16, 0.14, 0.12, 0.08, 0.06, 0.058, 0.056, 0.054, 0.052, 0.05, 0.048, 0.046, 0.044, 0.042, 0.04, 0.038, 0.036, 0.034, 0.032, 0.03, 0.02, 0.018, 0.016, 0.014, 0.012); 0.01% or greater (e.g., 0.011, 0.013, 0.015, 0.017, 0.019, 0.021, 0.023, 0.025, 0.027, 0.029, 0.03, 0.031, 0.033, 0.035, 0.037, 0.039, 0.041, 0.043, 0.045, 0.047, 0.049, 0.05, 0.051, 0.053, 0.055, 0.057, 0.059, 0.07, 0.09, 0.1, 0.11, 0.13, 0.15, 0.17, 0.19, 0.3, 0.5, 0.7, 0.9, 1, 1.1, 1.3, 1.5, 1.7, 1.9, 2.1, 2.3, 2.5, 2.7, 2.9, 3, 3.1, 3.3, 3.5, 3.7, 3.9, 4.1, 4.3, 4.5, 4.7, 4.9, 5); or any combination thereof.

Or, in certain embodiments, even if these amino acids are present in the formulation, they are not present in an amount that would affect barrier integrity of the skin. By "negligible" it is meant that the specific amino acid present has no effect on barrier integrity of the skin. By "negligible" it is meant that the specific amino acid present has no effect on a disease or condition that is related to barrier integrity of the skin, e.g., wound healing, treating skin conditions (e.g., atopic dermatitis, psoriasis, or condition related to the aging of skin) in a subject in need thereof.

Amino acids, if present in a formulation described herein, may be present in, for example, at a concentration of 0.5 mM, about 1 mM, about 2 mM, about 3 mM, about 4 mM, about 5 mM, about 6 mM, about 7 mM, about 8 mM, about 9 mM or about 10 mM. For example, 4 mM of each amino acid comprises: 0.0356% alanine; 0.0584% glutamine; 0.03% glycine; and 0.042% serine. In some aspects, each of the amino acids (4% or 4 mM) in the formulations described here are about 100-fold greater than the concentrations that have been used in tissue culture (TC) experiments.

In one embodiment, the total osmolarity of the formulation is from about 10 mosm to about 280 mosm 50 mosm to about 280 mosm, 100 mosm to about 280 mosm, or about 150 to about 260 mosm.

In some embodiments, the formulation has a pH from, for example, about 2.5 to about 8.5. In some embodiments, the formulation has a pH from about 2.5 to about 6.5, about 2.5 to about 6.0, about 3.0 to about 6.0, about 3.5 to about 6.0, about 3.9 to about 6.0, about 4.2 to about 6.0, about 3.5 to about 5.5, about 3.9 to about 5.0, or about 4.2 to about 4.6. In some embodiments, the pH is about 4.0 to about 6.0 or about 4.5 to about 5.7.

In some embodiments, the formulation is administered systemically or locally. In some embodiments, the formulation is used for treating a disease or condition that is related to barrier integrity of the skin, e.g., xerotic skin, wound healing, treating skin conditions (e.g., is atopic dermatitis, dermatitis, psoriasis, aging of skin, a condition related to the aging of skin, pruritus, or eczema), and/or improving barrier integrity of the skin. The therapeutic formulation can be administered via an enteral route or parenterally or topically or by inhalation. In certain embodiments, the formulation is therapeutic, cosmetic, or nutritional.

In some embodiments, the formulation is a solution. The formulation can be administered with other therapeutic agents.

Formulations and Uses Thereof for Treating and/or Preventing Xerosis Cutis, Atopic Dermatitis, Dermatitis, Psoriasis, Pruritus, Eczema, a Wound, Burn, or a Condition Relating to Aging of Skin In certain embodiments, the present disclosure provides methods for treating and/or preventing Xerosis cutis, atopic dermatitis, dermatitis, psoriasis, pruritus, eczema, a wound, burn, or a condition relating to aging of the skin, the method comprising administering to the subject a formulation described herein.

In certain aspects, the formulation for use in treating and/or preventing Xerosis cutis, atopic dermatitis, dermatitis, psoriasis, pruritus, eczema, a wound, burn, or a condition relating to aging of the skin comprises: as free amino acids, a therapeutically effective amount of a combination of glutamine, glycine, alanine, and serine; and optionally, a therapeutically effective amount of at least one additional free amino acid of valine, isoleucine, arginine, threonine, or tryptophan, or any combination thereof; wherein the therapeutically effective amount of the combination of glutamine, glycine, alanine, and serine and the therapeutically effective amount of the at least one additional free amino acid improves barrier integrity of skin cells; and optionally, a dermatologically acceptable carrier; wherein the formulation improves barrier integrity of the skin. In a particular embodiment, the free amino acids comprise, consist essentially of, or consist of glutamine, glycine, alanine, serine, and valine; and at least one additional amino acid of isoleucine, arginine, threonine, or tryptophan, or any combination thereof. In a more particular embodiment, the free amino acids comprise, consist essentially of, or consist of glutamine, glycine, alanine, serine, valine, and isoleucine; and at least one additional amino acid of arginine, or threonine, or any combination thereof. In more particular embodiments, the free amino acids comprise, consist essentially of, or consist of glutamine, glycine, alanine, serine, and valine; the free amino acids comprise, consist essentially of, or consist of glutamine, glycine, alanine, serine, valine, and isoleucine; the free amino acids comprise, consist essentially of, or consist of glutamine, glycine, alanine, serine, valine, isoleucine, and arginine; the free amino acids comprise, consist essentially of, or consist of glutamine, glycine, alanine, serine, valine, isoleucine, and threonine; the free amino acids comprise, consist essentially of, or consist of glutamine, glycine, alanine, and serine; and at least one additional amino acid of isoleucine, arginine, threonine, or tryptophan, or any combination thereof; the free amino acids comprise, consist essentially of, or consist of glutamine, glycine, alanine, serine, and isoleucine; the free amino acids comprise, consist essentially of, or consist of glutamine, glycine, alanine, serine, and arginine; the free amino acids comprise, consist essentially of, or consist of glutamine, glycine, alanine, serine, and threonine; the free amino acids comprise, consist essentially of, or consist of glutamine, glycine, alanine, serine, and tryptophan; the free amino acids comprise, consist essentially of, or consist of glutamine, glycine, alanine, serine, and isoleucine; and at least one additional amino acid of arginine, or threonine, or tryptophan, or any combination thereof; the free amino acids comprise, consist essentially of, or consist of glutamine, glycine, alanine, serine, isoleucine, and arginine; the free amino acids comprise, consist essentially of, or consist of glutamine, glycine, alanine, serine, isoleucine, and threonine; the free amino acids comprise, consist essentially of, or consist of glutamine, glycine, alanine, serine, isoleucine, and tryptophan; the free amino acids comprise, consist essentially of, or consist of glutamine, glycine, alanine, serine, isoleucine, arginine, and threonine; the free amino acids comprise, consist essentially of, or consist of glutamine, glycine, alanine, serine, isoleucine, arginine, and tryptophan; the free amino acids comprise, consist essentially of, or consist of glutamine, glycine, alanine, serine, isoleucine, threonine, and tryptophan; the free amino acids comprise, consist essentially of, or consist of glutamine, glycine, alanine, serine, isoleucine, arginine, threonine, and tryptophan; the free amino acids comprise, consist essentially of, or consist of glutamine, glycine, alanine, serine, and arginine; and at least one additional amino acid of isoleucine, threonine, or tryptophan, or any combination thereof; the free amino acids comprise, consist essentially of, or consist of glutamine, glycine, alanine, serine, and threonine; and at least one additional amino acid of isoleucine, arginine, or tryptophan, or any combination thereof; or the free amino acids comprise, consist essentially of, or consist of glutamine, glycine, alanine, serine, and tryptophan; and at least one additional amino acid of isoleucine, arginine, or threonine, or any combination thereof.

In one embodiment, the formulation optionally comprises, for example, pharmaceutically acceptable carriers, adjuvants, other active agents, and additives (e.g., sugars, electrolytes, vitamins, minerals, etc.). Formulation may further comprise, for example, a prebiotic or probiotic substance.

In some embodiments of formulations described herein, wherein, if present, free amino acids of cysteine are present at a concentration of equal to or less than 1 mM; if present, free amino acids of histidine are present at a concentration of equal to or less than 0.5 mM; if present, free amino acids of tyrosine are present at a concentration of equal to or less than 1 mM; if present, free amino acids of leucine are present at a concentration of equal to or less than 4 mM; or if present, free amino acids of aspartic acid are present at a concentration of equal to or less than 2 mM; or any combination thereof. In some embodiments of the formulation, the formulation does not comprise free amino acids of cysteine, histidine, tyrosine, leucine, aspartic acid, taurate, taurine, or glutamate, or any combination thereof.

Or, in certain embodiments, even if these amino acids are present in the formulation, they are not present in an amount that would affect barrier integrity of the skin. By "negligible" it is meant that the specific amino acid present has no effect on barrier integrity of the skin. By "negligible" it is meant that the specific amino acid present has no effect on a disease or condition that is related to barrier integrity of the skin, e.g., wound healing, treating skin conditions (e.g., atopic dermatitis, psoriasis, or condition related to the aging of skin) in a subject in need thereof.

Amino acids, if present in a formulation described herein, may be present in, for example, at a concentration of about 0.5 mM, about 1 mM, about 2 mM, about 3 mM, about 4 mM, about 5 mM, about 6 mM, about 7 mM, about 8 mM, about 9 mM or about 10 mM.

In one embodiment, the total osmolarity of the formulation is from about 10 mosm to about 280 mosm 50 mosm to about 280 mosm, 100 mosm to about 280 mosm, or about 150 to about 260 mosm.

In some embodiments, the formulation has a pH from, for example, about 2.5 to about 8.5. In some embodiments, the formulation has a pH from about 2.5 to about 6.5, about 2.5 to about 6.0, about 3.0 to about 6.0, about 3.5 to about 6.0, about 3.9 to about 6.0, about 4.2 to about 6.0, about 3.5 to about 5.5, about 3.9 to about 5.0, or about 4.2 to about 4.6. In some embodiments, the pH is about 4.0 to about 6.0 or about 4.5 to about 5.7.

In some embodiments, the formulation is administered systemically or locally. In some embodiments, the formulation is used for treating a disease or condition that is related to barrier integrity of the skin, e.g., xerotic skin, wound healing, treating skin conditions (e.g., is atopic dermatitis, dermatitis, psoriasis, aging of skin, a condition related to the aging of skin, pruritus, or eczema), and/or improving barrier integrity of the skin. The therapeutic formulation can be administered via an enteral route or parenterally or topically or by inhalation, or any combination thereof. In certain embodiments, the formulation is therapeutic, cosmetic, or nutritional.

In some embodiments, the formulation is a solution. The formulation can be administered with other therapeutic agents.

In some embodiments, the formulation is administered systemically or locally. The therapeutic formulation can be administered via an enteral route or parenterally or topically or by inhalation. In certain embodiments, the formulation is therapeutic, cosmetic, or nutritional.

In certain embodiments, the formulations may comprise natural amino acids or derivatives thereof that retain substantially the same, or better, activity in terms of improving barrier integrity of skin. In certain embodiments, the formulations may comprise natural amino acids or derivatives thereof that retain substantially the same, or better, activity in terms of treating xerosis cutis, wound healing, and/or treating skin conditions (e.g., atopic dermatitis, psoriasis, or condition related to the aging of skin) in a subject in need thereof. The derivatives may be, for example, enantiomers, and include both the D- and L-forms of the amino acids. The derivatives may be, for example, iodotyrosine, or norvaline. Other amino acid derivatives include, for example, norleucine, ornithine, penicillamine, pyroglutamine derivatives, or other derivatives of alanine, asparagine, aspartic acid, cysteine, glutamic acid, glycine, isoleucine, leucine, lysine, methionine, proline, phenylalanine, serine, threonine, tryptophan, or valine. In certain embodiments, the amino acid derivatives are derivatives of at least one of glutamine, glycine, alanine, serine, valine, isoleucine, arginine, threonine, or tryptophan, or any combination thereof. Other amino acid derivatives include, but are not limited to, those that are synthesized by, for example, acylation, methylation, and/or halogenation of the amino acid. These include, for example, β-methyl amino acids, C-methyl amino acids, and N-methyl amino acids.

In certain embodiments, the formulation also comprises additives (e.g., nutrients, electrolytes, vitamins, minerals, etc.). In certain embodiments, the formulation comprises iron or zinc. In certain embodiments, the therapeutic formulation comprises one or more electrolytes selected from, for example, $Na^+$; $K^+$; $HCO_{3-}$; $CO_3^{2-}$; $Ca^{2+}$; $Mg^{2+}$; $Fe_2$; $Cl^-$; phosphate ions, such as $H_2PO_4^-$, $HPO_4^{2-}$, and $PO_4^{3-}$; zinc; iodine; copper; iron; selenium; chromium; and molybdenum. In an alternative embodiment, the formulation does not contain $HCO_3^-$ or $CO_3^{2-}$. In another alternative embodiment, the formulation comprises $HCO_3^-$ and $CO_3^{2-}$ at a total concentration of less than 5 mg/l, or concentrations lower than 5 mg/l. In certain embodiments, the formulation does not contain electrolytes. For example, in certain embodiments, the formulation does not include one or more, or any, of $Na^+$; $K^+$; $HCO_3^-$; $CO_3^{2-}$; $Ca^{2+}$; $Mg^{2+}$; $Fe_2$; $Cl^-$; phosphate ions, such as $H_2PO_4^-$, $HPO_4^{2-}$, and $PO_4^{3-}$; zinc; iodine; copper; iron; selenium; chromium; and molybdenum.

In one embodiment, phosphate ions, such as $H_2PO_4^-$, $HPO_4^{2-}$, and $PO_4^{3-}$, are used to buffer the formulation described herein. In one embodiment, the therapeutic formulation uses $HCO_3^-$ or $CO_3^{2-}$ as a buffer. In another embodiment, the therapeutic formulation does not use $HCO_3^-$ or $CO_3^{2-}$ as buffer.

In some embodiments, the formulation and methods described herein are useful for cosmetic applications where, for example, rejuvenation of the various layers of the skin and/or the underlying tissues is desired. This rejuvenation can be aided by, for example, the improving barrier integrity of the skin.

In this embodiment, the methods of the present disclosure generally include the step of topically applying the formulations to the skin (e.g., epidermis) of the patient needing such treatment, wherein a therapeutically effective amount of such formulation is applied. In one embodiment, the formulation is applied to the face.

Advantageously, the present invention provides formulations and methods that combat the aging of skin, wherein combating the aging of skin can include, for example, treating the appearance of wrinkles, fine lines, and other forms of undesirable skin texture. By presenting the formulation to the dermal and/or epidermal layer(s) of the skin, the form, strength, as well as function of the skin is enhanced. In certain embodiments, the formulation and methods described herein are useful for beauty applications where, for example, rejuvenation of the various layers of the skin and/or the underlying tissues is desired.

In some embodiments, the formulations of the present disclosure comprise agents, in addition to the amino acids, that are useful in delaying, minimizing, or eliminating skin aging, wrinkling, and/or other histological changes typically associated with the intrinsic conditions (such as aging, menopause, etc.) and extrinsic conditions (such as environmental pollution (e.g., cigarette smoke), wind, heat, sunlight, radiation, low humidity, harsh surfactants, etc.).

The present invention is useful for therapeutically and/or prophylactically improving visible and/or tactile characteristics in skin. For example, in one embodiment, the length, depth, and/or other dimension of lines and/or wrinkles are decreased.

In one embodiment, the formulation applied to the skin or other tissue can further comprise collagen, hyaluronic acid (HA), and/or ceramides. In one embodiment, the HA is cross-linked HA. The formulation can further comprise components and/or additives such as, but not limited to, dermatologically acceptable carriers, desquamation agents, anti-acne agents, anti-wrinkle agents/anti-atrophy agents, vitamin B3 compounds, retinoids, hydroxyl acids, antioxidants/radical scavengers, chelators, flavonoids, anti-inflammatory agents, anti-cellulite agents, topical anesthetics, tanning agents, skin lightening agents, skin soothing and skin healing agents, antimicrobial and antifungal agents, sunscreen agents, conditioning agents, structuring agents, thickening agent (including thickeners and gelling agents), formulation preparation and preservatives. In this regard, international PCT application publication, WO 2008/089408 is incorporated herein, by reference, in its entirety.

In another aspect, the present disclosure provides methods of treating and/or preventing a skin condition (e.g., atopic dermatitis, psoriasis, or condition related to the aging of skin) in a subject in need thereof, the method comprising administering to the subject a formulation described herein. In certain embodiments, the skin condition is atopic dermatitis, psoriasis, the aging of skin, or a condition related to the aging of skin. In some embodiments, the skin condition is pruritus (itch), psoriasis, eczema, burns, or dermatitis. In certain embodiments, the skin condition is psoriasis. In certain embodiments, the skin condition is pruritis.

The formulation of the present disclosure can also be administered at a surgical site, including at a site of minimally invasive surgery, to improve healing and the surgical outcome.

Formulations and Uses Thereof for Skin Barrier Repair and Strengthening

In some embodiments, a formulation or a topical formulation of the disclosure comprises (or consists essentially of or consists of): as free amino acids, a therapeutically effective amount of a combination comprising (or consisting essentially of or consisting of): at least one of: alanine, glutamine, glycine, and serine, or salts thereof; a therapeutically effective amount of a plant extract, wherein the plant extract comprises (or consists essentially of or consists of): a *Boswellia* extract (e.g., *Boswellia serrata*; Burseraceae family; olibanum; frankincense); and optionally, a dermatologically acceptable carrier and/or additive. Additional aspects of the formulation or the topical formulation comprising, consisting essentially of, or consisting of, a therapeutically effective amount of an amino acid combination comprising, consisting essentially of, or consisting of alanine; glutamine; glycine; serine; alanine and glutamine; glycine and serine; alanine and glutamine; alanine and glycine; alanine and serine; glutamine and glycine; glutamine and serine; glycine and serine; alanine, glutamine, and glycine; glutamine, glycine, and serine; alanine, glutamine, and serine; or alanine, glutamine, glycine, and serine, or salts thereof. Further aspects of the formulation described here provide a therapeutically effective amount of the amino acid combination and/or a therapeutically effective amount of the plant extract (e.g., *Boswellia* extract) sufficient to improve skin barrier repair (e.g., skin barrier correction, skin barrier strengthening, skin barrier preservation, wound healing; growth, stimulation, proliferation, differentiation, and migration of epidermal cells, keratinocyte, endothelial cells, and fibroblasts; facilitates dermal regeneration) as indicated by an average fold increase of a barrier marker gene, EGR, expression of: 1.5 or greater (e.g., 1.7; 1.9; 2.1; 2.3; 2.5; 2.7; 2.9; 3.1; 3.3; 3.5; 3.7; 3.9; 4.1; 4.3; 4.5; 4.7; 4.9; 5.1; 5.3; 5.5; 5.7; 5.9; 6.1; 6.3; 6.5; 6.7; 6.9; 7.1; 7.3; 7.5; 7.7; 7.9; 8.1; 8.3; 8.5; 8.7; 8.9; 9.1; 9.3; 9.5; 9.7; 9.9; 10.1; 10.3; 10.5; 10.7; 10.9; 11.1; 11.3; 11.5; 11.7; 11.9; 12.1; 12.3; 12.5; 12.7; 12.9; 13.1; 13.3; 13.5; 13.7; 13.9; 14.1; 14.3; 14.5; 14.7; 14.9; 15.1; 15.3; 15.5; 15.7; 15.9; 16.1; 16.3; 16.5; 16.7; 16.9; 17.1; 17.3; 17.5; 17.7; 17.9; 18.1; 18.3; 18.5; 18.7; 18.9; 19.1; 19.3; 19.5; 19.7; 19.9; 20.1; 20.3; 20.5; 20.7; 20.9; 21.1; 21.3; 21.5; 21.7; 21.9; 22.1; 22.3; 22.5; 22.7; 22.9; 23.1; 23.3; 23.5; 23.7; 23.9; 23.1; 23.3; 23.5; 23.7; 23.9; 24.1; 24.3; 24.5; 24.7; 24.9; 25.1; 25.3; 25.5; 25.7; 25.9; 26.1; 26.3; 26.5; 26.7; 26.9; 27.1; 27.3; 27.5; 27.7; 27.9; 28.1; 28.3; 28.5; 28.7; 28.9; 29.1; 29.3; 29.5; 29.7; 29.9; 30.1; 30.3; 30.5; 30.7; 30.9; 31.1; 31.3; 31.5; 31.7; 31.9; 32.1; 32.3; 32.5; 32.7; 32.9; 33.1; 33.3; 33.5; 33.7; 33.9; 34.1; 34.3; 34.5; 34.7; 34.9; 35.1; 35.3; 35.5; 35.7; 35.9; 36.1; 36.3; 36.5; 36.7; 36.9; 37.1; 37.3; 37.5; 37.7; 37.9; 38.1; 38.3; 38.5; 38.7; 38.9; 39.1; 39.3; 39.5; 39.7; 39.9; 40.1; 40.3; 40.5; 40.7; 40.9; 41.1; 41.3; 41.5); 40 or less (e.g., 39.8; 39.6; 39.4; 39.2; 39; 38.8; 38.6; 38.4; 38.2; 38; 37.8; 37.6; 37.4; 37.2; 37; 36.8; 36.6; 36.4; 36.2; 36; 35.8; 35.6; 35.4; 35.2; 35; 34.8; 34.6; 34.4; 34.2; 34; 33.8; 33.6; 33.4; 33.2; 33; 32.8; 32.6; 32.4; 32.2; 32; 31.8; 31.6; 31.4; 31.2; 31; 30.8; 30.6; 30.4; 30.2; 30; 29.8; 29.6; 29.4; 29.2; 29; 28.8; 28.6; 28.4; 28.2; 28; 27.8; 27.6; 27.4; 27.2; 27; 26.8; 26.6; 26.4; 26.2; 26; 25.8; 25.6; 25.4; 25.2; 25; 24.8; 24.6; 24.4; 24.2; 24; 23.8; 23.6; 23.4; 23.2; 23; 22.8; 22.6; 22.4; 22.2; 22; 21.8; 21.6; 21.4; 21.2; 21; 20.8; 20.6; 20.4; 20.2; 20; 19.8; 19.6; 19.4; 19.2; 19; 18.8; 18.6; 18.4; 18.2; 18; 17.8; 17.6; 17.4; 17.2; 17.2; 17; 16.8; 16.6; 16.4; 16.2; 16; 15.8; 15.6; 15.4; 15.2; 15; 14.8; 14.6; 14.4; 14.2; 14; 13.8; 13.6; 13.4; 13.2; 13; 12.8; 12.6; 12.4; 12.2; 12; 11.8; 11.6; 11.4; 11.2; 11; 10.8; 10.6; 10.4; 10.2; 10; 9.8; 9.6; 9.4; 9.2; 9; 8.8; 8.6; 8.4; 8.2; 8; 7.8; 7.6; 7.4; 7.2; 7; 6.8; 6.6; 6.4; 6.2; 6; 5.8; 5.6; 5.4; 5.2; 5; 4.8; 4.6; 4.4; 4.2; 4; 3.8; 3.6; 3.4; 3.2; 3; 2.8; 2.6; 2.4; 2.2; 2; 1.8; 1.6; 1.4; 1.2; 1; 0.8; 0.6); or 1.5-40 (e.g., 1.6-39.9; 1.7-39.8; 1.8-39.7; 1.9-39.6; 2-39.5; 2.1-39.4; 2.2-39.3; 2.3-39.2; 2.4-39.1; 2.5-39; 2.6-38.9; 2.7-38.8; 2.8-38.7; 2.9-38.6; 3-38.5; 3.1-38.4; 3.2-38.3; 3.3-38.2; 3.4-38.1; 3.5-38; 3.6-37.9; 3.7-37.8; 3.8-37.7; 3.9-37.6; 4-37.5; 4.1-37.4; 4.2-37.3; 4.3-37.2; 4.4-37.1; 4.5-37; 4.6-36.9; 4.7-36.8; 4.8-36.7; 4.9-36.6; 5-36.5; 5.1-36.4; 5.2-36.3; 5.3-36.2; 5.4-36.1; 5.5-36; 5.6-35.9; 5.7-35.8; 5.8-35.7; 5.9-35.6; 6-35.5; 6.1-35.4; 6.2-35.3; 6.3-35.2; 6.4-35.1; 6.5-35; 6.6-34.9; 6.7-34.8; 6.8-34.7; 6.9-34.6; 7-34.5; 7.1-34.4; 7.2-34.3; 7.3-34.2; 7.4-34.1; 7.5-34; 7.6-33.9; 7.7-33.8; 7.8-33.7; 7.9-33.6; 8-33.5; 8.1-33.4; 8.2-33.3; 8.3-33.2; 8.4-33.1; 8.5-33; 8.6-32.9; 8.7-32.8; 8.8-32.7; 8.9-32.6; 9-32.5; 9.1-32.4; 9.2-32.3; 9.3-32.2; 9.4-32.1; 9.5-32; 9.6-31.9; 9.7-31.8; 9.8-31.7; 9.9-31.6; 10-31.5; 10.1-31.4; 10.2-31.3; 10.3-31.2; 10.4-31.1; 10.5-31; 10.6-30.9; 10.7-30.8; 10.8-30.7; 10.9-30.6; 11-30.5; 11.1-30.4; 11.2-30.3; 11.3-30.2; 11.4-30.1; 11.5-30; 11.6-29.9; 11.7-29.8; 11.8-29.7; 11.9-29.6; 12-29.5; 12.1-29.4; 12.2-29.3; 12.3-29.2; 12.4-29.1; 12.5-29; 12.6-28.9; 12.7-28.8; 12.8-28.7; 12.9-28.6; 13-28.5; 13.1-28.4; 13.2-28.3; 13.3-28.2; 13.4-28.1; 13.5-28; 13.6-27.9; 13.7-27.8; 13.8-27.7; 13.9-27.6; 14-27.5; 14.1-27.4; 14.2-27.3; 14.3-27.2; 14.4-27.1; 14.5-27; 14.6-26.9; 14.7-26.8; 14.8-26.7; 14.9-26.6; 15-26.5; 15.1-26.4; 15.2-26.3; 15.3-26.2; 15.4-26.1; 15.5-26; 15.6-25.9; 15.7-25.8; 15.8-25.7; 15.9-25.6; 16-25.5; 16.1-25.4; 16.2-25.3; 16.3-25.2; 16.4-25.1; 16.5-25; 16.6-24.9; 16.7-24.8; 16.8-24.7; 16.9-24.6; 17-24.5; 17.1-24.4; 17.2-24.3; 17.3-24.2; 17.4-24.1; 17.5-24; 17.6-23.9; 17.7-23.8; 17.8-23.7; 17.9-23.6; 18-23.5; 18.1-23.4; 18.2-23.3; 18.3-23.2; 18.4-23.1; 18.5-23; 18.6-22.9; 18.7-22.8; 18.8-22.7; 18.9-22.6; 19-22.5; 19.1-22.4; 19.2-22.3; 19.3-22.2; 19.4-22.1; 19.5-22; 19.6-21.9; 19.7-21.8; 19.8-21.7; 19.9-21.6; 20-21.5; 20.1-21.4; 20.2-21.3; 20.3-21.2; 20.4-21.1; 20.5-21; 20.6-20.9; 20.7-20.8). See, e.g., FIGS. 8-14.

Other embodiments provide a formulation or a topical formulation, comprising (or consisting essentially of or consisting of): as free amino acids, a therapeutically effective amount of a combination comprising (or consisting essentially of or consisting of): alanine, glutamine, glycine, and serine, or salts thereof; a therapeutically effective amount of a plant extract (e.g., *Boswellia* extract (e.g., *Boswellia serrata*; Burseraceae family; olibanum; frankincense) or a plant extract combination (e.g., BOSEXIL® (INDENA SpA) or *Boswellia serrata* resin extract, cellulose (microcrystalline), lecithin, silica), comprising (or consisting essentially of, or consisting of): *Boswellia* extract (e.g., *Boswellia serrata*; Burseraceae family; olibanum; frankincense); a texturing and/or a bulking agent (e.g., cellulose (microcrystalline)); an emulsifier or a phospholipid, where in some embodiments, phospholipids are used as an emulsifier (e.g., lecithin or phosphatidylcholine); and an anti-caking agent (e.g., silica, adsorbs water in hygroscopic applications); and optionally, a dermatologically acceptable carrier and/or additive.

In additional embodiments, a formulation or a topical formulation for administration to skin of a subject, comprises (or consists essentially of or consists of): a therapeutically effective amount of a combination of free amino acids comprising (or consisting essentially of or consisting of): alanine, glutamine, glycine, and serine, or salts thereof; a therapeutically effective amount of a plant extract (e.g., *Boswellia* extract (e.g., *Boswellia serrata*; Burseraceae family; olibanum; frankincense) or a plant extract combination comprising (consisting essentially of or consisting of) (e.g., BOSEXIL™ or *Boswellia serrata* resin extract, cellulose (microcrystalline), lecithin, silica): *Boswellia* extract (e.g., *Boswellia serrata*; Burseraceae family; olibanum; frankincense); a texturing and/or a bulking agent (e.g., cellulose (microcrystalline); an emulsifier or a phospholipid, where in some embodiments, phospholipids are used as an emulsifier (e.g., lecithin or phosphatidylcholine, soy lecithin); and an anti-caking agent (e.g., silica, adsorbs water in hygroscopic applications); and optionally, a dermatologically acceptable carrier and/or additive, wherein the therapeutically effective amount of the combination of free amino acids and the therapeutically effective amount of the plant extract or plant extract combination improves skin barrier repair (e.g., skin barrier correction, skin barrier strengthening, skin barrier preservation, wound healing; growth, stimulation, proliferation, differentiation, and migration of epidermal cells, keratinocyte, endothelial cells, and fibroblasts; facilitates dermal regeneration), wherein the formulation or the topical formulation improves skin barrier repair (e.g., skin barrier correction, skin barrier strengthening, skin barrier preservation, wound healing; growth, stimulation, proliferation, differentiation, and migration of epidermal cells, keratinocyte, endothelial cells, and fibroblasts; facilitates dermal regeneration) when tested by a method detecting expression of a barrier marker gene, EGF, and determining that the barrier marker gene is increased by a 1.5-40 average fold increase of amino acid treated as compared to amino acid untreated skin (see, e.g., FIGS. 8-14).

Further embodiments described here provide the formulation or the topical formulation of the disclosure, wherein each of the free amino acids (at least one of: alanine, glutamine, glycine, and serine, or salts thereof) is present at a concentration: of 0.1 mM or greater (e.g., 0.3, 0.5, 0.7; 0.9; 1.1; 1.3; 1.5; 1.7; 1.9; 2.1; 2.3; 2.5; 2.7; 2.9; 3.1; 3.3; 3.5; 3.7; 3.9; 4.1; 4.3; 4.5; 4.7; 4.9; 5.1; 5.3; 5.5; 5.7; 5.9; 6.1; 6.3; 6.5; 6.7; 6.9; 7.1; 7.3; 7.5; 7.7; 7.9; 8.1; 8.3; 8.5; 8.7; 8.9; 9.1; 9.3; 9.5; 9.7; 9.9; 10.1; 10.3; 10.5); of 10 mM or less (e.g., 9.8; 9.6; 9.4; 9.2; 9; 8.8; 8.6; 8.4; 8.2; 8; 7.8; 7.6; 7.4; 7.2; 7; 6.8; 6.6; 6.4; 6.2; 6; 5.8; 5.6; 5.4; 5.2; 5; 4.8; 4.6; 4.4; 4.2; 4; 3.8; 3.6; 3.4; 3.2; 3; 2.8; 2.6; 2.4; 2.2; 2; 1.8; 1.6; 1.4; 1.2; 1; 0.8; 0.6; 0.4; 0.2; 0.08; 0.06; 0.04; 0.02); or ranging from 0.1 mM to 10 mM (e.g., 0.2 mM to 9.9 mM; 0.3 mM to 9.8 mM; 0.4 mM to 9.7 mM; 0.5 mM to 9.6 mM; 0.6 mM to 9.5 mM; 0.7 mM to 9.4 mM; 0.8 mM to 9.3 mM; 0.9 mM to 9.2 mM; 1 mM to 9.1 mM; 1.1 mM to 9 mM; 1.2 mM to 8.9 mM; 1.3 mM to 8.8 mM; 1.4 mM to 8.7 mM; 1.5 mM to 8.6 mM; 1.6 mM to 8.5 mM; 1.7 mM to 8.4 mM; 1.8 mM to 8.3 mM; 1.9 mM to 8.2 mM; 2 mM to 8.1 mM; 2.1 mM to 8 mM; 2.2 mM to 7.9 mM; 2.3 mM to 7.8 mM; 2.4 mM to 7.7 mM; 2.5 mM to 7.6 mM; 2.6 mM to 7.5 mM; 2.7 mM to 7.4 mM; 2.8 mM to 7.3 mM; 2.9 mM to 7.2 mM; 3 mM to 7.1 mM; 3.1 mM to 7 mM; 3.2 mM to 6.9 mM; 3.3 mM to 6.8 mM; 3.4 mM to 6.7 mM; 3.5 mM to 6.6 mM; 3.6 mM to 6.5 mM; 3.7 mM to 6.4 mM; 3.8 mM to 6.3 mM; 3.9 mM to 6.2 mM; 4 mM to 6.1 mM; 4.1 mM to 6 mM; 4.2 mM to 5.9 mM; 4.3 mM to 5.8 mM; 4.4 mM to 5.7 mM; 4.5 mM to 5.6 mM; 4.6 mM to 5.5 mM; 4.7 mM to 5.4 mM; 4.8 mM to 5.3 mM; 4.9 mM to 5.2 mM; 5 mM to 5.1 mM).

In some embodiments described here, the disclosed formulation or the topical formulation are provided, wherein each of the free amino acids (at least one of: alanine, glutamine, glycine, and serine, or salts thereof) is present at a weight percent to the formulation (wt/wt %) of: 0.001 wt % or greater (e.g., 0.002; 0.003; 0.004; 0.005; 0.006; 0.007; 0.008; 0.009; 0.01; 0.02; 0.03; 0.04; 0.05; 0.06; 0.07; 0.08; 0.09; 0.1; 0.2; 0.3; 0.4; 0.5; 0.6; 0.7; 0.8; 0.9; 1); 1 wt % or less (e.g., 0.95; 0.85; 0.75; 0.65; 0.55; 0.45; 0.35; 0.25; 0.15; 0.095; 0.085; 0.075; 0.065; 0.055; 0.045; 0.035; 0.025; 0.015; 0.0095; 0.0085; 0.0075; 0.0065; 0.0055; 0.0045; 0.0035; 0.0025; 0.0015); or 0.001 wt % to 1 wt % (e.g., 0.0012 wt % to 0.99 wt %; 0.0014 wt % to 0.97 wt %; 0.0016 wt % to 0.95 wt %; 0.0018 wt % to 0.93 wt %; 0.002 wt % to 0.91 wt %; 0.0022 wt % to 0.89 wt %; 0.0024 wt % to 0.87 wt %; 0.0026 wt % to 0.85 wt %; 0.0028 wt % to 0.83 wt %; 0.003 wt % to 0.81 wt %; 0.0032 wt % to 0.79 wt %; 0.0034 wt % to 0.77 wt %; 0.0036 wt % to 0.75 wt %; 0.0038 wt % to 0.73 wt %; 0.004 wt % to 0.71 wt %; 0.0042 wt % to 0.69 wt %; 0.0044 wt % to 0.67 wt %; 0.0046 wt % to 0.65 wt %; 0.0048 wt % to 0.63 wt %; 0.005 wt % to 0.61 wt %; 0.0052 wt % to 0.59 wt %; 0.0054 wt % to 0.57 wt %; 0.0056 wt % to 0.55 wt %; 0.0058 wt % to 0.53 wt %; 0.006 wt % to 0.51 wt %; 0.0062 wt % to 0.49 wt %; 0.0064 wt % to 0.47 wt %; 0.0066 wt % to 0.45 wt %; 0.0068 wt % to 0.43 wt %; 0.007 wt % to 0.41 wt %; 0.0072 wt % to 0.39 wt %; 0.0074 wt % to 0.37 wt %; 0.0076 wt % to 0.35 wt %; 0.0078 wt % to 0.33 wt %; 0.008 wt % to 0.31 wt %; 0.0082 wt % to 0.29 wt %; 0.0084 wt % to 0.27 wt %; 0.0086 wt % to 0.25 wt %; 0.0088 wt % to 0.23 wt %; 0.009 wt % to 0.21 wt %; 0.0092 wt % to 0.19 wt %; 0.0094 wt % to 0.17 wt %; 0.0096 wt % to 0.15 wt %; 0.0098 wt % to 0.13 wt %; 0.01 wt % to 0.11 wt %; 0.012 wt % to 0.099 wt %; 0.014 wt % to 0.097 wt %; 0.016 wt % to 0.095 wt %; 0.018 wt % to 0.093 wt %; 0.02 wt % to 0.091 wt %; 0.022 wt % to 0.089 wt %; 0.024 wt % to 0.087 wt %; 0.026 wt % to 0.085 wt %; 0.028 wt % to 0.083 wt %; 0.03 wt % to 0.081 wt %; 0.032 wt % to 0.079 wt %; 0.034 wt % to 0.077 wt %; 0.036 wt % to 0.075 wt %; 0.038 wt % to 0.073 wt %; 0.04 wt % to 0.071 wt %; 0.042 wt % to 0.069 wt %; 0.044 wt % to 0.067 wt %; 0.046 wt % to 0.065 wt %; 0.048 wt % to 0.063 wt %; 0.05 wt % to 0.061 wt %; 0.052 wt % to 0.059 wt %; 0.054 wt % to 0.057 wt %).

Other embodiments provide the formulation or the topical formulation described here, wherein alanine is present at a weight percent to the formulation (wt/wt %) of: 0.0035 wt % or greater (e.g., 0.00352; 0.00354; 0.00356; 0.00358; 0.0036; 0.00362; 0.00364; 0.00366; 0.00368; 0.0037; 0.00372; 0.00374; 0.00376; 0.00378; 0.0038; 0.00382; 0.00384; 0.00386; 0.00388; 0.004; 0.0042; 0.0044; 0.0046; 0.0048; 0.005; 0.0052; 0.0054; 0.0056; 0.0058; 0.006; 0.0062; 0.0064; 0.0066; 0.0068; 0.007; 0.0072; 0.0074; 0.0076; 0.0078; 0.008; 0.0082; 0.0084; 0.0086; 0.0088; 0.009; 0.0092; 0.0094; 0.0096; 0.0098; 0.01; 0.012; 0.014; 0.016; 0.018; 0.02; 0.022; 0.024; 0.026; 0.028; 0.03; 0.032; 0.034; 0.036; 0.038; 0.04; 0.042; 0.044; 0.046; 0.048; 0.05; 0.052; 0.054; 0.056; 0.058; 0.06; 0.062; 0.064; 0.066; 0.068; 0.07; 0.072; 0.074; 0.076; 0.078; 0.08; 0.082; 0.084; 0.086; 0.088; 0.09; 0.092; 0.094; 0.096; 0.098; 0.1; 0.102; 0.104; 0.106; 0.108; 0.11; 0.112; 0.114; 0.116; 0.118; 0.12; 0.122; 0.124; 0.126; 0.128; 0.13; 0.132; 0.134; 0.136; 0.138; 0.14; 0.142; 0.144; 0.146; 0.148; 0.15; 0.152; 0.154; 0.156; 0.158; 0.16; 0.162; 0.164; 0.166; 0.168; 0.17; 0.172; 0.174; 0.176; 0.178; 0.18; 0.182; 0.184; 0.186; 0.188; 0.19; 0.192; 0.194; 0.196; 0.198; 0.2; 0.202; 0.204; 0.206; 0.208; 0.21; 0.212; 0.214; 0.216; 0.218; 0.22; 0.222; 0.224; 0.226; 0.228; 0.23; 0.232; 0.234; 0.236; 0.238; 0.24; 0.242; 0.244; 0.246; 0.248; 0.25; 0.252; 0.254; 0.256; 0.258; 0.26; 0.262; 0.264; 0.266; 0.268; 0.27; 0.272; 0.274; 0.276; 0.278; 0.28; 0.282; 0.284; 0.286; 0.288; 0.19; 0.192; 0.194; 0.196; 0.198; 0.2; 0.202; 0.204; 0.206; 0.208; 0.21; 0.212; 0.214; 0.216; 0.218; 0.22; 0.222; 0.224; 0.226; 0.228; 0.23; 0.232; 0.234; 0.236; 0.238; 0.24; 0.242; 0.244; 0.246; 0.248; 0.25; 0.252; 0.254; 0.256; 0.258; 0.26; 0.262; 0.264; 0.266; 0.268; 0.27; 0.272; 0.274; 0.276; 0.278; 0.28; 0.282; 0.284; 0.286; 0.288; 0.3; 0.302; 0.304; 0.306; 0.308; 0.31; 0.312; 0.314; 0.316; 0.318; 0.32; 0.322; 0.324; 0.326; 0.328; 0.33; 0.332; 0.334; 0.336; 0.338; 0.34; 0.342; 0.344; 0.346; 0.348; 0.35; 0.352; 0.354; 0.356; 0.358; 0.36; 0.362; 0.364; 0.366; 0.368; 0.37; 0.372; 0.374; 0.376; 0.378; 0.38; 0.382; 0.384; 0.386; 0.388; 0.39; 0.392; 0.394; 0.396; 0.398; 0.4; 0.402; 0.404; 0.406; 0.408; 0.41;

0.412; 0.414; 0.416; 0.418; 0.42; 0.422; 0.424; 0.426; 0.428; 0.43; 0.432; 0.434; 0.436; 0.438; 0.44; 0.442; 0.444; 0.446; 0.448; 0.45; 0.452; 0.454; 0.456; 0.458; 0.46; 0.462; 0.464; 0.466; 0.468; 0.47; 0.472; 0.474; 0.476; 0.478; 0.48; 0.482; 0.484; 0.486; 0.488; 0.5); 0.4 wt % or less (e.g., 0.399; 0.397; 0.395; 0.393; 0.391; 0.389; 0.387; 0.385; 0.383; 0.381; 0.379; 0.377; 0.375; 0.373; 0.371; 0.369; 0.367; 0.365; 0.363; 0.361; 0.359; 0.357; 0.355; 0.353; 0.351; 0.349; 0.347; 0.345; 0.343; 0.341; 0.339; 0.337; 0.335; 0.333; 0.331; 0.329; 0.327; 0.325; 0.323; 0.321; 0.319; 0.317; 0.315; 0.313; 0.311; 0.309; 0.307; 0.305; 0.303; 0.301; 0.299; 0.297; 0.295; 0.293; 0.291; 0.289; 0.287; 0.285; 0.283; 0.281; 0.279; 0.277; 0.275; 0.273; 0.271; 0.269; 0.267; 0.265; 0.263; 0.261; 0.259; 0.257; 0.255; 0.253; 0.251; 0.249; 0.247; 0.245; 0.243; 0.241; 0.239; 0.237; 0.235; 0.233; 0.231; 0.229; 0.227; 0.225; 0.223; 0.221; 0.219; 0.217; 0.215; 0.213; 0.211; 0.209; 0.207; 0.205; 0.203; 0.201; 0.199; 0.197; 0.195; 0.193; 0.191; 0.189; 0.187; 0.185; 0.183; 0.181; 0.179; 0.177; 0.175; 0.173; 0.171; 0.169; 0.167; 0.165; 0.163; 0.161; 0.159; 0.157; 0.155; 0.153; 0.151; 0.149; 0.147; 0.145; 0.143; 0.141; 0.139; 0.137; 0.135; 0.133; 0.131; 0.129; 0.127; 0.125; 0.123; 0.121; 0.119; 0.117; 0.115; 0.113; 0.111; 0.109; 0.107; 0.105; 0.103; 0.101; 0.099; 0.097; 0.095; 0.093; 0.091; 0.089; 0.087; 0.085; 0.083; 0.081; 0.079; 0.077; 0.075; 0.073; 0.071; 0.069; 0.067; 0.065; 0.063; 0.061; 0.059; 0.057; 0.055; 0.053; 0.051; 0.049; 0.047; 0.045; 0.043; 0.041; 0.039; 0.037; 0.035; 0.033; 0.031; 0.029; 0.027; 0.025; 0.023; 0.021; 0.019; 0.017; 0.015; 0.013; 0.011; 0.009; 0.007; 0.005; 0.003; 0.002); or 0.0035 wt % to 0.36 wt % (e.g., 0.00351 wt % to 0.359 wt %; 0.00352 wt % to 0.358 wt %; 0.00353 wt % to 0.357 wt %; 0.00354 wt % to 0.356 wt %; 0.00355 wt % to 0.355 wt %; 0.00356 wt % to 0.354 wt %; 0.00357 wt % to 0.353 wt %; 0.00358 wt % to 0.352 wt %; 0.00359 wt % to 0.351 wt %; 0.0036 wt % to 0.35 wt %; 0.00361 wt % to 0.349 wt %; 0.00362 wt % to 0.348 wt %; 0.00363 wt % to 0.347 wt %; 0.00364 wt % to 0.346 wt %; 0.00365 wt % to 0.345 wt %; 0.00366 wt % to 0.344 wt %; 0.00367 wt % to 0.343 wt %; 0.00368 wt % to 0.342 wt %; 0.00369 wt % to 0.341 wt %; 0.0037 wt % to 0.34 wt %; 0.00371 wt % to 0.339 wt %; 0.00372 wt % to 0.338 wt %; 0.00373 wt % to 0.337 wt %; 0.00374 wt % to 0.336 wt %; 0.00375 wt % to 0.335 wt %; 0.00376 wt % to 0.334 wt %; 0.00377 wt % to 0.333 wt %; 0.00378 wt % to 0.332 wt %; 0.00379 wt % to 0.331 wt %; 0.0038 wt % to 0.33 wt %; 0.00381 wt % to 0.329 wt %; 0.00382 wt % to 0.328 wt %; 0.00383 wt % to 0.327 wt %; 0.00384 wt % to 0.326 wt %; 0.00385 wt % to 0.325 wt %; 0.00386 wt % to 0.324 wt %; 0.00387 wt % to 0.323 wt %; 0.00388 wt % to 0.322 wt %; 0.00389 wt % to 0.321 wt %; 0.0039 wt % to 0.32 wt %; 0.00391 wt % to 0.319 wt %; 0.00392 wt % to 0.318 wt %; 0.00393 wt % to 0.317 wt %; 0.00394 wt % to 0.316 wt %; 0.00395 wt % to 0.315 wt %; 0.00396 wt % to 0.314 wt %; 0.00397 wt % to 0.313 wt %; 0.00398 wt % to 0.312 wt %; 0.00399 wt % to 0.311 wt %; 0.004 wt % to 0.31 wt %; 0.00401 wt % to 0.309 wt %; 0.00402 wt % to 0.308 wt %; 0.00403 wt % to 0.307 wt %; 0.00404 wt % to 0.306 wt %; 0.00405 wt % to 0.305 wt %; 0.00406 wt % to 0.304 wt %; 0.00407 wt % to 0.303 wt %; 0.00408 wt % to 0.302 wt %; 0.00409 wt % to 0.301 wt %; 0.0041 wt % to 0.3 wt %; 0.00411 wt % to 0.299 wt %; 0.00412 wt % to 0.298 wt %; 0.00413 wt % to 0.297 wt %; 0.00414 wt % to 0.296 wt %; 0.00415 wt % to 0.295 wt %; 0.00416 wt % to 0.294 wt %; 0.00417 wt % to 0.293 wt %; 0.00418 wt % to 0.292 wt %; 0.00419 wt % to 0.291 wt %; 0.0042 wt % to 0.29 wt %; 0.00421 wt % to 0.289 wt %; 0.00422 wt % to 0.288 wt %; 0.00423 wt % to 0.287 wt %; 0.00424 wt % to 0.286 wt %; 0.00425 wt % to 0.285 wt %; 0.00426 wt % to 0.284 wt %; 0.00427 wt % to 0.283 wt %; 0.00428 wt % to 0.282 wt %; 0.00429 wt % to 0.281 wt %; 0.0043 wt % to 0.28 wt %; 0.00431 wt % to 0.279 wt %; 0.00432 wt % to 0.278 wt %; 0.00433 wt % to 0.277 wt %; 0.00434 wt % to 0.276 wt %; 0.00435 wt % to 0.275 wt %; 0.00436 wt % to 0.274 wt %; 0.00437 wt % to 0.273 wt %; 0.00438 wt % to 0.272 wt %; 0.00439 wt % to 0.271 wt %; 0.0044 wt % to 0.27 wt %; 0.00441 wt % to 0.269 wt %; 0.00442 wt % to 0.268 wt %; 0.00443 wt % to 0.267 wt %; 0.00444 wt % to 0.266 wt %; 0.00445 wt % to 0.265 wt %; 0.00446 wt % to 0.264 wt %; 0.00447 wt % to 0.263 wt %; 0.00448 wt % to 0.262 wt %; 0.00449 wt % to 0.261 wt %; 0.0045 wt % to 0.26 wt %; 0.00451 wt % to 0.259 wt %; 0.00452 wt % to 0.258 wt %; 0.00453 wt % to 0.257 wt %; 0.00454 wt % to 0.256 wt %; 0.00455 wt % to 0.255 wt %; 0.00456 wt % to 0.254 wt %; 0.00457 wt % to 0.253 wt %; 0.00458 wt % to 0.252 wt %; 0.00459 wt % to 0.251 wt %; 0.0046 wt % to 0.25 wt %; 0.00461 wt % to 0.249 wt %; 0.00462 wt % to 0.248 wt %; 0.00463 wt % to 0.247 wt %; 0.00464 wt % to 0.246 wt %; 0.00465 wt % to 0.245 wt %; 0.00466 wt % to 0.244 wt %; 0.00467 wt % to 0.243 wt %; 0.00468 wt % to 0.242 wt %; 0.00469 wt % to 0.241 wt %; 0.0047 wt % to 0.24 wt %; 0.00471 wt % to 0.239 wt %; 0.00472 wt % to 0.238 wt %; 0.00473 wt % to 0.237 wt %; 0.00474 wt % to 0.236 wt %; 0.00475 wt % to 0.235 wt %; 0.00476 wt % to 0.234 wt %; 0.00477 wt % to 0.233 wt %; 0.00478 wt % to 0.232 wt %; 0.00479 wt % to 0.231 wt %; 0.0048 wt % to 0.23 wt %; 0.00481 wt % to 0.229 wt %; 0.00482 wt % to 0.228 wt %; 0.00483 wt % to 0.227 wt %; 0.00484 wt % to 0.226 wt %; 0.00485 wt % to 0.225 wt %; 0.00486 wt % to 0.224 wt %; 0.00487 wt % to 0.223 wt %; 0.00488 wt % to 0.222 wt %; 0.00489 wt % to 0.221 wt %; 0.0049 wt % to 0.22 wt %; 0.00491 wt % to 0.219 wt %; 0.00492 wt % to 0.218 wt %; 0.00493 wt % to 0.217 wt %; 0.00494 wt % to 0.216 wt %; 0.00495 wt % to 0.215 wt %; 0.00496 wt % to 0.214 wt %; 0.00497 wt % to 0.213 wt %; 0.00498 wt % to 0.212 wt %; 0.00499 wt % to 0.211 wt %; 0.005 wt % to 0.21 wt %; 0.00501 wt % to 0.209 wt %; 0.00502 wt % to 0.208 wt %; 0.00503 wt % to 0.207 wt %; 0.00504 wt % to 0.206 wt %; 0.00505 wt % to 0.205 wt %; 0.00506 wt % to 0.204 wt %; 0.00507 wt % to 0.203 wt %; 0.00508 wt % to 0.202 wt %; 0.00509 wt % to 0.201 wt %; 0.0051 wt % to 0.2 wt %; 0.00511 wt % to 0.199 wt %; 0.00512 wt % to 0.198 wt %; 0.00513 wt % to 0.197 wt %; 0.00514 wt % to 0.196 wt %; 0.00515 wt % to 0.195 wt %; 0.00516 wt % to 0.194 wt %; 0.00517 wt % to 0.193 wt %; 0.00518 wt % to 0.192 wt %; 0.00519 wt % to 0.191 wt %; 0.0052 wt % to 0.19 wt %; 0.00521 wt % to 0.189 wt %; 0.00522 wt % to 0.188 wt %; 0.00523 wt % to 0.187 wt %; 0.00524 wt % to 0.186 wt %; 0.00525 wt % to 0.185 wt %; 0.00526 wt % to 0.184 wt %; 0.00527 wt % to 0.183 wt %; 0.00528 wt % to 0.182 wt %; 0.00529 wt % to 0.181 wt %; 0.0053 wt % to 0.18 wt %; 0.00531 wt % to 0.179 wt %; 0.00532 wt % to 0.178 wt %; 0.00533 wt % to 0.177 wt %; 0.00534 wt % to 0.176 wt %; 0.00535 wt % to 0.175 wt %; 0.00536 wt % to 0.174 wt %; 0.00537 wt % to 0.173 wt %; 0.00538 wt % to 0.172 wt %; 0.00539 wt % to 0.171 wt %; 0.0054 wt % to 0.17 wt %; 0.00541 wt % to 0.169 wt %; 0.00542 wt % to 0.168 wt %; 0.00543 wt % to 0.167 wt %; 0.00544 wt % to 0.166 wt %; 0.00545 wt % to 0.165 wt %; 0.00546 wt % to 0.164 wt %; 0.00547 wt % to 0.163 wt %; 0.00548 wt % to 0.162 wt %; 0.00549 wt % to 0.161 wt %; 0.0055 wt % to 0.16 wt %; 0.00551 wt % to 0.159 wt %; 0.00552 wt % to 0.158 wt %; 0.00553 wt % to 0.157 wt %; 0.00554 wt % to 0.156 wt %; 0.00555 wt % to 0.155 wt %; 0.00556 wt % to 0.154 wt %; 0.00557 wt % to 0.153 wt %;

0.00558 wt % to 0.152 wt %; 0.00559 wt % to 0.151 wt %; 0.0056 wt % to 0.15 wt %; 0.00561 wt % to 0.149 wt %; 0.00562 wt % to 0.148 wt %; 0.00563 wt % to 0.147 wt %; 0.00564 wt % to 0.146 wt %; 0.00565 wt % to 0.145 wt %; 0.00566 wt % to 0.144 wt %; 0.00567 wt % to 0.143 wt %; 0.00568 wt % to 0.142 wt %; 0.00569 wt % to 0.141 wt %; 0.0057 wt % to 0.14 wt %; 0.00571 wt % to 0.139 wt %; 0.00572 wt % to 0.138 wt %; 0.00573 wt % to 0.137 wt %; 0.00574 wt % to 0.136 wt %; 0.00575 wt % to 0.135 wt %; 0.00576 wt % to 0.134 wt %; 0.00577 wt % to 0.133 wt %; 0.00578 wt % to 0.132 wt %; 0.00579 wt % to 0.131 wt %; 0.0058 wt % to 0.13 wt %; 0.00581 wt % to 0.129 wt %; 0.00582 wt % to 0.128 wt %; 0.00583 wt % to 0.127 wt %; 0.00584 wt % to 0.126 wt %; 0.00585 wt % to 0.125 wt %; 0.00586 wt % to 0.124 wt %; 0.00587 wt % to 0.123 wt %; 0.00588 wt % to 0.122 wt %; 0.00589 wt % to 0.121 wt %; 0.0059 wt % to 0.12 wt %; 0.00591 wt % to 0.119 wt %; 0.00592 wt % to 0.118 wt %; 0.00593 wt % to 0.117 wt %; 0.00594 wt % to 0.116 wt %; 0.00595 wt % to 0.115 wt %; 0.00596 wt % to 0.114 wt %; 0.00597 wt % to 0.113 wt %; 0.00598 wt % to 0.112 wt %; 0.00599 wt % to 0.111 wt %; 0.0056 wt % to 0.11 wt %; 0.00561 wt % to 0.109 wt %; 0.00562 wt % to 0.108 wt %; 0.00563 wt % to 0.107 wt %; 0.00564 wt % to 0.106 wt %; 0.00565 wt % to 0.105 wt %; 0.00566 wt % to 0.104 wt %; 0.00567 wt % to 0.103 wt %; 0.00568 wt % to 0.102 wt %; 0.00569 wt % to 0.101 wt %; 0.0057 wt % to 0.1 wt %; 0.00571 wt % to 0.099 wt %; 0.00572 wt % to 0.098 wt %; 0.00573 wt % to 0.097 wt %; 0.00574 wt % to 0.096 wt %; 0.00575 wt % to 0.095 wt %; 0.00576 wt % to 0.094 wt %; 0.00577 wt % to 0.093 wt %; 0.00578 wt % to 0.092 wt %; 0.00579 wt % to 0.091 wt %; 0.0058 wt % to 0.09 wt %; 0.00581 wt % to 0.089 wt %; 0.00582 wt % to 0.088 wt %; 0.00583 wt % to 0.087 wt %; 0.00584 wt % to 0.086 wt %; 0.00585 wt % to 0.085 wt %; 0.00586 wt % to 0.084 wt %; 0.00587 wt % to 0.083 wt %; 0.00588 wt % to 0.082 wt %; 0.00589 wt % to 0.081 wt %; 0.0059 wt % to 0.08 wt %; 0.00591 wt % to 0.079 wt %; 0.00592 wt % to 0.078 wt %; 0.00593 wt % to 0.077 wt %; 0.00594 wt % to 0.076 wt %; 0.00595 wt % to 0.075 wt %; 0.00596 wt % to 0.074 wt %; 0.00597 wt % to 0.073 wt %; 0.00598 wt % to 0.072 wt %; 0.00599 wt % to 0.071 wt %; 0.006 wt % to 0.07 wt %; 0.00601 wt % to 0.069 wt %; 0.00602 wt % to 0.068 wt %; 0.00603 wt % to 0.067 wt %; 0.00604 wt % to 0.066 wt %; 0.00605 wt % to 0.065 wt %; 0.00606 wt % to 0.064 wt %; 0.00607 wt % to 0.063 wt %; 0.00608 wt % to 0.062 wt %; 0.00609 wt % to 0.061 wt %; 0.0061 wt % to 0.06 wt %; 0.00611 wt % to 0.059 wt %; 0.00612 wt % to 0.058 wt %; 0.00613 wt % to 0.057 wt %; 0.00614 wt % to 0.056 wt %; 0.00615 wt % to 0.055 wt %; 0.00616 wt % to 0.054 wt %; 0.00617 wt % to 0.053 wt %; 0.00618 wt % to 0.052 wt %; 0.00619 wt % to 0.051 wt %; 0.0062 wt % to 0.05 wt %; 0.00621 wt % to 0.049 wt %; 0.00622 wt % to 0.048 wt %; 0.00623 wt % to 0.047 wt %; 0.00624 wt % to 0.046 wt %; 0.00625 wt % to 0.045 wt %; 0.00626 wt % to 0.044 wt %; 0.00627 wt % to 0.043 wt %; 0.00628 wt % to 0.042 wt %; 0.00629 wt % to 0.041 wt %; 0.0063 wt % to 0.04 wt %; 0.00631 wt % to 0.0399 wt %; 0.00632 wt % to 0.0398 wt %; 0.00633 wt % to 0.0397 wt %; 0.00534 wt % to 0.0396 wt %; 0.00535 wt % to 0.0395 wt %; 0.00536 wt % to 0.0394 wt %; 0.00537 wt % to 0.0393 wt %; 0.00538 wt % to 0.0392 wt %; 0.00539 wt % to 0.0391 wt %; 0.0054 wt % to 0.039 wt %; 0.00541 wt % to 0.0389 wt %; 0.00542 wt % to 0.0388 wt %; 0.00543 wt % to 0.0387 wt %; 0.00544 wt % to 0.0386 wt %; 0.00545 wt % to 0.0385 wt %; 0.00546 wt % to 0.0384 wt %; 0.00547 wt % to 0.0383 wt %; 0.00548 wt % to 0.0382 wt %; 0.00549 wt % to 0.0381 wt %; 0.0055 wt % to 0.038 wt %; 0.00551 wt % to 0.0379 wt %; 0.00552 wt % to 0.0378 wt %; 0.00553 wt % to 0.0377 wt %; 0.00554 wt % to 0.0376 wt %; 0.00555 wt % to 0.0375 wt %; 0.00556 wt % to 0.0374 wt %; 0.00557 wt % to 0.0373 wt %; 0.00558 wt % to 0.0372 wt %; 0.00559 wt % to 0.0371 wt %; 0.0056 wt % to 0.037 wt %; 0.00561 wt % to 0.0369 wt %; 0.00562 wt % to 0.0368 wt %; 0.00563 wt % to 0.0367 wt %; 0.00564 wt % to 0.0366 wt %; 0.00565 wt % to 0.0365 wt %; 0.00566 wt % to 0.0364 wt %; 0.00567 wt % to 0.0363 wt %; 0.00568 wt % to 0.0362 wt %; 0.00569 wt % to 0.0361 wt %; 0.0057 wt % to 0.036 wt %; 0.00571 wt % to 0.0359 wt %; 0.00572 wt % to 0.0358 wt %; 0.00573 wt % to 0.0357 wt %; 0.00574 wt % to 0.0356 wt %; 0.00575 wt % to 0.0355 wt %; 0.00576 wt % to 0.0354 wt %; 0.00577 wt % to 0.0353 wt %; 0.00578 wt % to 0.0352 wt %; 0.00579 wt % to 0.0351 wt %; 0.0058 wt % to 0.035 wt %; 0.00581 wt % to 0.0349 wt %; 0.00582 wt % to 0.0348 wt %; 0.00583 wt % to 0.0347 wt %; 0.00584 wt % to 0.0346 wt %; 0.00585 wt % to 0.0345 wt %; 0.00586 wt % to 0.0344 wt %; 0.00587 wt % to 0.0343 wt %; 0.00588 wt % to 0.0342 wt %; 0.00589 wt % to 0.0341 wt %; 0.0059 wt % to 0.034 wt %; 0.00591 wt % to 0.0339 wt %; 0.00592 wt % to 0.0338 wt %; 0.00593 wt % to 0.0337 wt %; 0.00594 wt % to 0.0336 wt %; 0.00595 wt % to 0.0335 wt %; 0.00596 wt % to 0.0334 wt %; 0.00597 wt % to 0.0333 wt %; 0.00598 wt % to 0.0332 wt %; 0.00599 wt % to 0.0331 wt %; 0.0056 wt % to 0.033 wt %; 0.00561 wt % to 0.0329 wt %; 0.00562 wt % to 0.0328 wt %; 0.00563 wt % to 0.0327 wt %; 0.00564 wt % to 0.0326 wt %; 0.00565 wt % to 0.0325 wt %; 0.00566 wt % to 0.0324 wt %; 0.00567 wt % to 0.0323 wt %; 0.00568 wt % to 0.0322 wt %; 0.00569 wt % to 0.0321 wt %; 0.0057 wt % to 0.032 wt %; 0.00571 wt % to 0.0319 wt %; 0.00572 wt % to 0.0318 wt %; 0.00573 wt % to 0.0317 wt %; 0.00574 wt % to 0.0316 wt %; 0.00575 wt % to 0.0315 wt %; 0.00576 wt % to 0.0314 wt %; 0.00577 wt % to 0.0313 wt %; 0.00578 wt % to 0.0312 wt %; 0.00579 wt % to 0.0311 wt %; 0.0058 wt % to 0.031 wt %; 0.00581 wt % to 0.0309 wt %; 0.00582 wt % to 0.0308 wt %; 0.00583 wt % to 0.0307 wt %; 0.00584 wt % to 0.0306 wt %; 0.00585 wt % to 0.0305 wt %; 0.00586 wt % to 0.0304 wt %; 0.00587 wt % to 0.0303 wt %; 0.00588 wt % to 0.0302 wt %; 0.00589 wt % to 0.0301 wt %; 0.0059 wt % to 0.03 wt %; 0.00591 wt % to 0.0299 wt %; 0.00592 wt % to 0.0298 wt %; 0.00593 wt % to 0.0297 wt %; 0.00594 wt % to 0.0296 wt %; 0.00595 wt % to 0.0295 wt %; 0.00596 wt % to 0.0294 wt %; 0.00597 wt % to 0.0293 wt %; 0.00598 wt % to 0.0292 wt %; 0.00599 wt % to 0.0291 wt %; 0.006 wt % to 0.029 wt %; 0.00601 wt % to 0.0289 wt %; 0.00602 wt % to 0.0288 wt %; 0.00603 wt % to 0.0287 wt %; 0.00604 wt % to 0.0286 wt %; 0.00605 wt % to 0.0285 wt %; 0.00606 wt % to 0.0284 wt %; 0.00607 wt % to 0.0283 wt %; 0.00608 wt % to 0.0282 wt %; 0.00609 wt % to 0.0281 wt %; 0.0061 wt % to 0.028 wt %; 0.00611 wt % to 0.0279 wt %; 0.00612 wt % to 0.0278 wt %; 0.00613 wt % to 0.0277 wt %; 0.00614 wt % to 0.0276 wt %; 0.00615 wt % to 0.0275 wt %; 0.00616 wt % to 0.0274 wt %; 0.00617 wt % to 0.0273 wt %; 0.00618 wt % to 0.0272 wt %; 0.00619 wt % to 0.0271 wt %; 0.0062 wt % to 0.027 wt %; 0.00621 wt % to 0.0269 wt %; 0.00622 wt % to 0.0268 wt %; 0.00623 wt % to 0.0267 wt %; 0.00624 wt % to 0.0266 wt %; 0.00625 wt % to 0.0265 wt %; 0.00626 wt % to 0.0264 wt %; 0.00627 wt % to 0.0263 wt %; 0.00628 wt % to 0.0262 wt %; 0.00629 wt % to 0.0261 wt %; 0.0063 wt % to 0.026 wt %; 0.00631 wt % to 0.0259 wt %).

In additional embodiments, the formulation or the topical formulation described here comprises glutamine present at a weight percent (wt %) to the formulation of: 0.00584 wt % or greater (e.g., 0.0059; 0.006; 0.007; 0.008; 0.009; 0.01; 0.011; 0.012; 0.013; 0.014; 0.015; 0.016; 0.017; 0.018; 0.019; 0.02; 0.021; 0.022; 0.023; 0.024; 0.025; 0.026; 0.027; 0.028; 0.029; 0.03; 0.031; 0.032; 0.033; 0.034; 0.035; 0.036; 0.037; 0.038; 0.039; 0.04; 0.041; 0.042; 0.043; 0.044; 0.045; 0.046; 0.047; 0.048; 0.049; 0.05; 0.051; 0.052; 0.053; 0.054; 0.055; 0.056; 0.057; 0.058; 0.059; 0.06; 0.061; 0.062; 0.063; 0.064; 0.065; 0.066; 0.067; 0.068; 0.069; 0.07; 0.071; 0.072; 0.073; 0.074; 0.075; 0.076; 0.077; 0.078; 0.079; 0.08; 0.081; 0.082; 0.083; 0.084; 0.085; 0.086; 0.087; 0.088; 0.089; 0.09; 0.091; 0.092; 0.093; 0.094; 0.095; 0.096; 0.097; 0.098; 0.099; 0.1; 0.11; 0.12; 0.13; 0.14; 0.15; 0.16; 0.17; 0.18; 0.19; 0.2; 0.21; 0.22; 0.23; 0.24; 0.25; 0.26; 0.27; 0.28; 0.29; 0.3; 0.31; 0.32; 0.33; 0.34; 0.35; 0.36; 0.37; 0.38; 0.39; 0.4; 0.41; 0.42; 0.43; 0.44; 0.45; 0.46; 0.47; 0.48; 0.49; 0.5; 0.51; 0.52; 0.53; 0.54; 0.55; 0.56; 0.57; 0.58; 0.59; 0.6); 0.584 wt % or less (e.g., 0.583; 0.582; 0.581; 0.58; 0.579; 0.578; 0.577; 0.576; 0.575; 0.574; 0.573; 0.572; 0.571; 0.57; 0.569; 0.568; 0.567; 0.566; 0.565; 0.564; 0.563; 0.562; 0.561; 0.56; 0.559; 0.558; 0.557; 0.556; 0.554; 0.553; 0.552; 0.551; 0.55; 0.549; 0.548; 0.547; 0.546; 0.545; 0.544; 0.543; 0.542; 0.541; 0.54; 0.539; 0.538; 0.537; 0.536; 0.535; 0.534; 0.533; 0.532; 0.531; 0.53; 0.529; 0.528; 0.527; 0.526; 0.525; 0.524; 0.523; 0.522; 0.521; 0.52; 0.519; 0.518; 0.517; 0.516; 0.515; 0.514; 0.513; 0.512; 0.511; 0.51; 0.509; 0.508; 0.507; 0.506; 0.505; 0.504; 0.503; 0.502; 0.501; 0.5; 0.499; 0.498; 0.497; 0.496; 0.495; 0.494; 0.493; 0.492; 0.491; 0.49; 0.489; 0.488; 0.487; 0.486; 0.485; 0.484; 0.483; 0.482; 0.481; 0.48; 0.479; 0.478; 0.477; 0.476; 0.475; 0.474; 0.473; 0.472; 0.471; 0.47; 0.469; 0.468; 0.467; 0.466; 0.465; 0.464; 0.463; 0.462; 0.461; 0.46; 0.459; 0.458; 0.457; 0.456; 0.455; 0.454; 0.453; 0.452; 0.451; 0.45; 0.449; 0.448; 0.447; 0.446; 0.445; 0.444; 0.443; 0.442; 0.441; 0.44; 0.439; 0.438; 0.437; 0.436; 0.435; 0.434; 0.433; 0.432; 0.431; 0.43; 0.429; 0.428; 0.427; 0.426; 0.425; 0.424; 0.423; 0.422; 0.421; 0.42; 0.419; 0.418; 0.417; 0.416; 0.415; 0.414; 0.413; 0.412; 0.411; 0.41; 0.409; 0.408; 0.407; 0.406; 0.405; 0.404; 0.403; 0.402; 0.401; 0.4; 0.3; 0.2; 0.1; 0.09; 0.08; 0.07; 0.06; 0.05; 0.04; 0.03; 0.02; 0.01; 0.009; 0.008; 0.007; 0.006; 0.005; 0.004; 0.003; 0.002; 0.001); or 0.00584 wt % to 0.584 wt % (e.g., 0.00585 wt % to 0.582 wt %; 0.0059 wt % to 0.58 wt %; 0.0065 wt % to 0.578 wt %; 0.007 wt % to 0.576 wt %; 0.0075 wt % to 0.574 wt %; 0.008 wt % to 0.572 wt %; 0.0085 wt % to 0.57 wt %; 0.009 wt % to 0.568 wt %; 0.0095 wt % to 0.566 wt %; 0.01 wt % to 0.564 wt %; 0.015 wt % to 0.562 wt %; 0.02 wt % to 0.56 wt %; 0.025 wt % to 0.558 wt %; 0.03 wt % to 0.556 wt %; 0.035 wt % to 0.554 wt %; 0.04 wt % to 0.552 wt %; 0.045 wt % to 0.55 wt %; 0.05 wt % to 0.548 wt %; 0.055 wt % to 0.546 wt %; 0.06 wt % to 0.544 wt %; 0.065 wt % to 0.542 wt %; 0.07 wt % to 0.54 wt %; 0.075 wt % to 0.538 wt %; 0.08 wt % to 0.536 wt %; 0.085 wt % to 0.534 wt %; 0.09 wt % to 0.532 wt %; 0.095 wt % to 0.53 wt %; 0.1 wt % to 0.528 wt %; 0.15 wt % to 0.526 wt %; 0.2 wt % to 0.524 wt %; 0.25 wt % to 0.522 wt %; 0.3 wt % to 0.52 wt %; 0.35 wt % to 0.518 wt %; 0.4 wt % to 0.516 wt %; 0.45 wt % to 0.514 wt %; 0.5 wt % to 0.512 wt %).

Further embodiments described here provide the formulation or the topical formulation described here, wherein glycine is present at a weight percent (wt %) to the formulation of: 0.003 wt % or greater (e.g., 0.004; 0.005; 0.006; 0.007; 0.008; 0.009; 0.01; 0.02; 0.03; 0.04; 0.05; 0.06; 0.07; 0.08; 0.09; 0.1; 0.11; 0.12; 0.13; 0.14; 0.15; 0.16; 0.17; 0.18; 0.19; 0.2; 0.21; 0.22; 0.23; 0.24; 0.25; 0.26; 0.27; 0.28; 0.29; 0.3; 0.31; 0.32; 0.33; 0.34; 0.35; 0.36; 0.37; 0.38; 0.39; 0.4); 0.3 wt % or less (e.g., 0.298; 0.296; 0.294; 0.292; 0.29; 0.288; 0.286; 0.284; 0.282; 0.28; 0.278; 0.276; 0.274; 0.272; 0.27; 0.268; 0.266; 0.264; 0.262; 0.26; 0.258; 0.256; 0.254; 0.252; 0.25; 0.248; 0.246; 0.244; 0.242; 0.24; 0.238; 0.236; 0.234; 0.232; 0.23; 0.228; 0.226; 0.224; 0.222; 0.22; 0.218; 0.216; 0.214; 0.212; 0.21; 0.208; 0.206; 0.204; 0.202; 0.2; 0.198; 0.196; 0.194; 0.192; 0.19; 0.188; 0.186; 0.184; 0.182; 0.18; 0.178; 0.176; 0.174; 0.172; 0.17; 0.168; 0.166; 0.164; 0.162; 0.16; 0.158; 0.156; 0.154; 0.152; 0.15; 0.148; 0.146; 0.144; 0.142; 0.14; 0.138; 0.136; 0.134; 0.132; 0.13; 0.128; 0.126; 0.124; 0.122; 0.12; 0.118; 0.116; 0.114; 0.112; 0.11; 0.108; 0.106; 0.104; 0.102; 0.1; 0.098; 0.096; 0.094; 0.092; 0.09; 0.088; 0.086; 0.084; 0.082; 0.08; 0.078; 0.076; 0.074; 0.072; 0.07; 0.068; 0.066; 0.064; 0.062; 0.06; 0.058; 0.056; 0.054; 0.052; 0.05; 0.048; 0.046; 0.044; 0.042; 0.04; 0.038; 0.036; 0.034; 0.032; 0.03; 0.028; 0.026; 0.024; 0.022; 0.02; 0.018; 0.016; 0.014; 0.012; 0.01; 0.008; 0.006; 0.004; 0.002); or 0.003 wt % to 0.3 wt % (e.g., 0.0035 wt % to 0.29 wt %; 0.004 wt % to 0.27 wt %; 0.0045 wt % to 0.25 wt %; 0.005 wt % to 0.23 wt %; 0.0055 wt % to 0.21 wt %; 0.006 wt % to 0.19 wt %; 0.0065 wt % to 0.17 wt %; 0.007 wt % to 0.15 wt %; 0.0075 wt % to 0.13 wt %; 0.008 wt % to 0.11 wt %; 0.0085 wt % to 0.099 wt %; 0.009 wt % to 0.097 wt %; 0.0095 wt % to 0.095 wt %; 0.01 wt % to 0.093 wt %; 0.015 wt % to 0.091 wt %; 0.02 wt % to 0.089 wt %; 0.025 wt % to 0.087 wt %; 0.03 wt % to 0.085 wt %; 0.035 wt % to 0.083 wt %; 0.04 wt % to 0.081 wt %; 0.045 wt % to 0.079 wt %; 0.05 wt % to 0.077 wt %; 0.055 wt % to 0.075 wt %; 0.06 wt % to 0.073 wt %; 0.065 wt % to 0.071 wt %).

In some embodiments, the formulation or the topical formulation of the disclosure comprises serine present at a weight percent (wt %) to the formulation of: 0.0042 wt % or greater (e.g., 0.0044; 0.0046; 0.0048; 0.005; 0.0052; 0.0054; 0.0056; 0.0058; 0.006; 0.0062; 0.0064; 0.0066; 0.0068; 0.007; 0.0072; 0.0074; 0.0076; 0.0078; 0.008; 0.0082; 0.0084; 0.0086; 0.0088; 0.009; 0.0092; 0.0094; 0.0096; 0.0098; 0.01; 0.0102; 0.0104; 0.0106; 0.0108; 0.011; 0.0112; 0.0114; 0.0116; 0.0118; 0.012; 0.0122; 0.0124; 0.0126; 0.0128; 0.013; 0.0132; 0.0134; 0.0136; 0.0138; 0.014; 0.0142; 0.0144; 0.0146; 0.0148; 0.015; 0.0152; 0.0154; 0.0156; 0.0158; 0.016; 0.0162; 0.0164; 0.0166; 0.0168; 0.017; 0.0172; 0.0174; 0.0176; 0.0178; 0.018; 0.0182; 0.0184; 0.0186; 0.0188; 0.019; 0.0192; 0.0194; 0.0196; 0.0198; 0.02; 0.0202; 0.0204; 0.0206; 0.208; 0.021; 0.0212; 0.0214; 0.0216; 0.0218; 0.022; 0.0222; 0.0224; 0.0226; 0.0228; 0.023; 0.0232; 0.0234; 0.0236; 0.0238; 0.024; 0.0242; 0.0244; 0.0246; 0.0248; 0.025; 0.0252; 0.0254; 0.0256; 0.0258; 0.026; 0.0262; 0.0264; 0.0266; 0.0268; 0.027; 0.0272; 0.0274; 0.0276; 0.0278; 0.028; 0.0282; 0.0284; 0.0286; 0.0288; 0.029; 0.0292; 0.0294; 0.0296; 0.0298; 0.03; 0.0302; 0.0304; 0.0306; 0.0308; 0.031; 0.0312; 0.0314; 0.0316; 0.0318; 0.032; 0.0322; 0.0324; 0.0326; 0.0328; 0.033; 0.0332; 0.0334; 0.0336; 0.0338; 0.034; 0.0342; 0.0344; 0.0346; 0.0348; 0.035; 0.0352; 0.0354; 0.0356; 0.0358; 0.036; 0.0362; 0.0364; 0.0366; 0.0368; 0.037; 0.0372; 0.0374; 0.0376; 0.0378; 0.038; 0.0382; 0.0384; 0.0386; 0.0388; 0.039; 0.0392; 0.0394; 0.0396; 0.0398; 0.04; 0.0402; 0.0404; 0.0406; 0.0408; 0.041; 0.0412; 0.0414; 0.0416; 0.0418; 0.042; 0.0422; 0.0424; 0.0426; 0.0428; 0.043; 0.0432; 0.0434; 0.0436; 0.0438; 0.044; 0.0442; 0.0444; 0.0446; 0.0448; 0.045; 0.0452; 0.0454; 0.0456; 0.0458; 0.046; 0.0462; 0.0464; 0.0466; 0.0468; 0.047; 0.0472; 0.0474; 0.0476; 0.0478; 0.048; 0.0482; 0.0484; 0.0486; 0.0488; 0.049; 0.0492; 0.0494; 0.0496; 0.0498; 0.05; 0.0502; 0.0504; 0.0506; 0.0508; 0.051; 0.0512; 0.0514; 0.0516; 0.0518; 0.052; 0.0522; 0.0524; 0.0526; 0.0528; 0.053; 0.0532; 0.0534; 0.0536; 0.0538; 0.054; 0.0542; 0.0544; 0.0546; 0.0548; 0.055; 0.0552; 0.0554; 0.0556; 0.0558; 0.056;

0.0562; 0.0564; 0.0566; 0.0568; 0.057; 0.0572; 0.0574; 0.0576; 0.0578; 0.058; 0.0582; 0.0584; 0.0586; 0.0588; 0.059; 0.0592; 0.0594; 0.0596; 0.0598; 0.06; 0.0602; 0.0604; 0.0606; 0.0608; 0.061; 0.0612; 0.0614; 0.0616; 0.0618; 0.062; 0.0622; 0.0624; 0.0626; 0.0628; 0.063; 0.0632; 0.0634; 0.0636; 0.0638; 0.064; 0.0642; 0.0644; 0.0646; 0.0648; 0.065; 0.0652; 0.0654; 0.0656; 0.0658; 0.066; 0.0662; 0.0664; 0.0666; 0.0668; 0.067; 0.0672; 0.0674; 0.0676; 0.0678; 0.068; 0.0682; 0.0684; 0.0686; 0.0688; 0.069; 0.0692; 0.0694; 0.0696; 0.0698; 0.07; 0.0702; 0.0704; 0.0706; 0.0708; 0.071; 0.0712; 0.0714; 0.0716; 0.0718; 0.072; 0.0722; 0.0724; 0.0726; 0.0728; 0.073; 0.0732; 0.0734; 0.0736; 0.0738; 0.074; 0.0742; 0.0744; 0.0746; 0.0748; 0.075; 0.0752; 0.0754; 0.0756; 0.0758; 0.076; 0.0762; 0.0764; 0.0766; 0.0768; 0.077; 0.0772; 0.0774; 0.0776; 0.0778; 0.078; 0.0782; 0.0784; 0.0786; 0.0788; 0.079; 0.0792; 0.0794; 0.0796; 0.0798; 0.08; 0.0802; 0.0804; 0.0806; 0.0808; 0.081; 0.0812; 0.0814; 0.0816; 0.0818; 0.082; 0.0822; 0.0824; 0.0826; 0.0828; 0.083; 0.0832; 0.0834; 0.0836; 0.0838; 0.084; 0.0842; 0.0844; 0.0846; 0.0848; 0.085; 0.0852; 0.0854; 0.0856; 0.0858; 0.086; 0.0862; 0.0864; 0.0866; 0.0868; 0.087; 0.0872; 0.0874; 0.0876; 0.0878; 0.088; 0.0882; 0.0884; 0.0886; 0.0888; 0.089; 0.0892; 0.0894; 0.0896; 0.0898; 0.09; 0.0902; 0.0904; 0.0906; 0.0908; 0.091; 0.0912; 0.0914; 0.0916; 0.0918; 0.092; 0.0922; 0.0924; 0.0926; 0.0928; 0.093; 0.0932; 0.0934; 0.0936; 0.0938; 0.094; 0.0942; 0.0944; 0.0946; 0.0948; 0.095; 0.0952; 0.0954; 0.0956; 0.0958; 0.096; 0.0962; 0.0964; 0.0966; 0.0968; 0.097; 0.0972; 0.0974; 0.0976; 0.0978; 0.098; 0.0982; 0.0984; 0.0986; 0.0988; 0.099; 0.0992; 0.0994; 0.0996; 0.0998; 0.1; 0.102; 0.104; 0.106; 0.108; 0.11; 0.112; 0.114; 0.116; 0.118; 0.12; 0.122; 0.124; 0.126; 0.128; 0.13; 0.132; 0.134; 0.136; 0.138; 0.14; 0.142; 0.144; 0.146; 0.148; 0.15; 0.152; 0.154; 0.156; 0.158; 0.16; 0.162; 0.164; 0.166; 0.168; 0.17; 0.172; 0.174; 0.176; 0.178; 0.18; 0.182; 0.184; 0.186; 0.188; 0.19; 0.192; 0.194; 0.196; 0.198; 0.2; 0.22; 0.24; 0.26; 0.28; 0.3; 0.32; 0.34; 0.36; 0.38; 0.4; 0.42; 0.44; 0.46; 0.48; 0.5); 0.42 wt % or less (e.g., 0.418; 0.416; 0.414; 0.412; 0.41; 0.408; 0.406; 0.404; 0.402; 0.4; 0.398; 0.396; 0.394; 0.392; 0.39; 0.388; 0.386; 0.384; 0.382; 0.38; 0.378; 0.376; 0.374; 0.372; 0.37; 0.368; 0.366; 0.364; 0.362; 0.36; 0.358; 0.356; 0.354; 0.352; 0.35; 0.348; 0.346; 0.344; 0.342; 0.34; 0.338; 0.336; 0.334; 0.332; 0.33; 0.328; 0.326; 0.324; 0.322; 0.32; 0.318; 0.316; 0.314; 0.312; 0.31; 0.308; 0.306; 0.304; 0.302; 0.3; 0.298; 0.296; 0.294; 0.292; 0.294; 0.292; 0.29; 0.288; 0.286; 0.284; 0.282; 0.28; 0.278; 0.276; 0.274; 0.272; 0.27; 0.268; 0.266; 0.264; 0.262; 0.26; 0.258; 0.256; 0.254; 0.252; 0.25; 0.248; 0.246; 0.244; 0.242; 0.24; 0.238; 0.236; 0.234; 0.232; 0.23; 0.228; 0.226; 0.224; 0.222; 0.22; 0.218; 0.216; 0.214; 0.212; 0.21; 0.208; 0.206; 0.204; 0.202; 0.2; 0.198; 0.196; 0.194; 0.192; 0.19; 0.188; 0.186; 0.184; 0.182; 0.18; 0.178; 0.176; 0.174; 0.172; 0.17; 0.168; 0.166; 0.164; 0.162; 0.16; 0.158; 0.156; 0.154; 0.152; 0.15; 0.148; 0.146; 0.144; 0.142; 0.14; 0.138; 0.136; 0.134; 0.132; 0.13; 0.128; 0.126; 0.124; 0.122; 0.12; 0.118; 0.116; 0.114; 0.112; 0.11; 0.108; 0.106; 0.104; 0.102; 0.1; 0.098; 0.096; 0.094; 0.092; 0.09; 0.088; 0.086; 0.084; 0.082; 0.08; 0.078; 0.076; 0.074; 0.072; 0.07; 0.068; 0.066; 0.064; 0.062; 0.06; 0.058; 0.056; 0.054; 0.052; 0.05; 0.048; 0.046; 0.044; 0.042; 0.04; 0.038; 0.036; 0.034; 0.032; 0.03; 0.028; 0.026; 0.024; 0.022; 0.02; 0.018; 0.016; 0.014; 0.012; 0.01; 0.0088; 0.0086; 0.0084; 0.0082; 0.008; 0.0078; 0.0076; 0.0074; 0.0072; 0.007; 0.0068; 0.0066; 0.0064; 0.0062; 0.006; 0.0058; 0.0056; 0.0054; 0.0052; 0.005; 0.0048; 0.0046; 0.0044; 0.0042; 0.004); or 0.0042 wt % to 0.42 wt % (e.g., 0.0043 wt % to 0.415 wt %; 0.0045 wt % to 0.41 wt %; 0.0047 wt % to 0.405 wt %; 0.0049 wt % to 0.4 wt %; 0.0051 wt % to 0.395 wt %; 0.0053 wt % to 0.39 wt %; 0.0055 wt % to 0.385 wt %; 0.0057 wt % to 0.38 wt %; 0.0059 wt % to 0.375 wt %; 0.0061 wt % to 0.37 wt %; 0.0063 wt % to 0.365 wt %; 0.0065 wt % to 0.36 wt %; 0.0067 wt % to 0.355 wt %; 0.0069 wt % to 0.35 wt %; 0.0061 wt % to 0.345 wt %; 0.0063 wt % to 0.34 wt %; 0.0065 wt % to 0.335 wt %; 0.0067 wt % to 0.33 wt %; 0.0069 wt % to 0.325 wt %; 0.0071 wt % to 0.32 wt %; 0.0073 wt % to 0.315 wt %; 0.0075 wt % to 0.31 wt %; 0.0077 wt % to 0.305 wt %; 0.0079 wt % to 0.3 wt %; 0.0081 wt % to 0.295 wt %; 0.0083 wt % to 0.29 wt %; 0.0085 wt % to 0.285 wt %; 0.0087 wt % to 0.28 wt %; 0.0089 wt % to 0.275 wt %; 0.0091 wt % to 0.27 wt %; 0.0093 wt % to 0.265 wt %; 0.0095 wt % to 0.26 wt %; 0.0097 wt % to 0.255 wt %; 0.0099 wt % to 0.35 wt %; 0.0101 wt % to 0.345 wt %; 0.0103 wt % to 0.34 wt %; 0.0105 wt % to 0.335 wt %; 0.0107 wt % to 0.33 wt %; 0.0109 wt % to 0.325 wt %; 0.0111 wt % to 0.32 wt %; 0.0113 wt % to 0.315 wt %; 0.0115 wt % to 0.31 wt %; 0.0117 wt % to 0.305 wt %; 0.0119 wt % to 0.3 wt %; 0.0121 wt % to 0.295 wt %; 0.0123 wt % to 0.29 wt %; 0.0125 wt % to 0.285 wt %; 0.0127 wt % to 0.28 wt %; 0.0129 wt % to 0.275 wt %; 0.0131 wt % to 0.27 wt %; 0.0133 wt % to 0.265 wt %; 0.0135 wt % to 0.26 wt %; 0.0137 wt % to 0.255 wt %; 0.0139 wt % to 0.25 wt %; 0.0141 wt % to 0.245 wt %; 0.0143 wt % to 0.24 wt %; 0.0145 wt % to 0.235 wt %; 0.0147 wt % to 0.23 wt %; 0.0149 wt % to 0.225 wt %; 0.0151 wt % to 0.22 wt %; 0.0153 wt % to 0.215 wt %; 0.0155 wt % to 0.21 wt %; 0.0157 wt % to 0.205 wt %; 0.0159 wt % to 0.2 wt %; 0.0161 wt % to 0.195 wt %; 0.0163 wt % to 0.19 wt %; 0.0165 wt % to 0.185 wt %; 0.0167 wt % to 0.18 wt %; 0.0169 wt % to 0.175 wt %; 0.0171 wt % to 0.17 wt %; 0.0173 wt % to 0.165 wt %; 0.0175 wt % to 0.16 wt %; 0.0177 wt % to 0.155 wt %; 0.0179 wt % to 0.15 wt %; 0.0181 wt % to 0.145 wt %; 0.0183 wt % to 0.14 wt %; 0.0185 wt % to 0.135 wt %; 0.0187 wt % to 0.13 wt %; 0.0189 wt % to 0.125 wt %; 0.0191 wt % to 0.12 wt %; 0.0193 wt % to 0.115 wt %; 0.0195 wt % to 0.11 wt %; 0.0197 wt % to 0.105 wt %; 0.0199 wt % to 0.1 wt %; 0.0201 wt % to 0.095 wt %; 0.0203 wt % to 0.09 wt %; 0.0205 wt % to 0.085 wt %; 0.0207 wt % to 0.08 wt %; 0.0209 wt % to 0.075 wt %; 0.0211 wt % to 0.07 wt %; 0.0213 wt % to 0.065 wt %; 0.0215 wt % to 0.06 wt %; 0.0217 wt % to 0.055 wt %; 0.0219 wt % to 0.05 wt %; 0.0221 wt % to 0.045 wt %; 0.0223 wt % to 0.04 wt %; 0.0225 wt % to 0.035 wt %; 0.0227 wt % to 0.03 wt %; 0.0229 wt % to 0.025 wt %).

Additional embodiments described here provides the formulation or the topical formulation disclosed here, where the amino acid combination comprises, consists essentially of, or consists of: alanine (4 mM) of 0.0356%; glutamine (4 mM) of 0.0584%; glycine (4 mM) of 0.03%; and serine (4 mM) of 0.042%.

Other embodiments described here provide the formulation or the topical formulation disclosed here, wherein the therapeutically effective amount of a combination of free amino acids comprises (or consists essentially of or consists of): Alanine (Ala), Glutamine (Gln), Glycine (Gly), and Serine (Ser), wherein each free amino acid comprises a ratio to each of the other free amino acids of: 1:100 [0.1 to 10] or greater (e.g., 1 (Ala):100 (Gln):100 (Gly):100 (Ser) [0.1 to 10]; 100 (Ala):1 (Gln):100 (Gly):100 (Ser) [0.1 to 10]; 100 (Ala):100 (Gln):1 (Gly):100 (Ser) [0.1 to 10]; 100 (Ala):100 (Gln):100 (Gly):1 (Ser) [0.1 to 10]; 1 (Ala):90 (Gln):90 (Gly):90 (Ser) [0.1 to 9]; 90 (Ala):90 (Gln):90 (Gly):90 (Ser) [0.1 to 9]; 90 (Ala):90 (Gln):1 (Gly):90 (Ser) [0.1 to 9]; 90 (Ala):90 (Gln):90 (Gly):1 (Ser) [0.1 to 9]; 1 (Ala):80 (Gln):80 (Gly):80 (Ser) [0.1 to 8]; 80 (Ala):1 (Gln):80 (Gly):80

(Ser) [0.1 to 8]; 80 (Ala):80 (Gln):1 (Gly):80 (Ser) [0.1 to 8]; 80 (Ala):80 (Gln):80 (Gly):1 (Ser) [0.1 to 8]; 1 (Ala):70 (Gln):70 (Gly):70 (Ser) [0.1 to 7]; 70 (Ala):1 (Gln):70 (Gly):70 (Ser) [0.1 to 7]; 70 (Ala):70 (Gln):1 (Gly):70 (Ser) [0.1 to 7]; 70 (Ala):70 (Gln):70 (Gly):1 (Ser) [0.1 to 7]; 1 (Ala):60 (Gln):60 (Gly):60 (Ser) [0.1 to 6]; 60 (Ala):1 (Gln):60 (Gly):60 (Ser) [0.1 to 6]; 60 (Ala):60 (Gln):1 (Gly):60 (Ser) [0.1 to 6]; 60 (Ala):60 (Gln):60 (Gly):1 (Ser) [0.1 to 6]; 1 (Ala):50 (Gln):50 (Gly):50 (Ser) [0.1 to 5]; 50 (Ala):1 (Gln):50 (Gly):50 (Ser) [0.1 to 5]; 50 (Ala):50 (Gln):1 (Gly):50 (Ser) [0.1 to 5]; 50 (Ala):50 (Gln):50 (Gly):1 (Ser) [0.1 to 5]; 1 (Ala):40 (Gln):40 (Gly):40 (Ser) [0.1 to 4]; 40 (Ala):1 (Gln):40 (Gly):40 (Ser) [0.1 to 4]; 40 (Ala):40 (Gln):1 (Gly):40 (Ser) [0.1 to 4]; 40 (Ala):40 (Gln):40 (Gly):1 (Ser) [0.1 to 4]; 1 (Ala):30 (Gln):30 (Gly):30 (Ser) [0.1 to 3]; 30 (Ala):1 (Gln):30 (Gly):30 (Ser) [0.1 to 3]; 30 (Ala):30 (Gln):1 (Gly):30 (Ser) [0.1 to 3]; 30 (Ala):30 (Gln):30 (Gly):1 (Ser) [0.1 to 3]; 1 (Ala):20 (Gln):20 (Gly):20 (Ser) [0.1 to 2]; 20 (Ala):1 (Gln):20 (Gly):20 (Ser) [0.1 to 2]; 20 (Ala):20 (Gln):1 (Gly):20 (Ser) [0.1 to 2]; 20 (Ala):20 (Gln):20 (Gly):1 (Ser) [0.1 to 2]; 1 (Ala):10 (Gln):10 (Gly):10 (Ser) [0.1 to 1]; 10 (Ala):1 (Gln):10 (Gly):10 (Ser) [0.1 to 1]; 10 (Ala):10 (Gln):1 (Gly):10 (Ser) [0.1 to 1]; 10 (Ala):10 (Gln):10 (Gly):1 (Ser) [0.1 to 1]; 1 (Ala):5 (Gln):5 (Gly):5 (Ser) [0.1 to 0.5]; 5 (Ala):1 (Gln):5 (Gly):5 (Ser) [0.1 to 0.5]; 5 (Ala):5 (Gln):1 (Gly):5 (Ser) [0.1 to 0.5]; 5 (Ala):5 (Gln):5 (Gly):1 (Ser) [0.1 to 0.5]; 2 (Ala):5 (Gln):5 (Gly):5 (Ser) [0.1 to 0.25]; 5 (Ala):2 (Gln):5 (Gly):5 (Ser) [0.1 to 0.25]; 5 (Ala):5 (Gln):2 (Gly):5 (Ser) [0.1 to 0.25]; 5 (Ala):5 (Gln):5 (Gly):2 (Ser) [0.1 to 0.25]; 1 (Ala):1 (Gln):1 (Gly):1 (Ser) [0.1 to 0.1]; 2 (Ala):1 (Gln):1 (Gly):1 (Ser) [0.2 to 0.1]; 1 (Ala):2 (Gln):1 (Gly):1 (Ser) [0.2 to 0.1]; 1 (Ala):1 (Gln):2 (Gly):1 (Ser) [0.2 to 0.1]; 1 (Ala):1 (Gln):1 (Gly):2 (Ser) [0.2 to 0.1]; 3 (Ala):1 (Gln):1 (Gly):1 (Ser) [0.3 to 0.1]; 1 (Ala):3 (Gln):1 (Gly):1 (Ser) [0.3 to 0.1]; 1 (Ala):1 (Gln):3 (Gly):1 (Ser) [0.3 to 0.1]; 1 (Ala):1 (Gln):1 (Gly):3 (Ser) [0.3 to 0.1]; 4 (Ala):1 (Gln):1 (Gly):1 (Ser) [0.4 to 0.1]; 1 (Ala):4 (Gln):1 (Gly):1 (Ser) [0.4 to 0.1]; 1 (Ala):1 (Gln):4 (Gly):1 (Ser) [0.4 to 0.1]; 1 (Ala):1 (Gln):1 (Gly):4 (Ser) [0.4 to 0.1]; 1 (Ala):5 (Gln):5 (Gly):5 (Ser) [0.5 to 0.1]; 1 (Ala):5 (Gln):1 (Gly):1 (Ser) [0.5 to 0.1]; 1 (Ala):1 (Gln):5 (Gly):1 (Ser) [0.5 to 0.1]; 1 (Ala):1 (Gln):1 (Gly):5 (Ser) [0.5 to 0.1]; 6 (Ala):1 (Gln):1 (Gly):1 (Ser) [0.6 to 0.1]; 1 (Ala):6 (Gln):1 (Gly):1 (Ser) [0.6 to 0.1]; 1 (Ala):1 (Gln):6 (Gly):1 (Ser) [0.6 to 0.1]; 1 (Ala):1 (Gln):1 (Gly):6 (Ser) [0.6 to 0.1]; 7 (Ala):1 (Gln):1 (Gly):1 (Ser) [0.7 to 0.1]; 1 (Ala):7 (Gln):1 (Gly):1 (Ser) [0.7 to 0.1]; 1 (Ala):1 (Gln):7 (Gly):1 (Ser) [0.7 to 0.1]; 1 (Ala):1 (Gln):1 (Gly):7 (Ser) [0.7 to 0.1]; 8 (Ala):1 (Gln):1 (Gly):1 (Ser) [0.8 to 0.1]; 1 (Ala):8 (Gln):1 (Gly):1 (Ser) [0.8 to 0.1]; 1 (Ala):1 (Gln):8 (Gly):1 (Ser) [0.8 to 0.1]; 1 (Ala):1 (Gln):1 (Gly):8 (Ser) [0.8 to 0.1]; 9 (Ala):1 (Gln):1 (Gly):1 (Ser) [0.9 to 0.1]; 1 (Ala):9 (Gln):1 (Gly):1 (Ser) [0.9 to 0.1]; 1 (Ala):1 (Gln):9 (Gly):1 (Ser) [0.9 to 0.1]; 1 (Ala):1 (Gln):1 (Gly):9 (Ser) [0.9 to 0.1]; 10 (Ala):1 (Gln):1 (Gly):1 (Ser) [1 to 0.1]; 1 (Ala):10 (Gln):1 (Gly):1 (Ser) [1 to 0.1]; 1 (Ala):1 (Gln):10 (Gly):1 (Ser) [1 to 0.1]; 1 (Ala):1 (Gln):1 (Gly):10 (Ser) [1 to 0.1]; 20 (Ala):1 (Gln):1 (Gly):1 (Ser) [2 to 0.1]; 1 (Ala):20 (Gln):1 (Gly):1 (Ser) [2 to 0.1]; 1 (Ala):1 (Gln):20 (Gly):1 (Ser) [2 to 0.1]; 1 (Ala):1 (Gln):1 (Gly):20 (Ser) [2 to 0.1]; 30 (Ala):1 (Gln):1 (Gly):1 (Ser) [3 to 0.1]; 1 (Ala):30 (Gln):1 (Gly):1 (Ser) [3 to 0.1]; 1 (Ala):1 (Gln):30 (Gly):1 (Ser) [3 to 0.1]; 1 (Ala):1 (Gln):1 (Gly):30 (Ser) [3 to 0.1]; 40 (Ala):1 (Gln):1 (Gly):1 (Ser) [4 to 0.1]; 1 (Ala):40 (Gln):1 (Gly):1 (Ser) [4 to 0.1]; 1 (Ala):1 (Gln):40 (Gly):1 (Ser) [4 to 0.1]; 1 (Ala):1 (Gln):1 (Gly):40 (Ser) [4 to 0.1]; 50 (Ala):1 (Gln):1 (Gly):1 (Ser) [5 to 0.1]; 1 (Ala):50 (Gln):1 (Gly):1 (Ser) [5 to 0.1]; 1 (Ala):1 (Gln):50 (Gly):1 (Ser) [5 to 0.1]; 1 (Ala):1 (Gln):1 (Gly):50 (Ser) [5 to 0.1]; 60 (Ala):1 (Gln):1 (Gly):1 (Ser) [6 to 0.1]; 1 (Ala):60 (Gln):1 (Gly):1 (Ser) [6 to 0.1]; 1 (Ala):1 (Gln):60 (Gly):1 (Ser) [6 to 0.1]; 1 (Ala):1 (Gln):1 (Gly):60 (Ser) [6 to 0.1]; 70 (Ala):1 (Gln):1 (Gly):1 (Ser) [7 to 0.1]; 1 (Ala):70 (Gln):1 (Gly):1 (Ser) [7 to 0.1]; 1 (Ala):1 (Gln):70 (Gly):1 (Ser) [7 to 0.1]; 1 (Ala):1 (Gln):1 (Gly):70 (Ser) [7 to 0.1]; 80 (Ala):1 (Gln):1 (Gly):1 (Ser) [8 to 0.1]; 1 (Ala):80 (Gln):1 (Gly):1 (Ser) [8 to 0.1]; 1 (Ala):1 (Gln):80 (Gly):1 (Ser) [8 to 0.1]; 1 (Ala):1 (Gln):1 (Gly):80 (Ser) [8 to 0.1]; 90 (Ala):1 (Gln):1 (Gly):1 (Ser) [9 to 0.1]; 1 (Ala):90 (Gln):1 (Gly):1 (Ser) [9 to 0.1]; 1 (Ala):1 (Gln):90 (Gly):1 (Ser) [9 to 0.1]; 1 (Ala):1 (Gln):1 (Gly):90 (Ser) [9 to 0.1]; 100 (Ala):1 (Gln):1 (Gly):1 (Ser) [10 to 0.1]; 1 (Ala):100 (Gln):1 (Gly):1 (Ser) [10 to 0.1]; 1 (Ala):1 (Gln):100 (Gly):1 (Ser) [10 to 0.1]; 1 (Ala):1 (Gln):1 (Gly):100 (Ser) [10 to 0.1]); 100:1 [10 to 0.1] or less (e.g., 95 (Ala):1 (Gln):1 (Gly):1 (Ser) [9.5 to 0.1]; 1 (Ala):95 (Gln):1 (Gly):1 (Ser) [9.5 to 0.1]; 1 (Ala):1 (Gln):95 (Gly):1 (Ser) [9.5 to 0.1]; 1 (Ala):1 (Gln):1 (Gly):95 (Ser) [9.5 to 0.1]; 85 (Ala):1 (Gln):1 (Gly):1 (Ser) [8.5 to 0.1]; 1 (Ala):85 (Gln):1 (Gly):1 (Ser) [8.5 to 0.1]; 1 (Ala):1 (Gln):85 (Gly):1 (Ser) [8.5 to 0.1]; 1 (Ala):1 (Gln):1 (Gly):85 (Ser) [8.5 to 0.1]; 75 (Ala):1 (Gln):1 (Gly):1 (Ser) [7.5 to 0.1]; 1 (Ala):75 (Gln):1 (Gly):1 (Ser) [7.5 to 0.1]; 1 (Ala):1 (Gln):75 (Gly):1 (Ser) [5.5 to 0.1]; 1 (Ala):1 (Gln):1 (Gly):55 (Ser) [5.5 to 0.1]; 65 (Ala):1 (Gln):1 (Gly):1 (Ser) [6.5 to 0.1]; 1 (Ala):65 (Gln):1 (Gly):1 (Ser) [6.5 to 0.1]; 1 (Ala):1 (Gln):65 (Gly):1 (Ser) [6.5 to 0.1]; 1 (Ala):1 (Gln):1 (Gly):65 (Ser) [6.5 to 0.1]; 55 (Ala):1 (Gln):1 (Gly):1 (Ser) [5.5 to 0.1]; 1 (Ala):55 (Gln):1 (Gly):1 (Ser) [5.5 to 0.1]; 1 (Ala):1 (Gln):55 (Gly):1 (Ser) [5.5 to 0.1]; 1 (Ala):1 (Gln):1 (Gly):55 (Ser) [5.5 to 0.1]; 45 (Ala):1 (Gln):1 (Gly):1 (Ser) [4.5 to 0.1]; 1 (Ala):45 (Gln):1 (Gly):1 (Ser) [4.5 to 0.1]; 1 (Ala):1 (Gln):45 (Gly):1 (Ser) [4.5 to 0.1]; 1 (Ala):1 (Gln):1 (Gly):45 (Ser) [4.5 to 0.1]; 35 (Ala):1 (Gln):1 (Gly):1 (Ser) [3.5 to 0.1]; 1 (Ala):35 (Gln):1 (Gly):1 (Ser) [3.5 to 0.1]; 1 (Ala):1 (Gln):35 (Gly):1 (Ser) [3.5 to 0.1]; 1 (Ala):1 (Gln):1 (Gly):35 (Ser) [3.5 to 0.1]; 25 (Ala):1 (Gln):1 (Gly):1 (Ser) [2.5 to 0.1]; 1 (Ala):25 (Gln):1 (Gly):1 (Ser) [2.5 to 0.1]; 1 (Ala):1 (Gln):25 (Gly):1 (Ser) [2.5 to 0.1]; 1 (Ala):1 (Gln):1 (Gly):25 (Ser) [0.1 to 0.5]; 15 (Ala):1 (Gln):1 (Gly):1 (Ser) [1.5 to 0.1]; 1 (Ala):15 (Gln):1 (Gly):1 (Ser) [1.5 to 0.1]; 1 (Ala):1 (Gln):15 (Gly):1 (Ser) [1.5 to 0.1]; 1 (Ala):1 (Gln):1 (Gly):15 (Ser) [1.5 to 0.1]; 14 (Ala):1 (Gln):1 (Gly):1 (Ser) [1.4 to 0.1]; 1 (Ala):14 (Gln):1 (Gly):1 (Ser) [1.4 to 0.1]; 1 (Ala):1 (Gln):14 (Gly):1 (Ser) [1.4 to 0.1]; 1 (Ala):1 (Gln):1 (Gly):14 (Ser) [1.4 to 0.1]; 13 (Ala):1 (Gln):1 (Gly):1 (Ser) [1.3 to 0.1]; 1 (Ala):13 (Gln):1 (Gly):1 (Ser) [1.3 to 0.1]; 1 (Ala):1 (Gln):13 (Gly):1 (Ser) [1.3 to 0.1]; 1 (Ala):1 (Gln):1 (Gly):13 (Ser) [1.3 to 0.1]; 12 (Ala):1 (Gln):1 (Gly):1 (Ser) [1.2 to 0.1]; 1 (Ala):12 (Gln):1 (Gly):1 (Ser) [1.2 to 0.1]; 1 (Ala):1 (Gln):12 (Gly):1 (Ser) [1.2 to 0.1]; 1 (Ala):1 (Gln):1 (Gly):12 (Ser) [1.2 to 0.1]; 11 (Ala):1 (Gln):1 (Gly):1 (Ser) [1.1 to 0.1]; 1 (Ala):11 (Gln):1 (Gly):1 (Ser) [1.1 to 0.1]; 1 (Ala):1 (Gln):11 (Gly):1 (Ser) [1.1 to 0.1]; 1 (Ala):1 (Gln):1 (Gly):11 (Ser) [1.1 to 0.1]; 10 (Ala):1 (Gln):1 (Gly):1 (Ser) [1 to 0.1]; 1 (Ala):10 (Gln):1 (Gly):1 (Ser) [1 to 0.1]; 1 (Ala):1 (Gln):10 (Gly):1 (Ser) [1 to 0.1]; 1 (Ala):1 (Gln):1 (Gly):10 (Ser) [1 to 0.1]; 19 (Ala):2 (Gln):2 (Gly):2 (Ser) [0.95 to 0.1]; 2 (Ala):19 (Gln):2 (Gly):2 (Ser) [0.95 to 0.1]; 2 (Ala):2 (Gln):19 (Gly):2 (Ser) [0.95 to 0.1]; 2 (Ala):2 (Gln):2 (Gly):19 (Ser) [0.95 to 0.1]; 17 (Ala):2 (Gln):2 (Gly):2 (Ser) [0.85 to 0.1]; 2 (Ala):17 (Gln):2 (Gly):2 (Ser) [0.85 to 0.1]; 2 (Ala):2 (Gln):17 (Gly):2 (Ser) [0.85 to 0.1]; 2 (Ala):2 (Gln):2 (Gly):17 (Ser) [0.85 to 0.1]; 15 (Ala):2 (Gln):2 (Gly):2 (Ser) [0.75 to 0.1];

2 (Ala):15 (Gln):2 (Gly):2 (Ser) [0.75 to 0.1]; 2 (Ala):2 (Gln):15 (Gly):2 (Ser) [0.75 to 0.1]; 2 (Ala):2 (Gln):2 (Gly):15 (Ser) [0.75 to 0.1]; 13 (Ala):2 (Gln):2 (Gly):2 (Ser) [0.65 to 0.1]; 2 (Ala):13 (Gln):2 (Gly):2 (Ser) [0.65 to 0.1]; 2 (Ala):2 (Gln):13 (Gly):2 (Ser) [0.65 to 0.1]; 2 (Ala):2 (Gln):2 (Gly):13 (Ser) [0.65 to 0.1]; 11 (Ala):2 (Gln):2 (Gly):2 (Ser) [0.55 to 0.1]; 2 (Ala):11 (Gln):2 (Gly):2 (Ser) [0.55 to 0.1]; 2 (Ala):2 (Gln):11 (Gly):2 (Ser) [0.55 to 0.1]; 2 (Ala):2 (Gln):2 (Gly):11 (Ser) [0.55 to 0.1]; 9 (Ala):2 (Gln):2 (Gly):2 (Ser) [0.45 to 0.1]; 2 (Ala):9 (Gln):2 (Gly):2 (Ser) [0.45 to 0.1]; 2 (Ala):2 (Gln):9 (Gly):2 (Ser) [0.45 to 0.1]; 2 (Ala):2 (Gln):2 (Gly):9 (Ser) [0.45 to 0.1]; 7 (Ala):2 (Gln):2 (Gly):2 (Ser) [0.35 to 0.1]; 2 (Ala):7 (Gln):2 (Gly):2 (Ser) [0.35 to 0.1]; 2 (Ala):2 (Gln):7 (Gly):2 (Ser) [0.35 to 0.1]; 2 (Ala):2 (Gln):2 (Gly):7 (Ser) [0.35 to 0.1]; 5 (Ala):2 (Gln):2 (Gly):2 (Ser) [0.25 to 0.1]; 2 (Ala):5 (Gln):2 (Gly):2 (Ser) [0.25 to 0.1]; 2 (Ala):2 (Gln):5 (Gly):2 (Ser) [0.25 to 0.1]; 2 (Ala):2 (Gln):2 (Gly):5 (Ser) [0.25 to 0.1]; 3 (Ala):2 (Gln):2 (Gly):2 (Ser) [0.15 to 0.1]; 2 (Ala):3 (Gln):2 (Gly):2 (Ser) [0.15 to 0.1]; 2 (Ala):2 (Gln):3 (Gly):2 (Ser) [0.15 to 0.1]; 2 (Ala):2 (Gln):2 (Gly):3 (Ser) [0.15 to 0.1]; 2 (Ala):3 (Gln):3 (Gly):3 (Ser) [0.1 to 0.15]; 3 (Ala):2 (Gln):3 (Gly):3 (Ser) [0.1 to 0.15]; 3 (Ala):3 (Gln):2 (Gly):3 (Ser) [0.1 to 0.15]; 3 (Ala):3 (Gln):3 (Gly):2 (Ser) [0.1 to 0.15]; 2 (Ala):5 (Gln):5 (Gly):5 (Ser) [0.1 to 0.25]; 5 (Ala):2 (Gln):5 (Gly):5 (Ser) [0.1 to 0.25]; 5 (Ala):5 (Gln):2 (Gly):5 (Ser) [0.1 to 0.25]; 5 (Ala):5 (Gln):5 (Gly):2 (Ser) [0.1 to 0.25]; 2 (Ala):7 (Gln):7 (Gly):7 (Ser) [0.1 to 0.35]; 7 (Ala):2 (Gln):7 (Gly):7 (Ser) [0.1 to 0.35]; 7 (Ala):7 (Gln):2 (Gly):7 (Ser) [0.1 to 0.35]; 7 (Ala):7 (Gln):7 (Gly):2 (Ser) [0.1 to 0.35]; 2 (Ala):9 (Gln):9 (Gly):9 (Ser) [0.1 to 0.45]; 9 (Ala):2 (Gln):9 (Gly):9 (Ser) [0.1 to 0.45]; 9 (Ala):9 (Gln):2 (Gly):9 (Ser) [0.1 to 0.45]; 9 (Ala):9 (Gln):9 (Gly):2 (Ser) [0.1 to 0.45]; 2 (Ala):11 (Gln):11 (Gly):11 (Ser) [0.1 to 0.55]; 11 (Ala):2 (Gln):11 (Gly):11 (Ser) [0.1 to 0.55]; 11 (Ala):11 (Gln):2 (Gly):11 (Ser) [0.1 to 0.55]; 11 (Ala):11 (Gln):11 (Gly):2 (Ser) [0.1 to 0.55]; 2 (Ala):13 (Gln):13 (Gly):13 (Ser) [0.1 to 0.65]; 13 (Ala):2 (Gln):13 (Gly):13 (Ser) [0.1 to 0.65]; 13 (Ala):13 (Gln):2 (Gly):13 (Ser) [0.1 to 0.65]; 13 (Ala):13 (Gln):13 (Gly):2 (Ser) [0.1 to 0.65]; 2 (Ala):15 (Gln):15 (Gly):15 (Ser) [0.1 to 0.75]; 15 (Ala):2 (Gln):15 (Gly):15 (Ser) [0.1 to 0.75]; 15 (Ala):15 (Gln):2 (Gly):15 (Ser) [0.1 to 0.75]; 15 (Ala):15 (Gln):15 (Gly):2 (Ser) [0.1 to 0.75]; 2 (Ala):17 (Gln):17 (Gly):17 (Ser) [0.1 to 0.85]; 17 (Ala):2 (Gln):17 (Gly):17 (Ser) [0.1 to 0.85]; 17 (Ala):17 (Gln):2 (Gly):17 (Ser) [0.1 to 0.85]; 17 (Ala):17 (Gln):17 (Gly):2 (Ser) [0.1 to 0.85]; 2 (Ala):19 (Gln):19 (Gly):19 (Ser) [0.1 to 0.95]; 19 (Ala):2 (Gln):19 (Gly):19 (Ser) [0.1 to 0.95]; 19 (Ala):19 (Gln):2 (Gly):19 (Ser) [0.1 to 0.95]; 19 (Ala):19 (Gln):19 (Gly):2 (Ser) [0.1 to 0.95]); or from 1:100 to 100:1 (e.g., 1 (Ala):100 (Gln):100 (Gly):100 (Ser) [0.1 to 10] to 100 (Ala):1 (Gln):1 (Gly):1 (Ser) [10 to 0.1]; 100 (Ala):1 (Gln):100 (Gly):100 (Ser) [0.1 to 10] to 1 (Ala):100 (Gln):1 (Gly):1 (Ser) [10 to 0.1]; 100 (Ala):100 (Gln):1 (Gly):100 (Ser) [0.1 to 10] to 1 (Ala):1 (Gln):100 (Gly):1 (Ser) [10 to 0.1]; 100 (Ala):100 (Gln):100 (Gly):1 (Ser) [0.1 to 10] to 1 (Ala):1 (Gln):1 (Gly):100 (Ser) [10 to 0.1]).

In additional embodiments, the formulation or the topical formulation described here comprising the therapeutically effective amount of the plant extract (e.g., *Boswellia* extract (e.g., *Boswellia serrata*; Burseraceae family; olibanum; frankincense) or plant extract combination (e.g., BOSEXIL® (INDENA SpA) or *Boswellia serrata* resin extract, cellulose (microcrystalline), lecithin, silica), comprising (or consisting essentially of, or consisting of): *Boswellia* extract (e.g., *Boswellia serrata*; Burseraceae family; olibanum; frankincense); a texturing and/or a bulking agent (e.g., cellulose (microcrystalline)); an emulsifier or a phospholipid, where in some embodiments, phospholipids are used as an emulsifier (e.g., lecithin or phosphatidylcholine); and an anti-caking agent (e.g., silica, adsorbs water in hygroscopic applications); and optionally, a dermatologically acceptable carrier and/or additive, where the plant extract or the plant extract combination is present at a weight percentage (w/w %) of the formulation of: 0.025 w/w % or greater (e.g., 0.027; 0.029; 0.031; 0.033; 0.035; 0.037; 0.039; 0.041; 0.043; 0.045; 0.047; 0.049; 0.051; 0.053; 0.055; 0.057; 0.059; 0.061; 0.063; 0.065; 0.067; 0.069; 0.071; 0.073; 0.075; 0.077; 0.079; 0.081; 0.083; 0.085; 0.087; 0.089; 0.091; 0.093; 0.095; 0.097; 0.099; 0.1; 0.15; 0.3; 0.35; 0.5; 0.55; 0.7; 0.75; 0.9; 0.95; 1.1; 1.3; 1.5; 1.7; 1.9; 2.1; 2.3; 2.5; 2.7; 2.9; 3.1; 3.3; 3.5; 3.7; 3.9; 4.1; 4.3; 4.5; 4.7; 4.9; 5.1; 5.3); 5 w/w % or less (e.g., 4.8; 4.6; 4.4; 4.2; 4; 3.8; 3.6; 3.4; 3.2; 3; 2.8; 2.6; 2.4; 2.2; 2; 1.8; 1.6; 1.4; 1.2; 1; 0.85; 0.8; 0.65; 0.6; 0.45; 0.4; 0.25; 0.2; 0.098; 0.096; 0.094; 0.092; 0.09; 0.088; 0.086; 0.084; 0.082; 0.08; 0.078; 0.076; 0.074; 0.072; 0.07; 0.068; 0.066; 0.064; 0.062; 0.06; 0.058; 0.056; 0.054; 0.052; 0.05; 0.048; 0.046; 0.044; 0.042; 0.04; 0.038; 0.036; 0.034; 0.032; 0.03; 0.028; 0.026; 0.024; 0.022; 0.02; 0.018); or 0.025 w/w %-5 w/w % (e.g., 0.026 w/w %-4.9 w/w %; 0.027 w/w %-4.8 w/w %; 0.028 w/w %-4.7 w/w %; 0.029 w/w %-4.6 w/w %; 0.03 w/w %-4.5 w/w %; 0.031 w/w %-4.4 w/w %; 0.032 w/w %-4.3 w/w %; 0.033 w/w %-4.2 w/w %; 0.034 w/w %-4.1 w/w %; 0.035 w/w %-4 w/w %; 0.036 w/w %-3.9 w/w %; 0.037 w/w %-3.8 w/w %; 0.038 w/w %-3.7 w/w %; 0.039 w/w %-3.6 w/w %; 0.04 w/w %-3.5 w/w %; 0.041 w/w %-3.4 w/w %; 0.042 w/w %-3.3 w/w %; 0.043 w/w %-3.2 w/w %; 0.044 w/w %-3.1 w/w %; 0.045 w/w %-3 w/w %; 0.046 w/w %-2.9 w/w %; 0.047 w/w %-2.8 w/w %; 0.048 w/w %-2.7 w/w %; 0.049 w/w %-2.6 w/w %; 0.05 w/w %-2.5 w/w %; 0.051 w/w %-2.4 w/w %; 0.052 w/w %-2.3 w/w %; 0.053 w/w %-2.2 w/w %; 0.054 w/w %-2.1 w/w %; 0.055 w/w %-2 w/w %; 0.056 w/w %-1.9 w/w %; 0.057 w/w %-1.8 w/w %; 0.058 w/w %-1.7 w/w %; 0.059 w/w %-1.6 w/w %; 0.06 w/w %-1.5 w/w %; 0.061 w/w %-1.4 w/w %; 0.062 w/w %-1.3 w/w %; 0.063 w/w %-1.2 w/w %; 0.064 w/w %-1.1 w/w %; 0.065 w/w %-1 w/w %; 0.066 w/w %-0.99 w/w %; 0.067 w/w %-0.98 w/w %; 0.068 w/w %-0.97 w/w %; 0.069 w/w %-0.96 w/w %; 0.07 w/w %-0.95 w/w %; 0.071 w/w %-0.94 w/w %; 0.072 w/w %-0.93 w/w %; 0.073 w/w %-0.92 w/w %; 0.074 w/w %-0.91 w/w %; 0.075 w/w %-0.9 w/w %; 0.076 w/w %-0.89 w/w %; 0.077 w/w %-0.88 w/w %; 0.078 w/w %-0.87 w/w %; 0.079 w/w %-0.86 w/w %; 0.08 w/w %-0.85 w/w %; 0.081 w/w %-0.84 w/w %; 0.082 w/w %-0.83 w/w %; 0.083 w/w %-0.82 w/w %; 0.084 w/w %-0.81 w/w %; 0.085 w/w %-0.8 w/w %; 0.086 w/w %-0.79 w/w %; 0.087 w/w %-0.78 w/w %; 0.088 w/w %-0.77 w/w %; 0.089 w/w %-0.76 w/w %; 0.09 w/w %-0.75 w/w %; 0.091 w/w %-0.74 w/w %; 0.092 w/w %-0.73 w/w %; 0.093 w/w %-0.72 w/w %; 0.094 w/w %-0.71 w/w %; 0.095 w/w %-0.7 w/w %; 0.096 w/w %-0.69 w/w %; 0.097 w/w %-0.68 w/w %; 0.098 w/w %-0.67 w/w %; 0.099 w/w %-0.66 w/w %; 0.1 w/w %-0.65 w/w %; 0.101 w/w %-0.64 w/w %; 0.102 w/w %-0.63 w/w %; 0.103 w/w %-0.62 w/w %; 0.104 w/w %-0.61 w/w %; 0.105 w/w %-0.6 w/w %; 0.106 w/w %-0.59 w/w %; 0.107 w/w %-0.58 w/w %; 0.108 w/w %-0.57 w/w %; 0.109 w/w %-0.56 w/w %; 0.11 w/w %-0.55 w/w %; 0.111 w/w %-0.54 w/w %; 0.112 w/w %-0.53 w/w %; 0.113 w/w %-0.52 w/w %; 0.114 w/w %-0.51 w/w %; 0.115 w/w %-0.5 w/w %; 0.116 w/w %-0.49 w/w %; 0.117 w/w %-0.48 w/w %; 0.118 w/w %-0.47 w/w %; 0.119 w/w %-0.46 w/w %; 0.12 w/w %-0.45 w/w %; 0.121 w/w %-0.44 w/w %; 0.122 w/w %-0.43 w/w %; 0.123 w/w %-0.42 w/w %; 0.124 w/w %-0.41 w/w %; 0.125 w/w %-0.4 w/w %; 0.126 w/w %-0.39 w/w %; 0.127 w/w %-0.38 w/w %; 0.128 w/w %-0.37 w/w %; 0.129 w/w %-0.36 w/w %; 0.13 w/w %-0.35 w/w %; 0.131 w/w %-0.34 w/w %; 0.132 w/w %-0.33 w/w %; 0.133 w/w %-0.32 w/w %; 0.134 w/w %-0.31 w/w %; 0.135 w/w %-0.3 w/w %; 0.136 w/w %-0.29 w/w %; 0.137 w/w %-0.28 w/w %; 0.138 w/w %-0.27 w/w %; 0.139 w/w %-0.26 w/w %; 0.14 w/w %-0.25 w/w %; 0.141 w/w %-0.24 w/w %; 0.142 w/w %-0.23 w/w %; 0.143 w/w %-0.22 w/w %; 0.144 w/w %-0.21 w/w %; 0.145 w/w %-0.2 w/w %; 0.146 w/w %-0.19 w/w %; 0.147 w/w %-0.18 w/w %; 0.148 w/w %-0.17 w/w %; 0.149 w/w %-0.16 w/w %). In some aspects, the plant extract comprises, consists essentially of, or consists of a *Boswellia* extract, which includes *Boswellia serrata*, Burseraceae family, olibanum, or frankincense. Other aspects are directed to the plant extract combination comprising, consisting essentially of, or consists of: *Boswellia* extract (e.g., *Boswellia serrata*; Burseraceae family; olibanum; frankincense); a texturing and/or a bulking agent (e.g., cellulose (microcrystalline); a phospholipid (e.g., lecithin or phosphatidylcholine); and an anti-caking agent (e.g., silica, adsorbs water in hygroscopic applications). In additional aspects, the plant extract combination comprises, consists essentially of, or consists of: *Boswellia serrata* resin extract, cellulose (microcrystalline), lecithin, and silica.

Further embodiments provide the formulation or the topical formulation described here, where the therapeutically effective amount of the combination of free amino acids and the therapeutically effective amount of the plant extract or plant extract combination inhibit 5-lipoxygenase (an inflammation-inducing enzyme); decreases mobilization of calcium ions; decreases activation of MAP kinases. Without wishing to be bound by theory, the plant extract or plant extract combination comprising *Boswellia* extract comprises anti-inflammatory properties, which taper down the inflammation induced by, for example, 5-lipoxygenase. See, e.g., D. Poeckel and O. Werz (e.g., Curr Med Chem. 13(28): 3359-3369, 2006; Singh et al. Phytomedicine. 15(6-7):400-407, 2008.

In some of the embodiments, the formulation or the topical formulation comprises, consists essentially of, or consists of: as free amino acids, a therapeutically effective amount of a combination comprising (or consisting essentially of or consisting of) alanine, glutamine, glycine, and serine; a therapeutically effective amount of a plant extract, wherein the plant extract comprises (or consists essentially of or consists of): a *Boswellia* extract (e.g., *Boswellia serrata*; Burseraceae family; olibanum; frankincense); and optionally, a dermatologically acceptable carrier and/or additive, such as but not limited to: lecithin, microcrystalline cellulose, and silica.

Other embodiments provide the formulation or the topical formulation comprising, consisting essentially of, or consisting of: as free amino acids, a therapeutically effective amount of a combination comprising (or consisting essentially of or consisting of) an amino acid combination of at least one of alanine, glutamine, glycine, and serine; and a therapeutically effective amount of a plant extract or plant extract combination comprising (or consisting essentially of or consisting of) a *Boswellia* extract (e.g., *Boswellia serrata*; Burseraceae family; olibanum; frankincense) alone or in combination with at least one of: a texturing and/or a bulking agent (e.g., cellulose (microcrystalline); a phospholipid (e.g., lecithin); and an anti-caking agent (e.g., silica, adsorbs water in hygroscopic applications), where the amino acid combination and the plant extract combination are in a ratio of: 1:100 or greater (e.g., 2:100; 4:100; 6:100; 8:100; 10:100; 12:100; 14:100; 16:100; 18:100; 20:100; 22:100; 24:100; 26:100; 28:100; 30:100; 32:100; 34:100; 36:100; 38:100; 40:100; 42:100; 44:100; 46:100; 48:100; 50:100; 52:100; 54:100; 56:100; 58:100; 60:100; 62:100; 64:100; 66:100; 68:100; 70:100; 72:100; 74:100; 76:100; 78:100; 80:100; 82:100; 84:100; 86:100; 88:100; 90:100; 92:100; 94:100; 96:100; 98:100; 100:100); 100:1 or less (e.g., 99:100; 97:100; 95:100; 93:100; 91:100; 89:100; 87:100; 85:100; 83:100; 81:100; 79:100; 77:100; 75:100; 73:100; 71:100; 69:100; 67:100; 65:100; 63:100; 61:100; 59:100; 57:100; 55:100; 53:100; 51:100; 49:100; 47:100; 45:100; 43:100; 41:100; 39:100; 37:100; 35:100; 33:100; 31:100; 29:100; 27:100; 25:100; 23:100; 21:100; 19:100; 17:100; 15:100; 13:100; 11:100; 9:100; 7:100; 5:100; 3:100; 1:100); 1:100 to 100:1 (e.g., 1:99 to 99:1; 1:98 to 98:1; 1:97 to 97:1; 1:96 to 96:1; 1:95 to 95:1; 1:94 to 94:1; 1:93 to 93:1; 1:92 to 92:1; 1:91 to 91:1; 1:90 to 90:1; 1:89 to 89:1; 1:88 to 88:1; 1:87 to 87:1; 1:86 to 86:1; 1:85 to 85:1; 1:84 to 84:1; 1:83 to 83:1; 1:82 to 82:1; 1:81 to 81:1; 1:80 to 80:1; 1:79 to 79:1; 1:78 to 78:1; 1:77 to 77:1; 1:76 to 76:1; 1:75 to 75:1; 1:74 to 74:1; 1:73 to 73:1; 1:72 to 72:1; 1:71 to 71:1; 1:70 to 70:1; 1:69 to 69:1; 1:68 to 68:1; 1:67 to 67:1; 1:66 to 66:1; 1:65 to 65:1; 1:64 to 64:1; 1:63 to 63:1; 1:62 to 62:1; 1:61 to 61:1; 1:60 to 60:1; 1:59 to 59:1; 1:58 to 58:1; 1:57 to 57:1; 1:56 to 56:1; 1:55 to 55:1; 1:54 to 54:1; 1:53 to 53:1; 1:52 to 52:1; 1:51 to 51:1; 1:50 to 50:1; 1:49 to 49:1; 1:48 to 48:1; 1:47 to 47:1; 1:46 to 46:1; 1:45 to 45:1; 1:44 to 44:1; 1:43 to 43:1; 1:42 to 42:1; 1:41 to 41:1; 1:40 to 40:1; 1:39 to 39:1; 1:38 to 38:1; 1:37 to 37:1; 1:36 to 36:1; 1:35 to 35:1; 1:34 to 34:1; 1:33 to 33:1; 1:32 to 32:1; 1:31 to 31:1; 1:30 to 30:1; 1:29 to 29:1; 1:28 to 28:1; 1:27 to 27:1; 1:26 to 26:1; 1:25 to 25:1; 1:24 to 24:1; 1:23 to 23:1; 1:22 to 22:1; 1:21 to 21:1; 1:20 to 20:1; 1:19 to 19:1; 1:18 to 18:1; 1:17 to 17:1; 1:16 to 16:1; 1:15 to 15:1; 1:14 to 14:1; 1:13 to 13:1; 1:12 to 12:1; 1:11 to 11:1; 1:10 to 10:1; 1:9 to 9:1; 1:8 to 8:1; 1:7 to 7:1; 1:6 to 6:1; 1:5 to 5:1; 1:4 to 4:1; 1:3 to 3:1; 1:2 to 2:1).

Other embodiments provide any of the formulations or the topical formulations described here that optionally comprise, consist essentially of, or consist of a dermatologically acceptable carrier and/or additive. Non-limiting examples of carriers and additives useful in any of the formulations or the topical formulations described here can be selected from the group consisting of: water, sodium phytate, xanthan gum, kaolin, glycerin, polyglycerides (e.g., oleic polyglycerides, linoleic polyglycerides, linolenic polyglycerides), triglycerides (e.g., caprylic triglycerides, capric triglycerides), sucrose (e.g., sucrose stearate, sucrose distearate), alcohol (e.g., behenyl alcohol, benzoic alcohol, benzyl alcohol, cetearyl alcohol, oleyl alcohol), cetearyl glucoside, sodium stearoyl lactylate, Cera Alba (beeswax), *Butyrospermum parkii* (shea butter), *Prunus amigdalus sulcis* (sweet almond oil), *Simmondsia chinenesis* (jojoba oil) phenoxyethanol, lecithin, tocopherol, tocopherol acetate, ascorbyl palmitate, citric acid, potassium sorbate, lactic acid, UV protectant, hydrogenated olive oil decyl esters, decyl cocoate, astrocaryum, murumuru seed butter, zanthoxylum bungeanum fruit extract, squalene, pentylene glycol, dehydroacetic acid, tamarinds indica seed polysaccharide, sodium benzoate, curcumin, Zanthoxylum bungeanume fruit extract, *Passiflora edulis* seed oil, cetearyl ethylhexanoate, dimethicone, isopropyl myristate, acrylates/C10-C30 alkyl acrylate crosspolymer, allantoin, sodium phytate, PEG-90 stearate/glyceryl stearate; menthol, sodium hydroxide, sodium benzoate, dehydroacetic acid, benzoic alcohol, hexyldecanol, cetearyl ethylhexanoate, dimethicone, cetearyl ethylhexanoate, PEG-90 stearate/glyceryl stearate, ascorbyl palmitate, citric acid, Zanthoxylum bungeanum fruit extract, allantoin, disodium EDTA, phenoxyethanol, dehydroacetic acid, allantoin, XILOGEL®, *Vaccinium myrtillus* fruit extract, *Oryza sativa* (e.g. rice bran oil), isoamyl laurate, polymethyl methacrylate, fragrance, nutrients, antioxidants, water, or combinations thereof. In some embodiments, the formulation or the topical formulation of the disclosure, comprising (or consisting essentially of or consisting of): as free amino acids, a therapeutically effective amount of a combination comprising (or consisting essentially of or consisting of): alanine, glutamine, glycine, and serine; a therapeutically effective amount of a plant extract or a plant extract combination; a texturing and/or a bulking agent (e.g., cellulose (microcrystalline)); a phospholipid, where in some embodiments, phospholipids are used as an emulsifier (e.g., lecithin or phosphatidylcholine); and an anti-caking agent (e.g., silica, adsorbs water in hygroscopic applications); and optionally, a dermatologically acceptable carrier and/or additive. Non-limiting examples of at least one phospholipid useful in the formulation of the disclosure include any phospholipids comprising two fatty acids per phosphate backbone, where the phospholipid can include: phosphatidic acid (phosphatidate) (PA); phosphatidylethanolamine (cephalin) (PE); phosphatidylcholine (lecithin) (PC); phosphatidylserine (PS); phosphatidylinositol (PI); phosphatidylinositol phosphate (PIP); phosphatidylinositol bisphosphate (PIP2); and phosphatidylinositol trisphosphate (PIP3); ceramides comprising phosphate group; ceramide phosphorylcholine (Sphingomyelin) (SPH); ceramide phosphorylethanolamine (Sphingomelin) (Cer-PE); phospholipids comprising fatty acids selected from the group consisting of: saturated fatty acids (e.g., butyric acid, lauric acid, myristic acid, palmitic acid, stearic acid); unsaturated fatty acids (e.g., myristoleic acid (cis-9-tetradecenoic acid); sapienic acid (cis-6-hexadecenoic acid); palmitoleic acid (cis-9-hexadecenoic acid); oleic acid (cis-9-octadecenoic acid); petroselinic acid (cis-Octadec-6-enoic acid); cis-vaccenic acid (cis-11-octadecenoic acid); vaccenic acid (trans-11-octadecenoic acid); elaidic acid (trans-9-octadecenoic acid (trans-oleic acid)); linoleic acid; linolenic acid; paullinic acid (cis-13-eicosenoic acid); gadoleic acid (cis-9-icosenoic acid); gondoic acid (cis-11-eicosenoic acid); erucic acid (cis-15-docosenoic acid); brassidic acid (trans-15-docosenoic acid); nervonic acid (cis-15-tetracosenoic acid); arachidonic acid; and combinations thereof.

In additional embodiments, the formulation or the topical formulation described here can be prepared by mixing and/or stirring (concurrently, simultaneously, sequentially): (a) a therapeutically effective amount of a combination of free amino acids comprising, consisting essentially of at least one of alanine, glutamine, glycine, and serine; (b) a therapeutically effective amount of a plant extract or a plant extract combination comprising, consisting essentially of, or consisting of: a *Boswellia* extract (e.g., *Boswellia serrata*; Burseraceae family; olibanum; frankincense); and optionally, (c) a dermatologically acceptable carrier and/or additive. The mixture of (a), (b), and optionally (c) can be heated (either together or separately) to a temperature sufficient to completely mix, homogenize, or emulsify (a), (b), and optionally (c), where the temperature is 20° C. or greater (e.g., 22; 24; 26; 28; 30; 32; 34; 36; 38; 40; 42; 44; 46; 48; 50; 52; 54; 56; 58; 60; 62; 64; 66; 68; 70; 72; 74; 76; 78; 80; 82; 84; 86; 88; 90; 92; 94; 96; 98; 100; 102; 104; 106; 108; 110); 100° C. or less (e.g., 99; 97; 95; 93; 91; 89; 87; 85; 83; 81; 79; 77; 75; 73; 71; 69; 67; 65; 63; 61; 59; 57; 55; 53; 51; 49; 47; 45; 43; 41; 39; 37; 35; 33; 31; 29; 27; 25; 23; 21; 19; 17); or 20° C.-100° C. (e.g., 21° C.-99° C.; 22° C.-98° C.; 23° C.-97° C.; 24° C.-96° C.; 25° C.-95° C.; 26° C.-94° C.; 27° C.-93° C.; 28° C.-92° C.; 29° C.-91° C.; 30° C.-90° C.; 31° C. 89° C.; 32° C.-88° C.; 33° C.-87° C.; 34° C.-86° C.; 35° C.-85° C.; 36° C.-84° C.; 37° C.-83° C.; 38° C.-82° C.; 39° C.-81° C.; 40° C.-80° C.; 41° C.-79° C.; 42° C.-78° C.; 43° C.-77° C.; 44° C.-76° C.; 45° C.-75° C.; 46° C.-74° C.; 47° C.-73° C.; 48° C.-72° C.; 49° C.-71° C.; 50° C.-70° C.; 51° C.-69° C.; 52° C.-68° C.; 53° C.-67° C.; 54° C.-66° C.; 55° C.-65° C.; 56° C.-64° C.; 57° C.-63° C.; 58° C.-62° C.; 59° C.-61° C., for a time sufficient to completely mix, homogenize, or emulsify (e.g., seconds to minutes). In some aspects, the plant extract combination of the formulation or the topical formulation described here, further comprises (or consists essentially of or consists of): a texturing and/or a bulking agent (e.g., cellulose (microcrystalline)); a phospholipid (e.g., lecithin or phosphatidylcholine); and an anti-caking agent (e.g., silica, adsorbs water in hygroscopic applications). See, e.g., EXAMPLE 7.

Use of the Formulation for Skin Barrier Repair and Strengthening

Some embodiments of the disclosure provide for a formulation or a topical formulation described here comprising: a therapeutically effective amount of a combination of free amino acids comprising, consisting essentially of, or consisting of at least one of alanine, glutamine, glycine, and serine, or salts thereof; and therapeutically effective amount of a plant extract (e.g., *Boswellia serrata*; Burseraceae family; olibanum; frankincense; or combinations thereof) or a plant extract combination (e.g., *Boswellia* extract (e.g., *Boswellia serrata*; Burseraceae family; olibanum; frankincense); a texturing and/or a bulking agent (e.g., cellulose (microcrystalline); a phospholipid (e.g., lecithin or phosphatidylcholine); and an anti-caking agent (e.g., silica, adsorbs water in hygroscopic applications)). In additional aspects, the therapeutically effective amount of the combination of free amino acids and the therapeutically effective amount of the plant extract or the plant extract combination improves skin barrier repair. The improvement of skin barrier repair includes, and is not limited to, skin barrier correction, skin barrier strengthening, skin barrier preservation, skin barrier integrity, wound healing; growth, stimulation, proliferation, differentiation, and migration of epidermal cells, keratinocytes, endothelial cells, and fibroblasts; facilitation of dermal regeneration, and combinations thereof. Further aspects are directed to the modulation of epidermal growth factor (EGF) using a therapeutically effective amount of the amino acid combination or the formulation comprising (or consisting essentially of or consisting of) the amino acid combination described here, where the amino acid combination comprises, consists essentially of, or consists of at least one of alanine, glutamine, glycine, and serine, or salts thereof, in a ratio of, for example, 1:1:1:1.

In additional embodiments, a method of improving skin barrier repair of skin of a subject, comprises (or consists essentially of or consists of): administering a topical formulation, comprising (or consisting essentially of or consisting of) a therapeutically effective amount of a combination of free amino acids comprising (or consisting essentially of or consisting of) at least one of alanine, glutamine, glycine, and serine, or salts thereof; and a therapeutically effective amount of a plant extract combination comprising (consisting essentially of or consisting of) (e.g., *Boswellia serrata* resin extract, cellulose (microcrystalline), lecithin, silica): *Boswellia* extract (e.g., *Boswellia serrata*; Burseraceae family; olibanum; frankincense) alone or optionally in combination with at least one of: a texturing and/or a bulking agent (e.g., cellulose (microcrystalline)); a phospholipid (e.g., lecithin or phosphatidylcholine); and an anti-caking agent (e.g., silica, adsorbs water in hygroscopic applications); and optionally, a dermatologically acceptable carrier and/or additive, when when tested by a method detecting expression of a barrier marker gene such as but not limited to EGF and determining that the barrier marker gene is increased by a 1.5-40 average fold increase of amino acid treated as compared to amino acid untreated skin (see, e.g., FIGS. 8-14). Improving skin barrier repair is measured or indicated by a 1.5-40 average fold increase of skin barrier marker gene expression, such as EGF, when tested by a method detecting expression the barrier marker gene expression when comparing skin treated with any of the formulations described here to untreated skin. The method of improving skin barrier repair includes but is not limited to, correcting the skin barrier, strengthening the skin barrier, preserving the skin barrier, increasing skin barrier integrity, wound healing; growth, stimulation, proliferation, differentiation, and migration of epidermal cells, keratinocytes, endothelial cells, and fibroblasts; facilitating dermal regeneration, and any combinations thereof.

Use of the Formulation to Improve Barrier Integrity of Skin Cells

Formulations and Kits

The present disclosure provides for therapeutic or pharmaceutical formulations comprising a therapeutically effective amount of the subject formulation and, optionally, one or more pharmaceutically acceptable carriers. The present disclosure provides for therapeutic, pharmaceutical, cosmetic, or nutritional formulations comprising a therapeutically effective amount of the subject formulation and, optionally, one or more pharmaceutically acceptable carriers. Such pharmaceutical carriers can be liquids, such as water. The therapeutic formulation can also comprise excipients, adjuvants, flavoring agents, etc. that facilitate processing of the active compounds into preparations that can be used pharmaceutically. Proper formulation is dependent upon the route of administration chosen. In an embodiment, the therapeutic formulation and all ingredients contained therein are sterile. Examples of suitable pharmaceutical carriers are described in "Remington's Pharmaceutical Sciences" by E. W. Martin. Such formulations contain a therapeutically effective amount of the therapeutic formulation, together with a suitable amount of carrier so as to provide the form for proper administration to the patient. The formulation should suit the enteral mode of administration.

In one embodiment, the administration of the formulation can be systemic. Oral, intravenous, intra-arterial, subcutaneous, intra-peritoneal, intra-muscular, intra-ventricular, intranasal, transmucosal, subcutaneous, topical, rectal, and other modes of administration are all contemplated, as are all combinations thereof. In a particular embodiment, a formulation described herein is administered via administration to the skin (administered via, e.g., topical, transdermal, and/or subcutaneous administration, or any combination thereof). Formulations described herein may be incorporated into gauze, pads (adhesive or non-adhesive), bandages, and/or dressings for longer term application directly to skin. In a particular embodiment, a formulation described herein is administered to the skin in combination with oral administration of a formulation described herein. In a particular embodiment thereof, oral administration of a formulation described herein is implemented before, during, or after administration of a formulation to the skin. As described herein, administration to the skin may be achieved via topical, transdermal, and/or subcutaneous administration.

In one embodiment, for injection, the active ingredient can be formulated in aqueous solutions, in one example in physiologically compatible buffers. For transmucosal administration, penetrants appropriate to the barrier to be permeated are used in the formulation. For oral administration, the active ingredient can be combined with carriers suitable for inclusion into tablets, pills, dragees, capsules, liquids, gels, syrups, slurries, suspensions and the like. Formulations can also be prepared for use in inhalation therapy. For administration by inhalation, the formulation can be delivered in the form of an aerosol spray presentation from pressurized packs or a nebulizer, with the use of a suitable propellant. The formulation can also be administered via inhalation or other route as a powder.

Therapeutically effective doses of the presently described formulation can be determined by one of skill in the art, with a goal of achieving a desired strength of intercellular adhesion reflecting a healthy barrier integrity of the skin. An increase in the expression of marker genes indicative of skin cell proliferation, skin cell differentiation, and/or intercellular adhesion can be assessed using assays described herein. Immunohistochemistry, behavioral assessments, and/or electrophysiological techniques can also be utilized to assess barrier integrity of the skin.

In some embodiments, the methods according to the present disclosure include administering the therapeutic formulation by sustained-release systems. Suitable examples of sustained-release systems include suitable polymeric materials (such as, semi-permeable polymer matrices in the form of shaped articles, for example films, or microcapsules), suitable hydrophobic materials (for example as an emulsion in an acceptable oil) or ion exchange resins, and sparingly soluble derivatives (such as, for example, a sparingly soluble salt). Sustained-release formulations can be administered orally, parenterally, intracisternally, intraperitoneally, topically (as by powders, ointments, gels, drops or transdermal patch), or as an oral or nasal spray. Sustained-release matrices include polylactides, copolymers of L-glutamic acid and gamma-ethyl-L-glutamate, poly(2-hydroxyethyl methacrylate), ethylene vinyl acetate, or poly-D-(–)-3-hydroxybutyric acid.

In one embodiment, implantable drug infusion devices may be used to provide patients with a constant and long-term dosage or infusion of a therapeutic formulation. Such device can be categorized as either active or passive.

In one embodiment, polymers can be used for ion-controlled release. Various degradable and nondegradable polymeric matrices for use in controlled drug delivery may be used. For example, the block copolymer, polaxamer 407, hydroxyapatite, and liposomes.

The pharmaceutical formulation of the present invention may be used either alone or in combination with one or more drugs to be effective for treating diseases. The formulations can also be formulated in combination with at least one other agent, such as stabilizing or buffer compounds, which can be administered in any sterile, biocompatible pharmaceutical carrier, including, but not limited to, saline, buffered saline, dextrose, and water. In addition to the critical components of formulations discussed herein, cells or influencing factors, the formulations can contain suitable pharmaceutically acceptable carriers comprising excipients and auxiliaries that facilitate processing of the active compounds into preparations that can be used pharmaceutically. The formulation may be prepared as a single-dosage form using a pharmaceutically acceptable carrier or excipient or may be contained in a multiple-dosage container.

In one embodiment, the formulation may further contain other proliferation and/or differentiation inducing agents. Examples include fibroblast growth factor (FGF), epidermal growth factor (EGF), and retinoic acid.

The formulation may further contain other commonly used additives such as an anti-oxidant, a buffer, a bacteriostat, etc., and may be formulated into an injectable formulation such as aqueous solution, suspension, emulsion, etc. a pill, a capsule, a granule, a tablet, etc., by further adding a diluent, a dispersant, a surfactant, a binder, a lubricant, etc.

A food formulation of the present invention may be contained in a health functional food. The health functional food may be prepared according to a method commonly employed in the art, and commonly used raw materials and ingredients may be added when preparing the health functional food. When a formulation described herein is included in a health functional food, the formulation may be added alone or together with another health functional food or other food ingredient(s), according to commonly employed methods. The amount of the active ingredient may be determined appropriately depending on the purpose of use (e.g., prevention, health improvement, or therapeutic intervention). The food formulation may further comprise, for example, a prebiotic or probiotic substance.

The kind of food is not limited. Examples of the food to which the formulation can be added include meat, sausage, bread, chocolate, candy, snack, confectionery, pizza, ramen, other noodles, gum, dairy products including ice cream, soup, beverage, tea, drink, alcoholic beverage, vitamin complex, etc.

Also encompassed by the disclosure are kits (e.g., pharmaceutical, therapeutic, cosmetic, or nutritional packs). The kits provided may comprise a pharmaceutical formulation or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical formulation or compound described herein. In some embodiments, the pharmaceutical formulation or compound described herein provided in the first container and the second container are combined to form one unit dosage form.

Thus, in one aspect, provided are kits including a first container comprising a formulation described herein. In certain embodiments, the kits are useful for treating a disorder (e.g., a skin disorder) in a subject in need thereof. In certain embodiments, the kits are useful for preventing a disorder (e.g., a skin disorder) in a subject in need thereof.

In certain embodiments, a kit described herein further includes instructions for using the formulation included in the kit. A kit described herein may also include information as required by a regulatory agency such as the U.S. Food and Drug Administration (FDA). In certain embodiments, the information included in the kits is prescribing information. In certain embodiments, the kits and instructions provide for treating and/or preventing a disorder (e.g., a skin disorder) in a subject in need thereof. A kit described herein may include one or more additional pharmaceutical or other agents described herein as a separate formulation.

Methods of Administration

Formulations can be administered by any of a number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means.

For instance, by using "consisting essentially of," the therapeutic formulation does not contain any unspecified ingredients including, but not limited to, free amino acids, di-, oligo-, or polypeptides or proteins; and mono-, di-, oligo-, polysaccharides, and carbohydrates that have a direct beneficial or adverse therapeutic effect on improving barrier integrity of skin cells. Also, by using the term "consisting essentially of," the formulation may comprise substances that do not have therapeutic effects on improving barrier integrity of skin cells; such ingredients include carriers, excipients, adjuvants, flavoring agents, etc. that do not affect barrier integrity of skin cells.

In some embodiments, the formulation (e.g., topical formulation) described here can be topically applied to skin of a subject in need of skin barrier repair, wherein the formulation comprises a therapeutically effective amount of an amino acid combination comprising, consisting essentially of, or consisting of at least one of: alanine, glutamine, glycine, and serine, or salts thereof; a therapeutically effective amount of a plant extract (e.g., plant extract combination) comprising, consisting essentially of, or consisting of: a *Boswellia* extract (e.g., *Boswellia serrata*; Burseraceae family; olibanum; frankincense) alone or in combination of at least one of: a texturing and/or a bulking agent (e.g., cellulose (microcrystalline)); a phospholipid (e.g., lecithin or phosphatidylcholine); and an anti-caking agent (e.g., silica, adsorbs water in hygroscopic applications); and optionally, a dermatologically acceptable carrier and/or additive, wherein the therapeutically effective amount of the amino acid concentration comprises (or consists essentially of or consists of) 0.1 mM or greater (e.g., 0.3; 0.5; 0.7; 0.9; 1.1; 1.3; 1.5; 1.7; 1.9; 2.1; 2.3; 2.5; 2.7; 2.9; 3.1; 3.3; 3.5; 3.7; 3.9; 4.1; 4.3; 4.5; 4.7; 4.9; 5.1; 5.3; 5.5; 5.7; 5.9; 6.1; 6.3; 6.5; 6.7; 6.9; 7.1; 7.3; 7.5; 7.7; 7.9; 8.1; 8.3; 8.5; 8.7; 8.9; 9.1; 9.3; 9.5; 9.7; 9.9; 10.1; 10.3; 10.5); 10 mM or less (e.g., 9.8; 9.6; 9.4; 9.2; 9; 8.8; 8.6; 8.4; 8.2; 8; 7.8; 7.6; 7.4; 7.2; 7; 6.8; 6.6; 6.4; 6.2; 6; 5.8; 5.6; 5.4; 5.2; 5; 4.8; 4.6; 4.4; 4.2; 4; 3.8; 3.6; 3.4; 3.2; 3; 2.8; 2.6; 2.4; 2.2; 2; 1.8; 1.6; 1.4; 1.2; 1; 0.8; 0.6; 0.4; 0.2; 0.08; 0.06; 0.04; 0.02); or 0.1 mM-10 mM (e.g., 0.2 mM-9.9 mM; 0.3 mM-9.8 mM; 0.4 mM-9.7 mM; 0.5 mM-9.6 mM; 0.6 mM-9.5 mM; 0.7 mM-9.4 mM; 0.8 mM-9.3 mM; 0.9 mM-9.2 mM; 1 mM-9.1 mM); 1.1 mM-9 mM; 1.2 mM-8.9 mM; 1.3 mM-8.8 mM; 1.4 mM-8.7 mM; 1.5 mM-8.6 mM; 1.6 mM-8.5 mM; 1.7 mM-8.4 mM; 1.8 mM-8.3 mM; 1.9 mM-8.2 mM; 2 mM-8.1 mM; 2.1 mM-8 mM; 2.2 mM-7.9 mM; 2.3 mM-7.8 mM; 2.4 mM-7.7 mM; 2.5 mM-7.6 mM; 2.6 mM-7.5 mM; 2.7 mM-7.4 mM; 2.8 mM-7.3 mM; 2.9 mM-7.2 mM; 3 mM-7.1 mM; 3.1 mM-7 mM; 3.2 mM-6.9 mM; 3.3 mM-6.8 mM; 3.4 mM-6.7 mM; 3.5 mM-6.6 mM; 3.6 mM-6.5 mM; 3.7 mM-6.4 mM; 3.8 mM-6.3 mM; 3.9 mM-6.2 mM; 4 mM-6.1 mM; 4.1 mM-6 mM; 4.2 mM-5.9 mM; 4.3 mM-5.8 mM; 4.4 mM-5.7 mM; 4.5 mM-5.6 mM; 4.6 mM-5.5 mM; 4.7 mM-5.4 mM; 4.8 mM-5.3 mM; 4.9 mM-5.2 mM; 5 mM-5.1 mM), wherein the therapeutically effective amount of the plant extract (or plant extract concentration) comprises (or consists essentially of or consists of): 0.01% or greater (e.g., 0.03; 0.05; 0.07; 0.09; 0.11; 0.13; 0.15; 0.17; 0.19; 0.21; 0.23; 0.25; 0.27; 0.29; 0.31; 0.33; 0.35; 0.37; 0.39; 0.41; 0.43; 0.45; 0.47; 0.49; 0.51; 0.53; 0.55; 0.57; 0.59; 0.61; 0.63; 0.65; 0.67; 0.69; 0.71; 0.73; 0.75; 0.77; 0.79; 0.81; 0.83; 0.85; 0.87; 0.89; 0.91; 0.93; 0.95; 0.97; 0.99; 1.1; 1.3; 1.5; 1.7; 1.9; 2.1; 2.3; 2.5; 2.7; 2.9; 3.1; 3.3; 3.5; 3.7; 3.9; 4.1; 4.3; 4.5; 4.7; 4.9; 5.1; 5.3; 5.5; 5.7; 5.9; 6.1; 6.3; 6.5; 6.7; 6.9; 7.1; 7.3; 7.5; 7.7; 7.9; 8.1; 8.3; 8.5; 8.7; 8.9; 9.1; 9.3; 9.5; 9.7; 9.9; 10.1; 10.3; 10.5; 10.7; 10.9; 11.1); 10% or less (e.g., 9.8; 9.6; 9.4; 9.2; 9; 8.8; 8.6; 8.4; 8.2; 8; 7.8; 7.6; 7.4; 7.2; 7; 6.8; 6.6; 6.4; 6.2; 6; 5.8;

5.6; 5.4; 5.2; 5; 4.8; 4.6; 4.4; 4.2; 4; 3.8; 3.6; 3.4; 3.2; 3; 2.8; 2.6; 2.4; 2.2; 2; 1.8; 1.6; 1.4; 1.2; 1; 0.8; 0.6; 0.4; 0.2; 0.08; 0.06; 0.04; 0.02; 0.008; 0.006; 0.004; 0.002); or 0.01%-10% (e.g., 0.02%-9.9%; 0.03%-9.8%; 0.04%-9.7%; 0.05%-9.6%; 0.06%-9.5%; 0.07%-9.4%; 0.08%-9.3%; 0.09%-9.2%; 0.1%-9.1%; 0.2%-9%; 0.3%-8.9%; 0.4%-8.8%; 0.5%-8.7%; 0.6%-8.6%; 0.7%-8.5%; 0.8%-8.4%; 0.9%-8.3%; 1%-8.2%; 1.1%-8.1%; 1.2%-8%; 1.3%-7.9%; 1.4%-7.8%; 1.5%-7.7%; 1.6%-7.6%; 1.7%-7.5%; 1.8%-7.4%; 1.9%-7.3%; 2%-7.2%; 2.1%-7.1%; 2.2%-7%; 2.3%-6.9%; 2.4%-6.8%; 2.5%-6.7%; 2.6%-6.6%; 2.7%-6.5%; 2.8%-6.4%; 2.9%-6.3%; 3%-6.2%; 3.1%-6.1%; 3.2%-6%; 3.3%-5.9%; 3.4%-5.8%; 3.5%-5.7%; 3.6%-5.6%; 3.7%-5.5%; 3.8%-5.4%; 3.9%-5.3%; 4%-5.2%; 4.1%-5.1%; 4.2%-5%; 4.3%-4.9%; 4.4%-4.8%; 4.5%-4.7%).

EXAMPLES

The following examples illustrate specific aspects of the instant description. The examples and embodiments described herein are for illustrative purposes only and various modifications or changes in light thereof are suggested to persons skilled in the art and are included within the spirit and purview of this application. In addition, any elements or limitations of any embodiment thereof disclosed herein can be combined with any and/or all other elements or limitations (individually or in any combination) or any other embodiment thereof disclosed herein, and all such combinations are contemplated with the scope of the embodiments described here without limitation thereto. The examples should not be construed as limiting, as the example merely provides specific understanding and practice of the embodiments and its various aspects.

Example 1: Testing of Amino Acids

To test the effect of amino acid treatment on epithelial skin barrier, a cellular model of differentiated normal human epidermal keratinocytes (NHEK) was utilized. Commercially available NHEK (ATCC), derived from three diverse healthy donors, were used. Based on a multivariate analysis, three amino acids for the treatment: Ser, Gln and Gly were selected.

Microarray gene expression and RNA sequencing (RNA-seq) analyses were utilized to assess the transcriptome of a panel of differentiated NHEK, focusing on a particular set of marker genes whose upregulation or downregulation (depending on the marker gene) reflects a trend toward improved barrier function in the skin. Upregulation of marker genes that promote, for example, keratinocyte differentiation and/or proliferation and downregulation of marker genes that promote, for example, apoptosis/cell death and/or inflammation reflect a trend toward improved barrier function in the skin. In contrast, downregulation of marker genes that promote, for example, keratinocyte differentiation and/or proliferation and upregulation of marker genes that promote, for example, apoptosis/cell death and/or inflammation reflect a trend toward impaired barrier function in the skin.

Using gene arrays, comparative analyses of two datasets were performed in three diverse donors focusing on consistently differentially [filter criterion of fold change 1.5 (positive or negative) and p-value <0.05] expressed genes following treatment with various amino acids and combinations thereof. qPCR was used to assess the mRNA expression results. The qPCR results confirmed the array results pertaining to differential expression, thereby validating the panel of genes.

The marker genes: EGF, FGF, CPT2, TGFB1, SMAD1, MK167, PPARGC1B, CASP8 and TNFRSF10D, and PPARA and PPARD were also included in the panel of marker genes examined, in part because PPARGC1B, a transcription factor, encodes a coactivator of PPARα, PPARδ, and PPARγ. The significant upregulation of CPT2 (which is a primary target for PPARα) reinforced inclusion of PPARA and PPARD in the panel.

Each of the amino acids was also titrated to arrive at suitable concentrations for use in amino acid combinations. Accordingly, suitable (e.g., non-toxic, non-morphology changing, therapeutically effective) concentrations for each single amino acid were determined during the course of developing suitable amino acid combinations.

Comparative analysis of qPCR data from two donors, which included a scoring system (as described above), identified two sets of consistently most effective (Gly, Gln, Ser, Ala) and least effective (Asp, Thr, Cys, Pro, Tyr) amino acid combinations. See, e.g., FIG. 2.

Two combinations of the most effective amino acids were tested as an initial set of components for skin formulations in five different donors [combo #1 (Gln, Gly, Ala, Ser) and combo #2 (Gln, Gly, Ala, Ser, Ile, Val)] to evaluate the effect thereof on mRNA expression (transcripts) of ten genes: EGF, FGF2, PDGF, CPT2, TGM4, PPARD, TGFB1, FLG, MKI67, and TNFRSF10D. For the comparison, a set of the least effective amino acids (combo #3) was used in qPCR analysis. See, e.g., FIG. 1.

The conclusion from the experiments was that the combination of the most effective amino acids (combos #1 and 2) significantly increased gene expression of six out of ten tested genes (FIG. 1), while combo #3 had no effect on transcripts of the majority of the genes, or even downregulated them as in the case of EGF. In contrast, mRNA expression of TNFRSF10D, which encodes a member of TNF receptor superfamily, was significantly downregulated by combo #1, suggesting an anti-inflammatory/anti-apoptotic functionality for combo #1. The most significant effect of combo #1 and #2 was detected on upregulation of the transcript of EGF. Collectively, these results demonstrate that particular combinations of specific amino acid combinations, but not all or random amino acid combinations, upregulate keratinocyte genes important for normal barrier function.

These results further show that careful testing of amino acid combinations, considering multivariate, interdependent data points, is required to obtain the best beneficial effect. It is noteworthy that each of combo #1 and combo #2 conferred statistically significant increases in the expression of many of the marker genes identified relative to controls in the context of healthy skin such as that provided by keratinocytes derived from three diverse healthy donors. Results determined in the context of injured/compromised skin may yield even more significant results demonstrating efficacy of combo #1 and combo #2 and other amino acid combinations described herein. Results presented herein underscore the demonstrated potency of combo #1 and combo #2 and are reasonably predictive of their potential for the enhancement of the skin barrier, especially in the context of injured/compromised skin.

Results presented herein also demonstrate upregulation of proteins so as to result in contributing positively to barrier integrity of the skin. Involucrin, for example, was upregulated to a statistically significant degree at 24 h post-treatment with either of combo #1 or combo #2 relative to control. See, e.g., FIG. 5. Filaggrin was also upregulated to a statistically significant degree at 24 h post-treatment with either of combo #1 or combo #2 relative to control. See, e.g., FIG. 6.

Specific combinations of amino acids in suitable ratios had a synergistic effect and an orchestrating ability to improve and/or restore the skin barrier integrity. Particular amino acid combinations trigger some cellular pathways that in totality provide a desired synergistic effect.

Example 2: Experimental Methods

Amino acids are mixed in previously established concentrations in water and added to amino acid deprived culture medium.

Gene Expression:

mRNA is extracted, converted to cDNA and analyzed by qPCR method using custom TaqMan array 384-well plates (Thermo Fisher Scientific) containing 34 of the above-mentioned genes. Four control housekeeping genes are included to normalize the mRNA expression: GAPDH, POLR2A, YWHAZ and PGK1. The array plate will contain 38 genes in total and 10 samples can be analyzed in one run of qPCR.

Protein Analysis:

Western Blot. Keratinocytes or epidermal skin equivalents are homogenized in lysis buffer, protein is extracted, and Western blots performed per standard protocols. The following commercial antibodies are used: filaggrin (#sc-66192, Santa Cruz Bio), loricrin (#ab183646), involucrin (#ab68), TGM2 (#ab2386) (all from Abcam), β-actin (#SAB3500350, Sigma).

Since Western Blot analysis is labor intensive and not a high throughput assay, for some proteins ELISA is used instead, utilizing already validated assays as previously published for protein ELISAs. ANGPTL4 and involucrin immunoassays are carried out using Milliplex Map Human Liver Protein Magnetic Bead Panel hANGPTL4-MAG and Milliplex Map Human Skin Magnetic Bead INVOL-MAG (EMD Millipore, Billerica, MA) on a Luminex xMAP platform.

Statistics:

The differences between control and treatment groups are evaluated by 1-way ANOVA. Statistically, significant variation is defined as >20% variation from the control for protein assay and positive or negative fold change threshold of 1.5 for gene expression with a p-value p<0.05.

Example 3: Experimental Design and Methods Defining Additional Efficacious Combinations of Amino Acids Promoting Skin Barrier Function In addition to the amino acid combinations described above, several other combinations are tested that include, e.g., Trp and/or Arg to determine if inclusion of these amino acids confers additional dermatological benefits. These two amino acids exhibited positive effects in preliminary screens, making them attractive candidates for inclusion in the amino acid formulations described herein. At the outset, the following combinations of amino acids are tested: Ala, Gln, Gly, Ser (combo #1); Ala, Gln, Gly, Ser, Val, Ile (combo #2); Ala, Gln, Gly, Ser, Val; Ala, Gln, Gly, Ser, Ile; Ala, Gln, Gly, Ser, Ile, Val, Trp; Ala, Gln, Gly, Ser, Ile, Val, Arg; and Ala, Gln, Gly, Ser, Ile, Val, Trp, Arg.

The experiments are conducted using differentiated normal primary keratinocytes of five different donors as above and commercially available epidermal skin equivalents (3D model) (EPI-200, MatTech, Ashland, MA). Such 3D cultures approximate human epidermis and are commonly used in skin research. In order to ensure the appropriate experimental conditions, the experiments are conducted in amino acid deprived medium during the time of the treatment with specific amino acid combinations. Since amino acids constitute critical components of the formulations described herein, the presence of amino acids normally present in culture medium has the potential to obfuscate the results, hence leading to a choice of amino acid deprived medium as the control. The cells or equivalents are treated with a combination of amino acids for 4 or 24 h. Differentiation of keratinocytes is induced by culturing them in the presence of 1.2 mM $CaCl_2$ for 48 h prior the treatment in FBS-free medium (amino acid deprived medium).

First, an array of classical skin barrier related genes that includes a previously tested panel is examined. The following genes encoding key components of the barrier or barrier formation process are included in arrays: growth factors EGF, TGFB1, FGF2, PDGF, terminal differentiation markers such as filaggrin (FLG), loricrin (LOR), TGM4, CORIN, KRT6, KRT16, SFN, SPRR2H and the late cornified envelope genes (LCE1, LCE3, S100A8/A9); lipid metabolism regulators such as PPARA, PPARD, CPT2, PNPLA1, FASN, UGCG, HMGCR, PLA2G5, ELOVL; adhesive structures (CLDN4, CLND7, DSC1, DSC2, OCLN, TJP1 and TJP2); water channel AQP3 and skin barrier integrity genes: SPINK5, KLK5, KLK7. High throughput analysis of mRNA expression of the above genes is performed using custom TaqMan array plates (Thermo Fisher Scientific). The % of genes that are co-expressed after the treatment with different amino acid combinations will be determined. Expression levels of crosslinking proteins such as involucrin, loricrin, TGM2 and ANGPTL are assessed by Western Blot analysis or ELISA using standard protocols.

Methods are performed as described in EXAMPLE 2.

Example 4: Other Model Systems in which to Assess and Identify Efficacious Amino Acid Combinations Alternative models of keratinocytes that have immature or impacted barrier are tested to assess the effect of amino acid formulations described herein. Such model systems include, for example: undifferentiated keratinocytes (cultured in low calcium concentrations (0.03 mM)). These cells have an immature epithelial barrier; differentiated keratinocytes switched to low Ca2+-containing medium (0.03 mM) for 24 h prior the treatment. It has been shown that when epithelial cells are depleted of Ca2+, the TJs open and thereby disrupt the permeability barrier. This process is reversible with Ca2+ replenishment; and differentiated keratinocytes treated with Th2 cytokines for 24 hours: IL-4 (50 ng/mL) and IL-13 (50 ng/mL) that downregulate the expression of filaggrin.

Example 5: Experimental Design and Methods Evaluating Efficacy of Topical Administration of Amino Acid Combinations on Skin Barrier Repair in In Vitro and Ex Vivo Models of Normal and Compromised Skin The next step in evaluating the efficacy of amino acid formulations described herein is tested via topical administration, which is achieved by direct application on the stratum corneum surface. Normal and immature epidermal skin equivalents (EPI-200 and EPI-20, MatTek Corporation, Ashland, MA) and normal and delipidated (tape-stripped) skin explants are used as models for normal and compromised skin. Full-thickness human skin obtained from normal human adults undergoing abdominoplasty surgeries is available commercially for research and obtained from Zen Bio (Durham, NC). In addition to assessing expression of key barrier markers described in, for example, EXAMPLE 1, TJ proteins will also be examined. TJ proteins are involved in normal barrier function that prevents transepidermal water loss (TEWL) in healthy skin. Accordingly, expression of TJ proteins are assessed by Western Blot analysis and immunohistochemistry. Transepithelial electrical resistance (TEER) measurements will also included as an indicator of barrier integrity and TJ dynamics. Expression of filaggrin, involucrin, and loricrin is also performed as in EXAMPLE 1.

Methods:

Ex Vivo Model:

Ex-vivo studies are performed using human skin explants. Subcutaneous fat is removed from abdominal skin (Zen Bio) and skin biopsies of 0.93 $cm^2$ are prepared under sterile conditions and placed in keratinocyte growth medium under a 5% $CO_2$ humidified atmosphere. To artificially induce scaly delipidated skin, abdominal skin is first tape-stripped per standard protocol and then biopsies are prepared. After 24 h of adaptation, amino acid combinations are applied topically every 24 hours for 7 days in total. Skin explants are analyzed for gene and protein expression levels at 24, 48, 72 hours and at the end of the experiment.

Measurement of Transepithelial Electrical Resistance (TEER) in 3D Model.

For TEER, immature epidermal skin equivalents (EPI-20, MatTek Corporation, Ashland, MA) are transferred to medium containing 100 ng/ml IL-4, 100 ng/ml IL-13, 50 ng/ml IL-31 and 30 ng/ml TNFα (R&D Systems, Minneapolis, MN) as described previously. Amino acid combinations are applied topically every 24 hours after 4 hours of pretreatment with cytokines. TEER is measured at 0, 24, and 48 hours by using Millicell ERS-2 Epithelial Volt-Ohm Meter (Milipore). The percentage change in TEER between time 0 (100%) and time 24 hours is expressed as follows: (TEER24 hours/TEER0 hours)×100. At the end of the experiment skin equivalents are used for mRNA and protein expression analysis.

qPCR Analysis.

Expression of the array of 38 genes is performed as described in EXAMPLES 1 and 2 using custom TaqMan array plates.

Protein Analysis:

Western Blot:

Expression of filaggrin, involucrin, loricrin, ANGPTL4 and TGM-2 is performed as described in EXAMPLES 1 and 2.

Immunohistochemical Staining.

Skin explants topically treated with amino acid combinations are incubated for 7 days with treatment renewal every 24 hours and collected for staining at the end of the experiment. The tissues are fixed in a 10% buffered neutral formalin solution. Fixed tissues are embedded and 5-μm-thick sections prepared. Immunohistochemistry analysis is performed using standard protocols. Sections are deparaffinized in xylene, hydrated in ethanol, and washed in water. Nonspecific binding is blocked with the mouse IG blocking reagent. The following primary antibodies are used: claudin-1 (JAY.8), occludin (OC-3F10), ZO-1 (ZO1-1A12), all from Zymed, or isotype control as described. Tissue sections will then be incubated with appropriate biotinylated secondary antibody and antibody binding is visualized using a DAB Peroxidase Substrate Kit (Vector Laboratories). The staining is assessed through microscopic observation.

Example 6: Methods and Materials

Cell Culture and Treatments

Human primary keratinocytes were treated with a panel of amino acid(s), either single amino acids and/or amino acid combinations, in order to prepare experimental samples for RNA analysis.

Primary normal human adult keratinocytes (ATCC, Cat #PCS-200-011) were cultured in Dermal Cell Basal Medium (ATCC, Cat #PCS-200-030) with growth supplement (Keratinocyte Growth Kit, ATCC Cat #PCS-200-040). For the cell growth, the medium was changed three times per week. For the experiment, cells were seeded on 6-well plates with a density of 20,000 cells/well. When cells reached 100% confluency, $CaCl_2$) was added to the final concentration of 1.8 mM for 24 h, to induce differentiation. All treatments were performed in amino acid-deprived medium (Choline Chloride 0.0285 mM, D-Calcium Pantothenate 0.00838 mM, Folic Acid 0.009 mM, Niacinamide 0.03 mM, Pyridoxine hydrochloride 0.02 mM, Riboflavin 0.001 mM, Thiamine Hydrochloride 0.01 mM, Myo-inositol 0.04 mM, Calcium Chloride 1.8 mM, Ferric Nitrate 2.47E-4 mM, Magnesium Sulfate 0.8 mM, Potassium Chloride 5.3 mM, Sodium Bicarbonate 44 mM, Sodium Chloride 110.3 mM, Sodium Phosphate Monobasic 0.9 mM, D-Glucose 25 mM, Sodium Pyruvate 1 mM) in the presence of 1.8 mM $CaCl_2$) for 4 h. The 4GAA combination contained Glycine, Glutamine, Serine, and Alanine and was used in a total concentration of 4 mM (1:1:1:1). The 3BAA combination contained Cysteine (1 mm), Histidine (0.5 mM), Tyrosine (1 mM). The plant extract combination containing *Boswellia serrata* resin extract, lecithin, microcrystalline cellulose, and silica was dissolved in the amino-acid-deprived medium, filtered, and used in concentrations 0.1 w/w %-1 w/w % of the formulation.

Real-Time RT-PCR Analysis:

Cellular RNA was isolated using a NucleoSpin RNA Plus kit (Macherey Nagel). cDNA synthesis was performed using High-Capacity cDNA Reverse Transcription Kit (Thermo Fisher Scientific) with 1 μg of total RNA. RT product was amplified using EGF, MYC, GAPDH, YWHAZ TaqMan Gene Expression Assays (Thermo Fisher Scientific). Detection was performed using the StepOne Real-Time PCR System (Applied Biosystems). Differences in the levels of gene expression were determined by relative quantification using the delta Ct method.

Equipment, Materials, Reagents, and Supplies

Confluent differentiated primary human keratinocytes were used in 6-well plates. The following were used in experiments described here:

Sterile RNase-free microcentrifuge (1.7 mL) and conical (50 mL and 15 mL) tubes.

Pipette, Multi-Channel pipette, Pipette Controller (Aid), Serological Pipettes and Pipette Tips, Aspirating Pipettes.

Sterile Isopropyl Alcohol (SIPA, 70%).

Dulbecco's media.

Amino Acids: Serine, Glycine, Glutamine, Histidine, Valine, Tyrosine, Threonine, Aspartic Acid, or others based on experimental needs.

Vacuum line/Vacuum pump, and pump waste collection receptacles.

Syringe (30 mL), Syringe Filter (25 mm PES; 0.22 Micron), Syringe Needles (18G).

Weighing Supplies: Paper, Spatula, etc.

Lab equipment: Biosafety cabinet (BSC), Water Bath (37° C.), 5% CO2 Incubator (37° C.) Refrigerator (4° C.), Analytical Balance, Heat/Stir Plate.

TABLE 1

Reagents/Supplies Storage Conditions

| Item | Room Temp (~20° C.-25° C.) | Refrigerator (4° C.) | $CO_2$ incubator (37° C.) |
|---|---|---|---|
| AA9(s) | X | | |
| PBS | | X | |
| Primary Human Keratinocytes | | | X |
| DMEM | | X | |
| AA solutions | | X | |

Amino Acid Treatment Preparation

Treatments were prepared no more than one week prior to beginning the experiment. A water bath was pre-heated to 37° C. The DMEM was retrieved and aseptically transferred to the BSC. The needed volume of DMEM (2 ml/well) was pipetted into conical tubes (50 mL), which were pre-warmed in the heated water bath for 30 min. The other required materials: conical tubes (50 mL), syringes (30 mL), needles (18G), and micron syringe filters (25 mm; 0.22 micron) were aseptically transferred to the BSC. The amino acids required for treatment were prepared by labeling conical tubes (50 mL), either for single amino acids (4 mM, 20 mM), 4 amino acid combination (4 mM, 20 mM), or ENTERADE™ (see, TABLE 2).

The appropriate amount of each amino acid (See, TABLE 2) was weighed out before they were transferred to their respective conical tubes. The amino acids for the 4AA formula and "ENTERADE®" should be weighed out individually and then transferred into the designated tube and labeled together. All of the conical tubes (50 mL) containing the dry amino acids and pre-warmed DMEM were aseptically transferred to the BSC. DMEM was transferred into the tubes according to TABLE 2 using serological pipettes.

All of the tubes were vortexed until the mixture was free of debris and homogenous and then the homogenous mixtures were aseptically returned to the BSC.

Should a mixture not be fully in solution with just vortexing, a small stir bar was placed in the conical tube (50 mL), then the conical tube was placed in a beaker half-filled with water and used a heat/stir plate (50° C./800 rpm) for ~10 min until the solution was homogenous.

In a separate rack, a new set of conical tubes (50 mL) was labeled for each amino acid or the amino acid combination with the AA name, concentration, and date.

A needle (18G) was attached to a syringe (10 mL) and the entire contents of one of the AA "Medium" tubes were drawn up. The needle was removed and a syringe filter (13 mm, 0.22 Micron) was attached to the syringe (10 mL). The syringe filter (25 mm, 0.22 Micron) was placed over the corresponding amino acid (AA) "Treatment" labeled tube, the mixture was pushed in the syringe through the filter into the tube, and capped immediately. This was repeated as needed, changing filters for every 100 mL filtered or in-between each amino acid sample.

The syringe filtration step was repeated for each AA or AA combination and the syringe, needle, and filter were replaced in between each AA or AA combination to avoid cross contamination.

TABLE 2

Amino Acids and Concentrations

| Amino Acid | Weight (mg) | Volume (mL) | 1X Stock Concentration (mM) | Final Concentration (mM) |
|---|---|---|---|---|
| Serine | 16.816 | 40 | 4 | 4 |
| Glycine | 12.011 | 40 | 4 | 4 |
| Histidine | 23.383 | 40 | 4 | 4 |
| Glutamine | 24.862 | 40 | 4 | 4 |
| Serine | 84.80 | 40 | 20 | 20 |
| Glycine | 60.056 | 40 | 20 | 20 |
| Histidine | 116.916 | 40 | 20 | 20 |
| Glutamine | 124.128 | 40 | 20 | 20 |
| 4AA Serine | 16.816 | 40 | 4 | 4 |
| 4AA Glycine | 12.011 | 40 | 4 | 4 |
| 4AA Histidine | 23.383 | 40 | 4 | 4 |
| 4AA Glutamine | 24.862 | 40 | 4 | 4 |
| 4 AA Serine | 84.08 | 40 | 20 | 20 |
| 4 AA Glycine | 60.056 | 40 | 20 | 20 |
| 4AA Histidine | 116.916 | 40 | 20 | 20 |
| 4AA Glutamine | 124.128 | 40 | 20 | 20 |
| ENTERADE® Serine | 31.94 | 30 | 10 | 8 |
| ENTERADE® Valine | 28.5888 | 30 | 10 | 10 |
| ENTERADE® Tyrosine | 6.52284 | 30 | 1.2 | 1.2 |
| ENTERADE® Threonine | 35.154 | 30 | 8 | 8 |
| ENTERADE® Aspartic Acid | 31.53 | 30 | 8 | 8 |
| Control | NA | 15 | NA | NA |

Amino Acid Treatment

PBS and AA treatments were pre-warmed in the water bath (37° C.) for 30 minutes. The 6-well plates containing "Differentiated Keratinocytes" were aseptically transferred from the 500 $CO_2$ Incubator (37° C.) into the BSC. The 6-well plate lids were labeled with Date, Initials, Passage #, Cell Family, and the Target treatment. The well imprints on the plate's lid were labeled with T #(Treatment Wells) or C#(PBS only Wells).

The medium from each well was aspirated and washed with 2.0 mL PBS.

The PBS from each well was aspirated and 2.0 mL of the AA treatments was added into the wells ensuring the treatment added corresponds to the plate's label. (Serine treatments only went into wells of the serine labeled plate).

The remaining control well was filled in each plate with 2 mL of DMEM and the 6-Well plates in a secondary container were transferred to the 5% $CO_2$ incubator (37° C.) and incubated based on the experiment.

Once the incubation time was completed, the "Treated" cells were removed and transferred to the BSC for RNA/Protein extraction.

Example 7: Preparation of Formulation

An exemplary method of preparing the formulation or topical formulation disclosed here included the steps as follows:

Dispersed the xanthan gum in glycerin.
Mixed until homogenous and then added water.
Mixed until homogenous.
Heated Phase A ingredients of TABLE 3 to a temperature of 80° C.
Separately heated Phase B ingredients of TABLE 3 to a temperature of 80° C.
With both phases at 80° C., Phase B was added to Phase A with vigorous mixing, then removed from heat, forming a batch of Phase A and Phase B.

When the batch temperature was below 40° C., Phase C ingredients of TABLE 3 were added to the batch.

Then q.s. batch to 100% with deionized water. Various amino acids tested here were combined with the formulation prepared here, including alanine, glutamine, glycine, and serine.

TABLE 3

| PHASE | TRADENAME | INCI NAME | COMPANY | % IN FORMULA |
|---|---|---|---|---|
| A | Keltrol Cg-Sft | Xanthan Gum | Cp Kelco | 0.600% |
| A | Glycerin | Glycerin | Independent Chemical | 1.000% |
| A-A | Deionized Water | Water | | 75.000% |
| B | Ips Deca-Dp | Polyglyceryl-10 Dipalmitate | Ips Labs | 1.750% |
| | Ips Hexa-Ds | Polyglyceryl-6 Distearate | Ips Labs | 0.750% |
| B | Stearyl Alcohol | Stearyl Alcohol | | 5.000% |
| B | Sunflower Oil | Helianthus Annuus Seed Oil | | 12.000% |
| C | Lexgard Natural Mhg Mb | Methylheptyl-glycerin | Inolex | 2.000% |
| C | Zeastat | Capryl-hydroxamic Acid (And) Propanediol | Inolex | 1.000% |

Figure 7A:
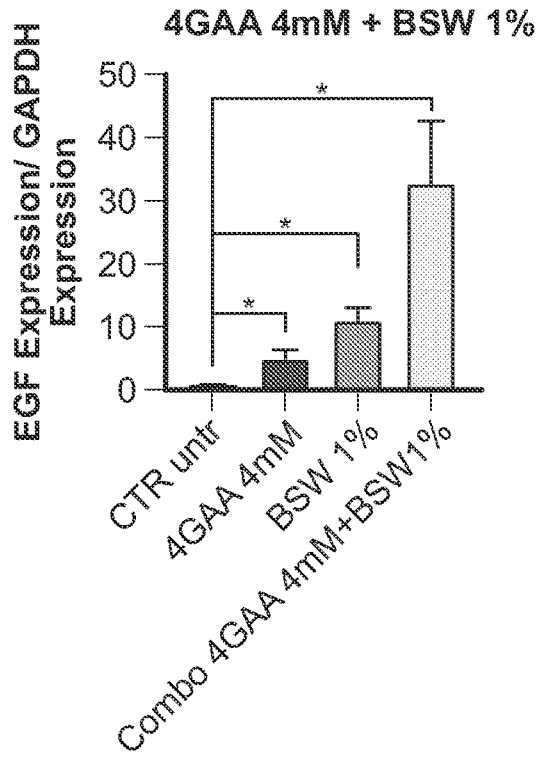
FIGS. 7A-7D present graphs of EGF expression comparing the 4 amino acid combination (Ala, Gln, Gly, Ser; 4GAA) and *Boswellia* plant extract combination (BSW=BSXL) alone or in combination.
Figure 7B:
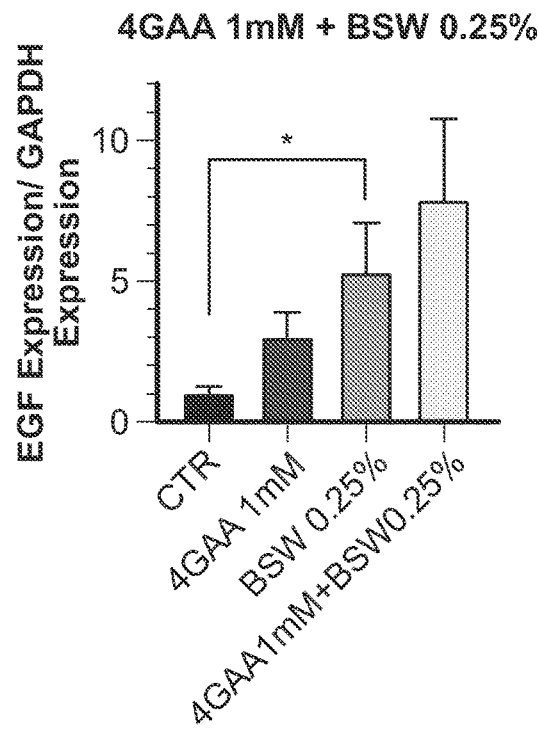
Figure 7C:
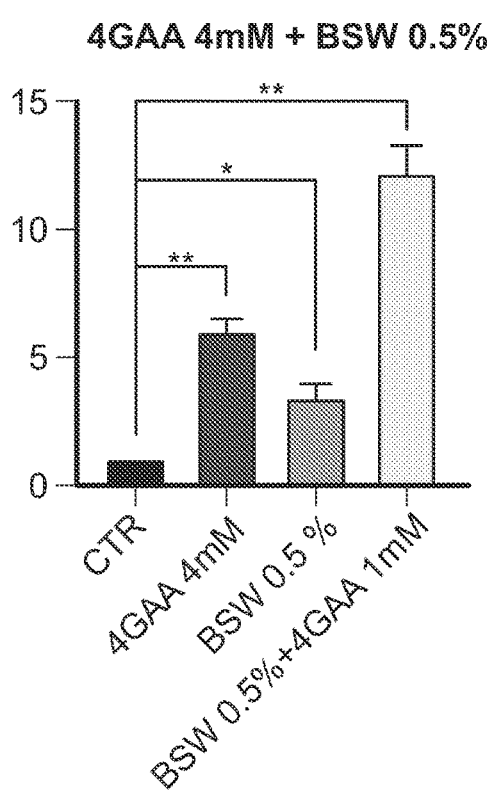
Figure 7D:
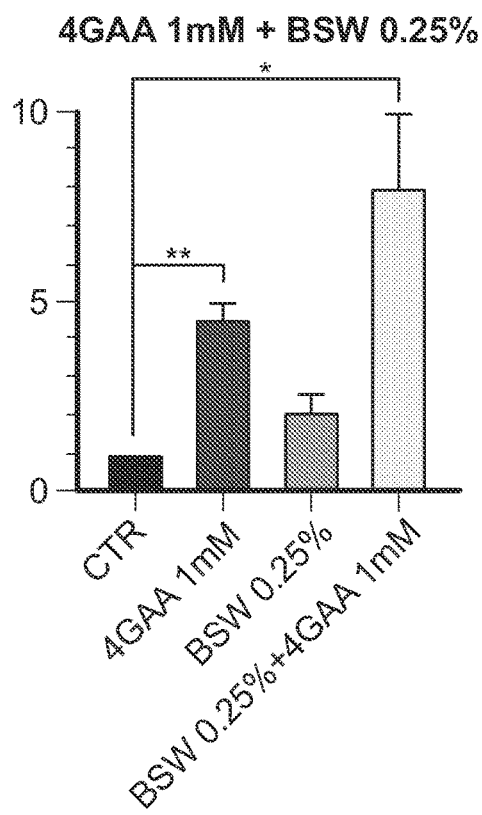
Figures 8A, 8B:
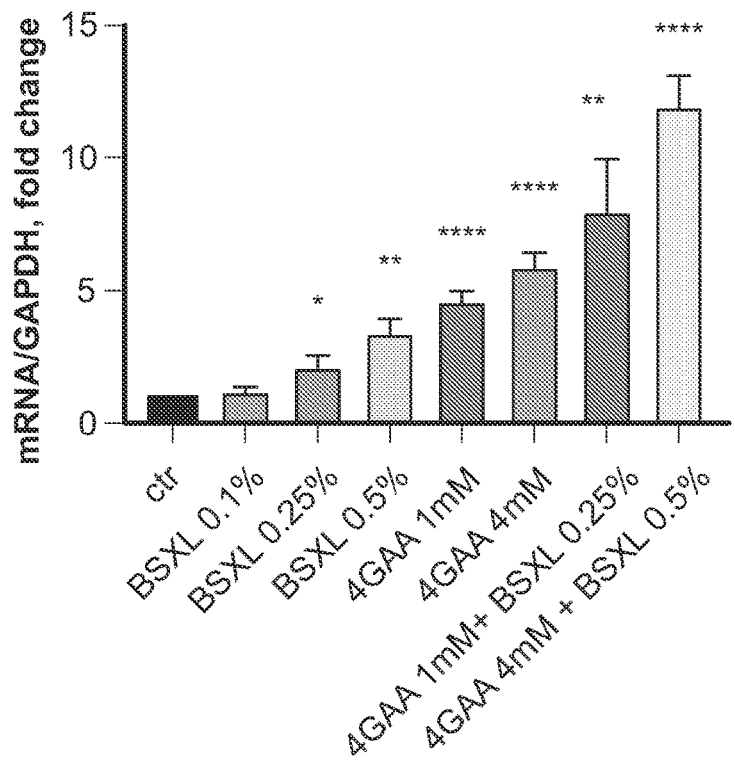
FIGS. 8A-8B illustrate the fold change of EGF mRNA in Donor G keratinocyte cells comparing the 4 amino acid combination (Ala, Gln, Gly, Ser; 4GAA) 1 mM or 4 mM and/or plant extract combination containing, e.g., *Boswellia* (BSXL) alone (0.1%, 0.25%, 0.5%) or in combination at different concentrations. The data are shown in graphical form (FIG. 8A) and tabular form (FIG. 8B). * p<0.05, p<0.01, * p<0.001, ****p<0.0001 vs untreated control (ctr). n=3
Figures 9A, 9B:
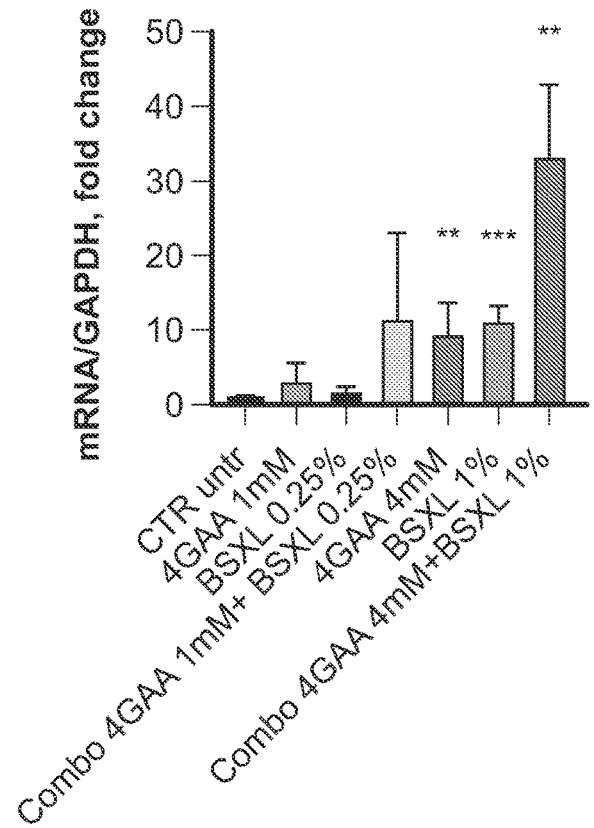
FIGS. 9A-9B present the fold change of EGF mRNA comparing the 4 amino acid combination (Ala, Gln, Gly, Ser; 4GAA) and *Boswellia* plant extract combination (BSXL; Bosexil®) alone or in combination at different concentrations with Donor O keratinocyte cells. The data are shown in graphical form (FIG. 9A) and tabular form (FIG. 9B).  p<0.01, * p<0.001 versus untreated CTR control. n=2 or n=3
Figures 10A, 10B:
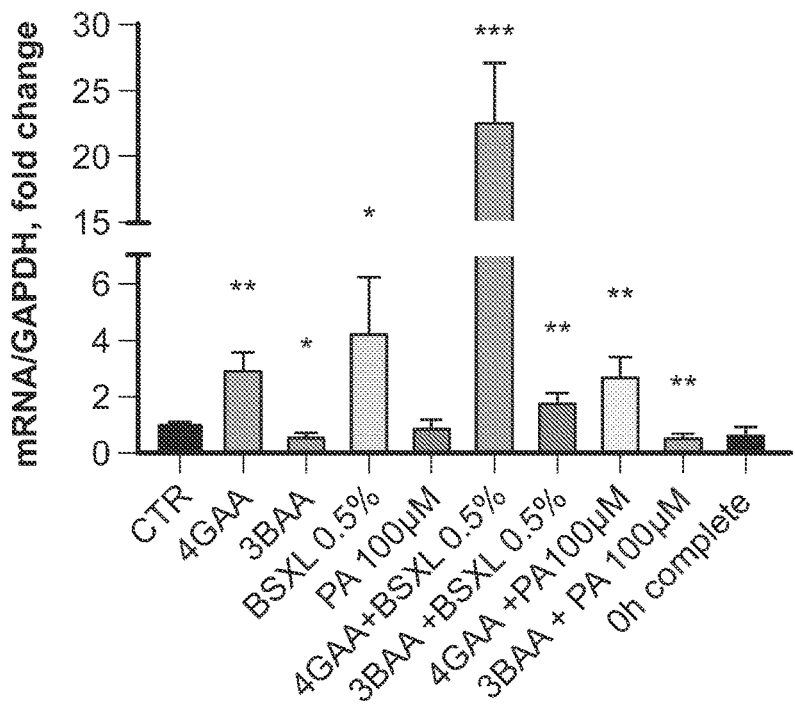
FIGS. 10A-10B present the fold change of EGF mRNA comparing the 4 amino acid combination (Ala, Gln, Gly, Ser; 4GAA; 4 mM), 3 amino acid combination (Cys 1 mM, His 0.5 mM, Tyr 1 mM; 3BAA), 0.5% *Boswellia* plant extract combination (BSXL), and Piperonylic acid (100 µM; PA) alone or in combination with Donor G keratinocyte cells. The data are shown in graphical form (FIG. 10A) and tabular form (FIG. 10B). * p<0.05, p<0.01, * p<0.001 versus untreated CTR control. n=3
Figures 11A, 11B:
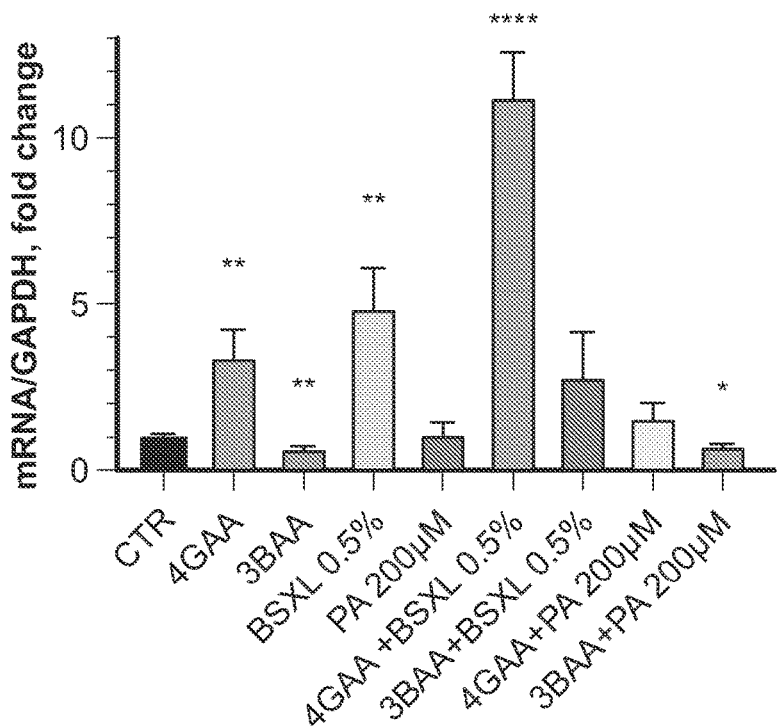
FIGS. 11A-11B demonstrate the fold change of EGF mRNA comparing the 4 amino acid combination (Ala, Gln, Gly, Ser; 4GAA; 4 mM), 3 amino acid combination (Cys 1 mM, His 0.5 mM, Tyr 1 mM; 3BAA), *Boswellia* plant extract combination (BSXL), and Piperonylic acid (100 µM; PA) alone or in combination with Donor T keratinocyte cells. The data are shown in graphical form (FIG. 11A) and tabular form (FIG. 11B). * p<0.05, p<0.01, ** p<0.001 versus untreated CTR control. n=3
Figures 12A, 12B:
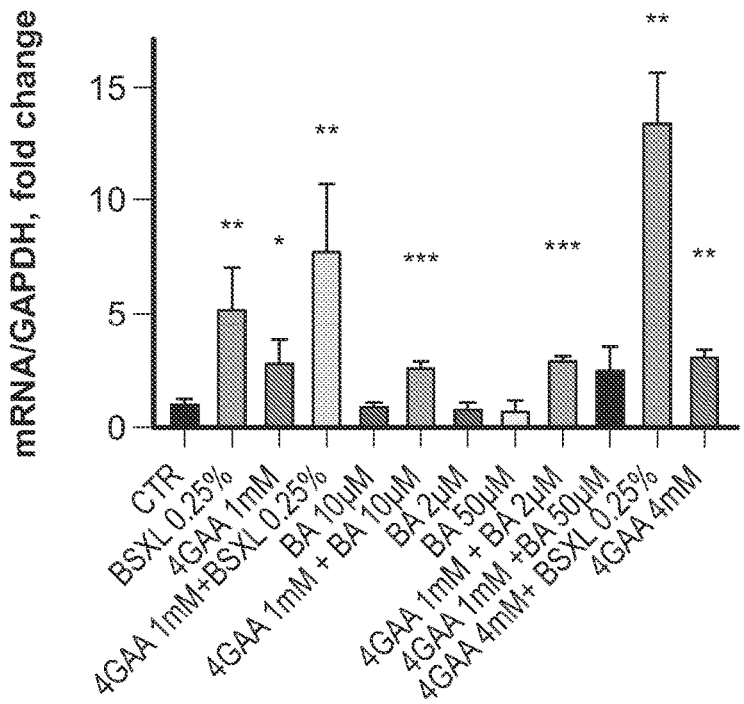
FIGS. 12A-12B illustrate the average fold change of EGF mRNA comparing the 4 amino acid combination (Ala, Gln, Gly, Ser; 4GAA; 4 mM), *Boswellia* plant extract combination (BSXL), and Boswellic acid extract (BA) alone or in combination and in various concentrations or weight percentages (wt/wt %) with Donor 0 keratinocytes. The data are shown in graphical form (FIG. 12A) and tabular form (FIG. 12B). * p<0.05, p<0.01, * p<0.001 versus untreated CTR control. n=2 or n=3
Figures 13A, 13B:
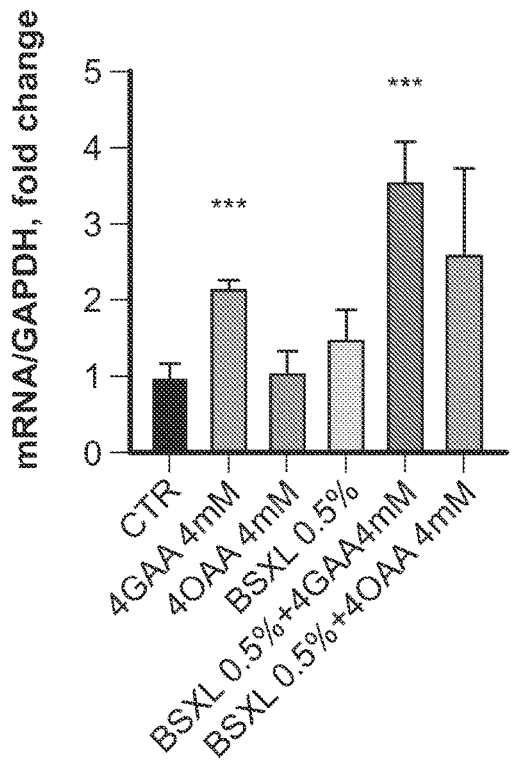
FIGS. 13A-13B show the average fold change of EGF mRNA comparing the 4 amino acid combination (Ala, Gln, Gly, Ser; 4GAA; 4 mM), alternative 4 amino acid combination (Asp, Ile, Tyr, Val; 4OAA; 4 mM), and *Boswellia* plant extract combination (BSXL; 0.5% or 0.5 w/w % in combination), alone or in combination and in various concentrations or weight percentages (wt/wt %) with Donor A keratinocytes. The data are shown in graphical form (FIG. 13A) and tabular form (FIG. 13B). *** p<0.001 versus untreated CTR control. n=3

Example 8: EGF Expression Comparison of Amino Acid Combination and Plant Extract Combination, Alone or Together Keratinocytes from different donors were cultured in amino acid-free media for 4 hours after complete differentiation and, in parallel, were treated with an amino acid combination (4GAA; alanine, glutamine, glycine, serine) at 1 mM or 4 mM and/or *Boswellia* plant extract combination (BSW or BSXL) in 0.25%, 0.5%, or 1% (w/w %) concentrations (where the combinations are 4GAA 4 mM/1% BSW (FIG. 7A); 4GAA 1 mM/0.25% BSW (FIG. 7B); 4GAA 4 mM/0.5% BSW (FIG. 7C); 4GAA 1 mM/0.5% BSW (FIG. 7D)).

Cells were harvested, RNA (EGF mRNA) was extracted, and qPCR analysis was performed with GAPDH as the housekeeping gene. See, FIGS. 7A-7D. * $p<0.05$, **$p<0.01$ vs untreated control (CTR or CTR untr).

Example 9: Comparison of Fold Change of EGF mRNA of Amino Acid Combination and Plant Extract Combination, Alone or Together, Donor G Keratinocytes from Donor G were cultured in amino acid-free media for 4 hours after complete differentiation and, in parallel, were treated with an amino acid combination (4GAA; alanine, glutamine, glycine, serine) at 1 mM or 4 mM and/or plant extract combination (BSXL) in 0.1%, 0.25% or 0.5% w/w % concentrations (where the combinations are 4GAA 1 mM/0.25% BSXL and 4GAA 4 mM/0.5% BSXL).

Cells were harvested, RNA (EGF mRNA) was extracted, and qPCR analysis was performed with GAPDH as the housekeeping gene. See, FIGS. 8A-8B. * $p<0.05$, $p<0.01$, * $p<0.001$, ****$p<0.0001$ vs untreated control (ctr).

Example 10: Comparison of Fold Change of EGF mRNA of Amino Acid Combination and Plant Extract Combination, Alone or Together, Donor O Keratinocytes from Donor O were cultured in amino acid-free media for 4 hours after complete differentiation and, in parallel, were treated with an amino acid combination (4GAA; alanine, glutamine, glycine, serine) at 1 mM or 4 mM and/or plant extract combination (BSXL) in 0.25% or 1% w/w % concentrations (where the combinations are BSXL 0.25%/1 mM 4GAA and BSXL 1%/4 mM 4GAA).

Cells were harvested, RNA (EGF mRNA) was extracted, and qPCR analysis was performed with GAPDH as the housekeeping gene. See, FIGS. 9A-9B.  $p<0.01$, * $p<0.001$ vs untreated control (CTR untr).

Example 11: Comparison of Fold Change of EGF mRNA of Amino Acid Combination and Plant Extract Combination, Alone or Together Keratinocytes from Donor G were cultured in amino acid-free media for 4 hours after complete differentiation and, in parallel, were treated with an amino combination (4GAA at 4 mM: alanine, glutamine, glycine, serine; 3BAA: cysteine (Cys), histidine (His), tyrosine (Tyr): Cys 1 mM, His 0.5 mM, Tyr 1 mM) and/or plant extract combination (BSXL) in 0.5% and/or piperonylic acid (100 M; PA) (where the combinations are 4GAA 4 mM/0.5% BSXL; 3BAA 2.5 mM/0.5% BSXL; 4GAA 4 mM/100 M PA; 3BAA 2.5 mM/100 M PA).

The same experiment was performed with similar cells and different combinations of amino acids, as well as a compound (PA) that upregulates EGFR (EGF Receptor).

Cells were harvested, RNA (EGF mRNA) was extracted, and qPCR analysis was performed with GAPDH as the housekeeping gene. See, FIGS. 10A-10B. * $p<0.05$, $p<0.01$, * $p<0.001$ versus untreated control (CTR).

Example 12: Comparison of Fold Change of EGF mRNA of Amino Acid Combination and Plant Extract Combination, Alone or Together, Donor G Keratinocytes from Donor G were cultured in amino acid-free media for 4 hours after complete differentiation and, in parallel, were treated with an amino combination (4GAA at 4 mM: alanine, glutamine, glycine, serine; 3BAA: cysteine (Cys), histidine (His), tyrosine (Tyr): Cys 1 mM, His 0.5 mM, Tyr 1 mM) and/or plant extract combination (BSXL) in 0.5% and/or piperonylic acid (200 M; PA) (where the combinations are 4GAA 4 mM/0.5% BSXL; 3BAA 2.5 mM/0.5% BSXL; 4GAA 4 mM/200 M PA; 3BAA 2.5 mM/200 M PA).

The same experiment was performed with similar cells and different combinations of amino acids, as well as a compound (PA) that upregulates EGFR (EGF Receptor).

Cells were harvested, RNA (EGF mRNA) was extracted, and qPCR analysis was performed with GAPDH as the housekeeping gene. See, FIGS. 11A-11B. * $p<0.05$, $p<0.01$, * $p<0.001$ versus untreated control (CTR).

Example 13: Comparison of Fold Change of EGF mRNA of Amino Acid Combination, Plant Extract, and Plant Extract Combination, Alone or Together, Donor O Keratinocytes from Donor 0 were cultured in amino acid-free media for 4 hours after complete differentiation and, in parallel, were treated with an amino combination (4GAA; alanine, glutamine, glycine, serine) at 1 mM or 4 mM and/or plant extract combination (BSXL) in 0.25% and/or Boswellic acid (BA) in 2 µM, 10 µM, and 50 µM concentrations (where the combinations are 4GAA 1 mM/0.25% BSXL; 4GAA 4 mM/0.25% BSXL; 4GAA 1 mM/10 M BA; 4GAA 1 mM/2 M BA; 4GAA 1 mM/50 M BA).

Cells were harvested, RNA (EGF mRNA) was extracted, and qPCR analysis was performed with GAPDH as the housekeeping gene. See, FIGS. 12A-12B. * $p<0.05$, $p<0.01$, * $p<0.001$ vs untreated control (CTR).

Example 14: Comparison of Fold Change of EGF mRNA of Amino Acid Combination and Plant Extract Combination, Alone or Together, Donor a Keratinocytes from Donor A were cultured in amino acid-free media for 4 hours after complete differentiation and, in parallel, were treated with an amino combination (4GAA: alanine, glutamine, glycine, serine; 40AA: aspartic acid, isoleucine, tyrosine, valine) at 4 mM and/or plant extract combination (BSXL) in 0.5% (where the combinations are 4GAA 4 mM/0.5% BSXL; 40AA 4 mM/0.5% BSXL).

Cells were harvested, RNA (EGF mRNA) was extracted, and qPCR analysis was performed with GAPDH as the housekeeping gene. See, FIGS. 13A-13B. *** $p<0.001$ vs untreated control (CTR).

Example 15: Comparison of Fold Change of EGF mRNA of Amino Acid Combination and Plant Extract Combination, Alone or Together Keratinocytes from Donor A (n=1), Donor G (n=3), and Donor T (n=2) were cultured in amino acid-free media for 4 hours after complete differentiation and, in parallel, were treated with an amino combination (4GAA: alanine, glutamine, glycine, serine) at 4 mM and/or plant extract combination (BSXL) in 0.5% (where the combination is 4GAA 4 mM/0.5% BSXL).

Figure 14C:
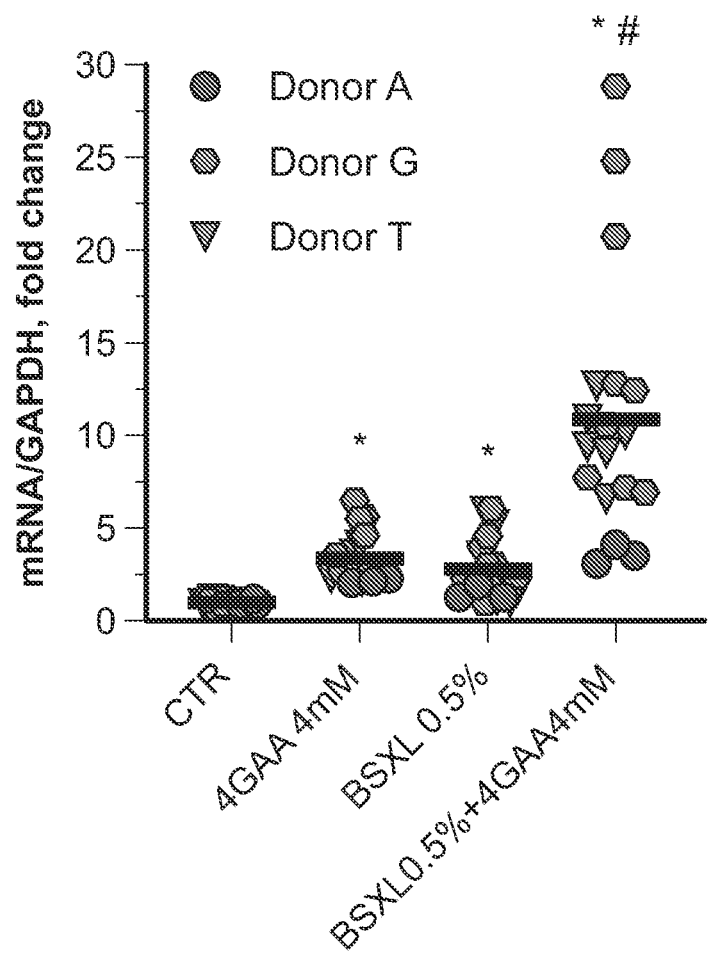

Cells were harvested, RNA (EGF mRNA) was extracted, and qPCR analysis was performed with GAPDH as the housekeeping gene. See, Averages: FIGS. 14A-14C. * $p<0.05$ vs untreated control (CTR).

Example 16: Testing Transepidermal Water Loss (TEWL) Change

Figure 15A:
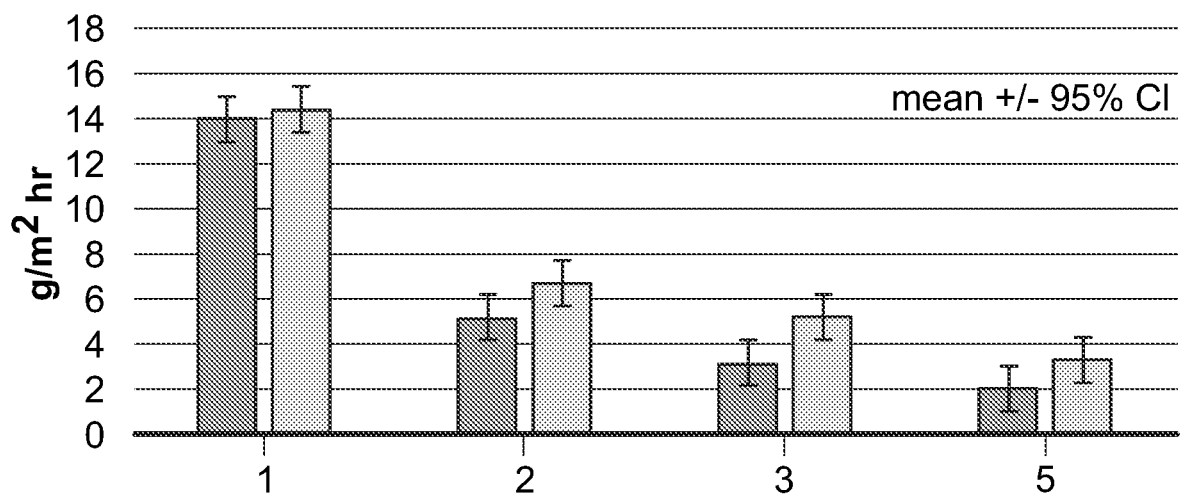
FIGS. 15A-15B present the transepidermal water loss (TEWL) change after test material (Active (4GAA) in an oil/water (O/W) vehicle, left column; Placebo, right column) application for 10 days on 12 subjects who are then subjected to repeated tape strips (15 tape strips).
Figure 15B:
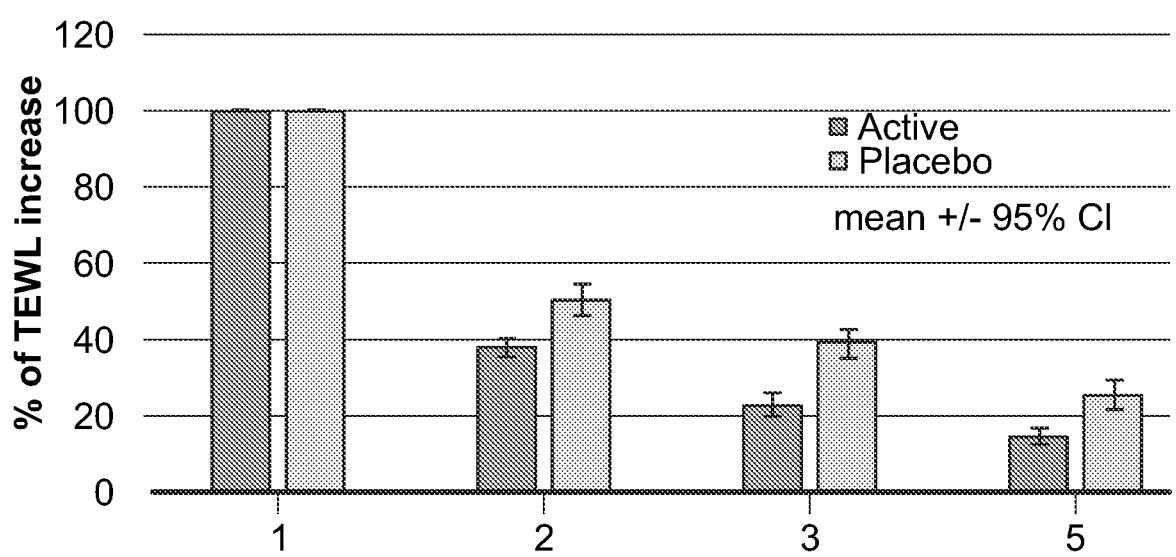

In order to determine transepidermal water loss (TEWL) change, test materials (Active (4GAA), left column; Placebo, right column) were applied for 5 days on the skin of 12 subjects who were then subjected to 15 repeated tape strips. See, FIGS. 15A-15B. The active 4GAA amino acid combination contained alanine (4%), glutamine (4%), glycine (4%), serine (4%) at a total concentration of 12% in an oil/water (O/W) vehicle and placebo. The baseline, Day 1, was immediately after tape-stripping. Days 2, 3, and 5 are each after two treatments per day of test materials.

Example 17: Measurement of Skin Hydration

Figure 16:
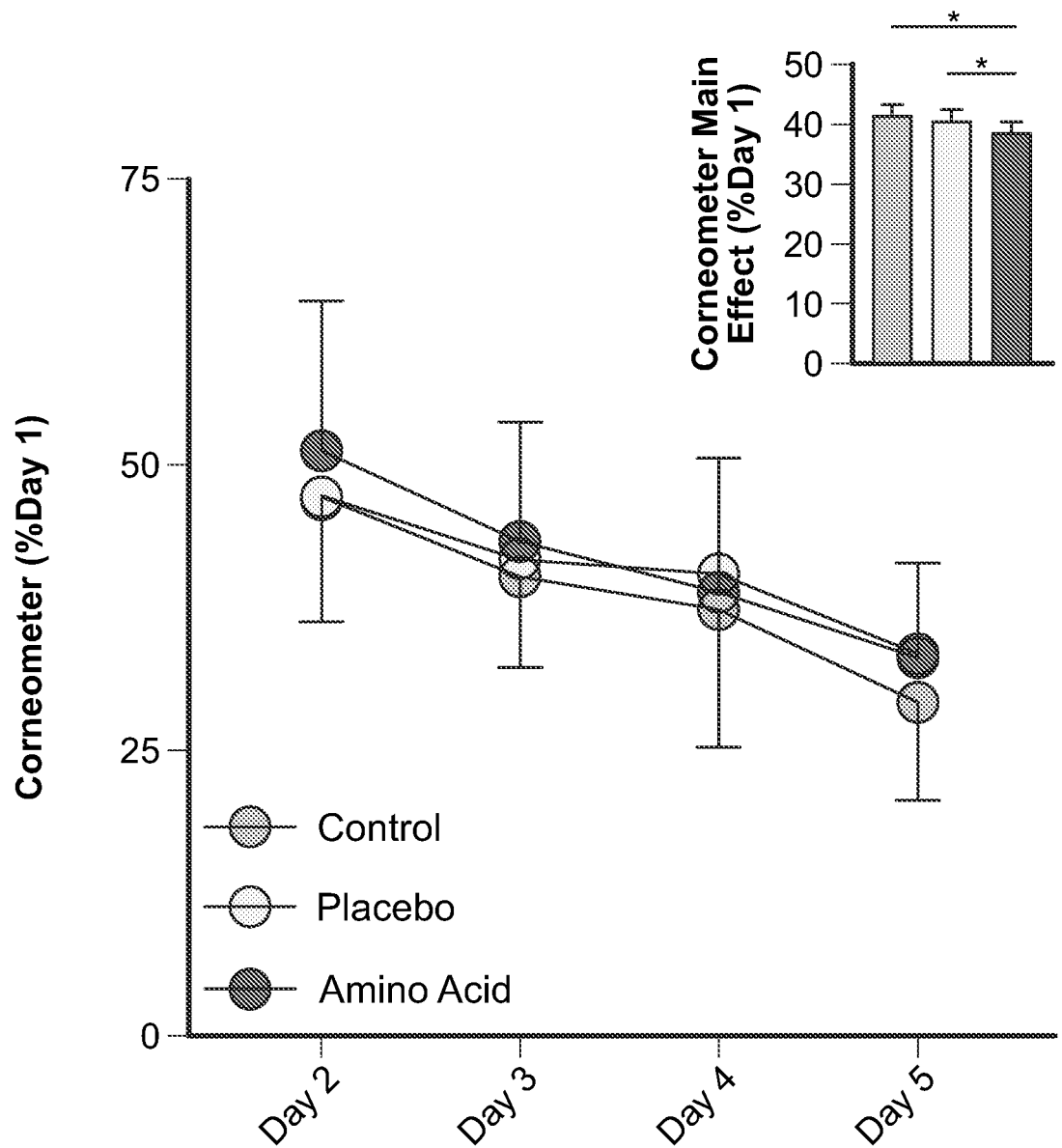
FIG. 16 presents skin barrier improvement measuring skin hydration (Y-axis) after test material application for 10 days on 25 subjects who were then subjected to repeated tape strips (25). Control represents untreated (top graphical line at Day 3; left column-inset); Placebo represents water/oil/water (W/O/W) vehicle without active (middle graphical line at Day 3; center column-inset); Amino Acid represents the 4 amino acid combination (Ala (4%), Gln (4%), Gly (4%), Ser (4%)) in the W/O/W vehicle (bottom graphical line at Day 3; right column-inset). *, p-value=0.05. Inset: Control (left), Placebo (center), Amino Acid (right).

In order to determine skin barrier improvement, test materials (Untreated control; Placebo; Active Amino Acid (4GAA)) were applied for 5 days on the skin of 25 subjects who were then subjected to 15 repeated tape strips. See, FIG. 16. Control represents untreated (top graphical line at Day 3; left column-inset); Placebo represents water/oil/water (W/O/W) vehicle without active (middle graphical line at Day 3; center column-inset); Amino Acid represents the 4 amino acid combination (Ala (4%), Gln (4%), Gly (4%), Ser (4%)) in the W/O/W vehicle (bottom graphical line at Day 3; right column-inset). *, p-value=<0.05. Inset: Control (left), Placebo (center), Amino Acid (right).

Corneometry was used to measure skin hydration of the superficial layers of the skin of the subjects (stratum corneum).

As various changes can be made in the above-described subject matter without departing from the scope and spirit of the present disclosure, it is intended that all subject matter contained in the above description, or defined in the appended claims, be interpreted as descriptive and illustrative of the present disclosure. Many modifications and variations of the present disclosure are possible in light of the above teachings. Accordingly, the present description is intended to embrace all such alternatives, modifications and variances which fall within the scope of the appended claims.

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the disclosure.

What is claimed is:

1. A topical formulation, comprising:
    (a) as free amino acids, a therapeutically effective amount consisting essentially of a combination of glutamine, glycine, alanine, and serine, or salts thereof,
        wherein each free amino acid has a ratio to each of the other free amino acids of: 1:100 or greater; and
    (b) a therapeutically effective amount of a plant extract comprising *Boswellia* extract,
        wherein the therapeutically effective amount of the combination and the therapeutically effective amount of the plant extract improve barrier integrity of skin cells when tested by a method detecting EGF expression and determining that EGF is upregulated by a 1.5-40 average fold change of formulation treated as compared to untreated skin,
        wherein the therapeutically effective amount of the combination and the therapeutically effective amount of plant extract improve barrier integrity of the skin and/or skin barrier repair.

2. The topical formulation according to claim 1, wherein each of the free amino acids is present at a concentration of: 0.1 mM or greater; 10 mM or less; or 0.1 mM to 10 mM.

3. The topical formulation according to claim 1, wherein each of the free amino acids is present at a weight percent to the formulation (wt/wt %) of: 0.001 wt % or greater; 1 wt % or less; or 0.001 wt % to 1 wt %.

4. The topical formulation according to claim 1, wherein the therapeutically effective amount of the plant extract is present at a weight percentage (w/w %) of the formulation of: 0.025 w/w % or greater; 5 w/w % or less; or 0.025 w/w %-5 w/w %.

5. The topical formulation according to claim 1, wherein the amino acid combination and the plant extract are in a ratio of: 1:100 or greater; 100:1 or less; or 1:100 to 100:1.

6. The topical formulation according to claim 1, wherein the plant extract is selected from the group consisting of: *Boswellia serrata* resin extract, *Boswellia serrata* extract, olibanum, frankincense, and any combinations thereof.

7. The topical formulation according claim 1, wherein the therapeutically effective amount of the combination of free amino acids and the therapeutically effective amount of the plant extract inhibit 5-lipoxygenase, decrease mobilization of calcium ions, decrease activation of MAP kinases, or any combination thereof.

8. The topical formulation of claim 1, further comprising:
a texturing and/or a bulking agent;
a phospholipid;
an anti-caking agent;
a dermatologically acceptable carrier;
additives, or
any combination thereof.

9. The topical formulation of claim 8, wherein the bulking agent comprises cellulose, microcrystalline cellulose, or combinations thereof.

10. The topical formulation of claim 8, wherein the phospholipid comprises lecithin, phosphatidylcholine, or combinations thereof.

11. The topical formulation of claim 8, wherein the anti-caking agent comprises silica.

12. The topical formulation of claim 8, wherein the additives are selected from the group consisting of: vitamins, minerals, preservatives, desquamation agents, anti-acne agents, anti-wrinkle agents/anti-atrophy agents, hydroxyl acids, anti-oxidants/radical scavengers, chelators, flavonoids, anti-inflammatory agents, anti-cellulite agents, topical anesthetics, tanning agents, skin lightening agents, skin soothing and skin healing agents, antimicrobial and antifungal agents, sunscreen agents, conditioning agents, structuring agents, thickening agents, preservatives and any combinations thereof.

13. The topical formulation according to claim 1, wherein the free amino acid is in L-form.

* * * * *